(12) United States Patent
Patience

(10) Patent No.: US 6,942,863 B2
(45) Date of Patent: Sep. 13, 2005

(54) GAMMA HERPESVIRUS DNA AND METHODS OF USE

(75) Inventor: Clive Patience, Beverly, MA (US)

(73) Assignee: Immerge Biotherapeutics, Inc., Cambridge, MA (US)

( * ) Notice: Subject to any disclaimer, the term of this patent is extended or adjusted under 35 U.S.C. 154(b) by 0 days.

(21) Appl. No.: 10/055,364

(22) Filed: Jan. 23, 2002

(65) Prior Publication Data

US 2002/0155433 A1 Oct. 24, 2002

Related U.S. Application Data

(62) Division of application No. 09/612,204, filed on Jul. 7, 2000.
(60) Provisional application No. 60/168,532, filed on Dec. 2, 1999, and provisional application No. 60/142,736, filed on Jul. 8, 1999.

(51) Int. Cl.[7] .................. A61K 39/00; A61K 39/245; C07K 14/00
(52) U.S. Cl. ............... 424/185.1; 424/229.1; 530/350
(58) Field of Search ................. 530/350, 300; 424/185.1, 229.1, 230.1

(56) References Cited

PUBLICATIONS

Dorland's Illustrated Medical Dictionary, 28th edition. WB Saunders Company; Philadelphia. 1994, pp. 198 and 1426.*
Fishman. Xenotransplantation. 2000; 7: 93–95.*
Woodland et al. Viral Immunology. 2001; 14 (3): 217–226.*
Simas, et al., "Murine gammaherpesvirus 68: a model for the study of gammaherpesvirus pathogenesis," Trends in Microbiology, vol. 6, No. 7, pp. 276–282 (Jul. 1998).
Bahr, et al., "Structural organization of a conserved gene cluster of Tupaia herpesvirus encoding the DNA polymerase, glycoprotein B, a probable processing and transport protein, and the major DNA binding protein," Virus Research, pp. 123–136 (1999).
Ehlers, et al., "Detection of two novel porcine herpesviruses with high similarity to gammaherpesviruses," Journal of General Virology, pp. 971–978 (1999).
Ulrich, et al., "Characterization of the DNA polymerase loci of the novel porcine lymphotropic herpesviruses 1 and 2 in domestic and feral pigs," pp. 3199–3205 (1999).
Morozov, et al., "Detection of a Novel Strain of Porcine Circovirus in Pigs with Postweaning Multisystemic Wasting Syndrome," vol. 36, No. 9, pp. 2535–2541 (Sep. 1998).

* cited by examiner

*Primary Examiner*—Shanon Foley
(74) *Attorney, Agent, or Firm*—Elliot M. Olstein; Alan J. Grant

(57) ABSTRACT

Isolated polynucleotides and polypeptides derived from the genome of swine gamma-herpesviruses are disclosed, including recombinant cells and vectors encoding such polypeptides and expressing such polynucleotides. Use of the novel polynucleotides as probes of the swine genome is also described. Assay methods employing antibodies against the isolated polypeptides are also disclosed.

5 Claims, 14 Drawing Sheets

Figure 1(a)

```
HHV8PEP          --------------------MTPRSR-LATLGTVILLVCFCAG--AAHSRGDTFQ--
RHESRHADPEP      --------------------MMITNRTRRLLRAWVVIIAIGTAVG--ENVTTPKGAT--
MURH68PEP        --------------------MYPTVKSMRVAHLTNLLTLLCLLCHTHLYVCQPTTLR--
BOVINEH4PEP      YYKTILFFALIKVCSFNQTTTHSTTTSPSISSTTSSTTTSTSKPSNTTSTNSSLAASPQ
ATELINEH3PEP     -------------MTLNR---CVLLIVLTFSTACS----------Q--
SAIMIRIPEP       -------------MVPNK---HLLLIILSFSTACG----------Q--
EQH2PEP          --------------------MGVGGGPRVVLCLWCVAALLCQGVAQEVVAETTTPFA--
EQH5PEP          --------------------MVAWFGLWGFARLMATLALLCGRVALDESSATPSIPP--
ALCELPEP         --------------------MAHTGSTVCAFLIFAVLKNVFCQTPTSSSEVEDVIPEAN-
EBVPEP           --------------------MTRRRVLSVVVLLAALACRLGA-----Q--TPEQ--

HHV8PEP          --TSSSPTPPGSSSKAPTKPGEEASGPKSVDFYQFRVCSAS-ITGELFRFNLEQTCPDTK
RHESRHADPEP      --TTAKPTP-GPS--TPTPP---ENPPR-AEAFKPRVCSAS-ATGELFRFNLEKTCPGTE
MURH68PEP        --QPSDMTP-AQDAPTETPPPLSTNTNR--GFEYFRVCGVA-ATGETFRFDLDKTCPSTQ
BOVINEH4PEP      NTSTSKPSTDNQGTSTPTIPTVTDDTAS-KNFYKYRVCSASSSSGELFRFDLDQTCPDTK
ATELINEH3PEP     ----TTPASSDEN--GKTPAIEK--EYF----K-YRVCSAS-TTGELFRFNLDRACPSTE
SAIMIRIPEP       ----TTPTTAVEK--NKTQAIYQ--EYF----K-YRVCSAS-TTGELFRFDLDRTCPSTE
EQH2PEP          ---THRPEVVAEE--NPANP-----FLP----F---RVCGASPTGGEIFRFPLEESCPNTE
EQH5PEP          ---THKPAVHHED--NTTNP-----FLL----F---RVCGASPTG-EIFRFPLEENCPNTE
ALCELPEP         --TVSDNIIRQQR--NNTAKGIHSDPSA----FPPRVCSAS-NIGDIFRFQTSHSCPNTK
EBVPEP           ---PAPPATTVQP--TATRQ-----QTS----FPFRVCELS-SHGDLFRFSSDIQCPSFG

HHV8PEP          DKY-HQEGILLVYKKNIVPHIFKVRRYRKIATSVTVYRGLTES--AITNKYELPRPVPLY
RHESRHADPEP      DKT-HQEGILMVFKKNIVPHIFKVRRYRKVATSVTVYRGWTET--AVTGKQEVIRPVPQY
MURH68PEP        DKK-HVEGILLVYKINIVPYIFKIRRYRKIITQLTIWRGLTTS--SVTGKFEMATQAHEW
BOVINEH4PEP      DKK-HVEGILLVLKKNIVPYIFKVRKYRKIATSVTVYRGWSQA--AVTNRDDISRAIPYN
ATELINEH3PEP     DKV-HREGILLVYKKNIVPHIFKVRRYKKIATSVRIFNGWSREGVAITNKWELSRAVPKY
SAIMIRIPEP       DKV-HKEGILLVYKKNIVPYIFKVRRYKKITTSVRIFNGWTREGVAITNKWELSRAVPKY
EQH2PEP          DKD-HIEGIALIYKTNIVPYVFNVRKYRKIMTSTTIYKGWSED--AITNQHTRSYAVPLY
EQH5PEP          DKE-HVEGILLIYKTNIVPYIFNVRKYRKLVTSTTIYKGWSQD--AITNQYTSSFAMPLW
ALCELPEP         DKE-HNEGILLIFKENIVPYVFKVRKYRKIVTTSTIYNGIYAD--AVTNQHVFSKSVPIY
EBVPEP           TRENHTEGLLMVFKDNIIPYSFKVRSYTKIVTNILIYNGWYAD--SVTNRHEEKFSVDSY

HHV8PEP          EISHMDSTYQCFSSMKVNVNGVENTFTDRDDVNTTVFLQPVEGLTDNIQRYFSQPVIYAE
RHESRHADPEP      EINHMDTTYQCFSSMRVNVNGIVNTYTDRDFTNQTVFLQPVEGLTDNIQRYFSQPVLYTT
MURH68PEP        EVGDFDSIYQCYNSATMVVNNVRQVYVDRDGVNKTVNIRPVDGLTGNIQRYFSQPTLYSE
BOVINEH4PEP      EISMIDRTYHCFSAMATVINGILNTYIDRDSENKSVPLQPVAGLTENINRYFSQPLIYAE
ATELINEH3PEP     EINLMDKNYQCHNCMQIEVNGLLNSYCDRDGNNKTVDLKPVDGLTGAITRYVSQPKIFAD
SAIMIRIPEP       EIDIMDKTYQCHNCMQIEVNGMLNSYYDRDGNNKTVDLKPVDGLTGAITRYISQPKVFAD
EQH2PEP          EVQMMDHYYQCFSAVQVNEGGHVNTYDRDGWNETAFLKPADGLTSSITRYQSQPEVYAT
EQH5PEP          EARLVDYNYECYNGIQVTENGHLTTYVDRDGYNESVRLVPADGLTSSIRRYHSQPELYVT
ALCELPEP         ETRRMDTIYQCYNSLDVTVGGNLLVYTDNDGSNMTVDLQPVDGLSNSVRRYHSQPEIHAE
EBVPEP           ETDQMDTIYQCYNAVKMTKDGLTRVYVDRDGVNITVNLKPTGGLANGVRRYASQTELYDA

HHV8PEP          PGWFPGIYRVRTTVNCEIVDMIARSAEPYNYFVTSLGDTVEVSPFCYNESSCST-TPSNK
RHESRHADPEP      PGWFPGIYRVRTTVNCEIVDMIARSAEPYSYFVTALGDTVEVSPFCHNDSTCSV-AEKTE
MURH68PEP        PGWMPGFYRVRTTVNCEIVDMVARSMDPYNYIATALGDSLELSPFQTFDNTSQS-TAPKR
BOVINEH4PEP      PGWFPGIYRVRTTVNCEVVDMYARSVEPYTHFITALGDTIEISPFCHNNSQCTTGNSTSR
ATELINEH3PEP     AGWLWGTYKTRTTVNCEIVEMFARSADPYTYFVTALGDTVEVSPFCDAENSCPN----AS
SAIMIRIPEP       PGWLWGTYRTRTTVNCEIVDMFARSADPYTYFVTALGDTVEVSPFCDVDNSCPN----AT
EQH2PEP          PRNLLWSYTTRTTVNCEVTEMSARSMKPFEPFVTSVGDTIEMSPFLKENGTEPE--KILK
EQH5PEP          PRNLLWSYTTRTTVNCEVIDMSARSIKPFAPFVTASGDSIETSPFYT-NASR-------R
ALCELPEP         PGWLLGGYRRRTTVNCEVTETDARAVPPFRYFITNIGDTIEMSPFWSKAWNETEFS--GE
EBVPEP           PGWLIWTYRTRTTVNCLITDMMAKSNSPFDFFVTTTGQTVEMSPFYDGKNKETF----HE
```

Figure 1(b)

```
HHV8PEP        NGLSVQVVLNHTVVTYSDRGTSPTPQNRIFVETGAYTLSWASESKTTAVCPLALWKTFPR
RHESRHADPEP    NGLGARVLTNYTMVDFATR--APTTETRVFADSGEYTVSWKAEDPKSAVCALTLWKTFPR
MURH68PEP      ADMRVREVKNYKFVDYNNRGTAPAGQSRTFLETPSATYSWKTATRQTATCDLVHWKTFPR
BOVINEH4PEP    DATKVWIEENHQTVDYERRG-HPTKDKRIFLKDEEYTISWKAEDRERAICDFVIWKTFPR
ATELINEH3PEP   DVLSSQVDFNHTVVDYGNRATSQQHGKRIFAHTLDYSVSWEAINKTTSVCSMVFWKGFQR
SAIMIRIPEP     DVLSVQIDLNHTVVDYGNRATSQQHKKRIFAHTLDYSVSWEAVNKSASVCSMVFWKSFQR
EQH2PEP        RPHSIQLLKNYAVTKYGVGLGQADNATRFFAIFGDYSLSWKATTENSSYCDLILWKGFSN
EQH5PEP        VP--VQVLYNYSVTDYGVGLGSGENVTRFFATLNDFSISWKAATENSSYCPLVLWKGFPS
ALCELPEP       PDRTLTVAKDYRVVDYKFRGTQPQGHTRIFVDKEEYTLSWAQQFRNISYCRWAHWKSFDN
EBVPEP         RADSFHVRTNYKIVDYDNRGTNPQGERRAFLDKGTYTLSWKLENR-TAYCPLQHWQTFDS

HHV8PEP        SIQTTHEDSFHFVANEITATFTAP---LTPVANFTDTYSCLTSDINTTLNASKAKLASTH
RHESRHADPEP    AIQTTHEASYHFVANDVTATFTSP---LSEVANFTGTYSCLDEVIQKTLNDTIKKLSDTH
MURH68PEP      AIQTAHEHSYHFVANEVTATFNTP---LTEVENFTSTYSCVSDQINKTISEYIQKLNNSY
BOVINEH4PEP    AIQTIHNESFHFVANEVTASFLTSNQEETELRGNTEILNCMNSTINETLEETVKKFNKSH
ATELINEH3PEP   AIQTEHDSTYHFIANEITAGFSTS---KETLASFSSEYSCLMSDINSTLTDKIGRVNNTH
SAIMIRIPEP     AIQTEHDLTYHFIANEITAGFSTV---KEPLANFTSDYNCLMTHINTTLEDKIARVNNTH
EQH2PEP        AIQTQHNSSLHFIANDITASFSTP--LEEEAN-FNETFKCIWNNTQEEIQKKLKEVEKTH
EQH5PEP        AIQTKHEKSYHFIADAVTASFTTP--LTDETSYFNTTYQCAWQDIEGEIQKRFDPVSKTH
ALCELPEP       AIKTEHGKSLHFVANDITASFYTP---NTQTREVLGKHVCLNNTIESELKSRLAKVNDTH
EBVPEP         TIATETGKSIHFVTDEGTSSFVTN---TTVGIELPDAFKCIEEQVNKTMHEKYEAVQDRY

HHV8PEP        VP-NGTVQYFHTTGGLYLVWQPMSAINLTHAQ-GDSGNPTSSPPPSASP---------M
RHESRHADPEP    VT-NGSAQYYKTEGGLFLLWQPLTPLSLVDEMRGLNG---TTPAP---P----------A
MURH68PEP      VA-SGKTQYFKTDGNLYLIWQPLEHPEIEDID--EDSDPEPTPAP---P----------K
BOVINEH4PEP    IR-DGEVKYYKTNGGLFLIWQAMKPLNLSEHT------N-YTIER---N----------N
ATELINEH3PEP   VP-NGTAQYFKTEGGMILVWQPLTAIELEEAMIEATTVSPTPLS--------------T
SAIMIRIPEP     TP-NGTAEYYQTEGGMILVWQPLIAIELEEAMLEATTSPVTPSAP-------------T
EQH2PEP        RP-NGTAKVYKTTGNLYIVWQPLIQIDLLDTHAKLYNLTNATASPTSTP-----------
EQH5PEP        AR-NGSVQIYKTSGNLYVVWQPLVQLDLLAAHAKTINSTDNSTSPTTAPN--------TT
ALCELPEP       SP-NGTAQYYLTNGGLLLVWQPLVQQKLLDAKGLLDAVKKQQNTTTT------------T
EBVPEP         TKGQEAITYFITSGGLLLAWLPLTPRSLATVKNLTELTTPTSSPPSSPSPPAPSAARGST

HHV8PEP        TTSASRRKRRSASTAAAGG---GGSTDN-----LSYTQLQFAYDKLRDGINQVLEELSRA
RHESRHADPEP    TTSTVSRVRRSVNTNEQ-------ATDN-----LAAPQLQFAYDKLRASINKVLEELSRA
MURH68PEP      STRRKREAADNGNSTSEVS---KGSENP-----LITAQIQFAYDKLTTSVNNVLEELSRA
BOVINEH4PEP    KTGNKSRQKRSVDTKTFQG------AKG------LSTAQVQYAYDHLRTSMNHILEELTKT
ATELINEH3PEP   AHLTSRRTGRRKRDVSAG------SENS-----VLLAQIQYAYDKLRQSINNVLEELAIT
SAIMIRIPEP     SSSRSKRAIRSIRDVSAG------SENN-----VFLSQIQYAYDKLRQSINNVLEELAIT
EQH2PEP        -TTSPRRRRRDTSSVSGGG---NNGDNSTKEESVAASQVQFAYDNLRKSINRVLGELSRA
EQH5PEP        TSTSSRRKRRDTGNTATNN---SSSNNSSMEENLATSQVQFAYDQLRKSINRVLEQLSRV
ALCELPEP       TTTRSRRQRRSVSSGIDDV---YTAEST-----ILLTQIQFAYDTLRAQINNVLEELSRA
EBVPEP         PAAVLRRRRRDAGNATTPVPPTAPGKSLGTLNNPATVQIQFAYDSLRRQINRMLGDLARA

HHV8PEP        WCREQVRDNLMWYELSKINPTSVMTAIYGRPVSAKFVGDAISVTECINVDQSSVNIHKSL
RHESRHADPEP    WCREQVRDTYMWYELSKINPTSVMTAIYGRPVSAKFVGDAISVTDCVAVDQASVSIHKSL
MURH68PEP      WCREQVRDTLMWYELSKVNPTSVMSAIYGKPVAARYVGDAISVTDCIYVDQSSVNIHQSL
BOVINEH4PEP    WCREQKKDNLMWYELSKINPVSVMAAIYGKPVAVKAMGDAFMVSECINVDQASVNIHKSM
ATELINEH3PEP   WCREQVRQTMIWYEIAKINPTSVMTAIYGKPVSAKALGDVISVTECINVDQTSVSIHKSL
SAIMIRIPEP     WCREQVRQTMVWYEIAKINPTSVMTAIYGKPVSRKALGDVISVTECINVDQSSVSIHKSL
EQH2PEP        WCREQYRASLMWYELSKINPTSVMSAIYGRPVSAKLIGDVVSVSDCISVDQKSVFVHKNM
EQH5PEP        WCQNQYRASLMWYELSKINPTSVMSAIYGRPVSAKLVGDVVQISDCITVDQESVFVHRNL
ALCELPEP       WCREQHRASLMWNELSKINPTSVMSSIYGRPVSAKRIGDVISVSHCVVVDQDSVSLHRSM
EBVPEP         WCLEQKRQNMVLRELTKINPTTVMSSIYGKAVAAKRLGDVISVSQCVPVNQATVTLRKSM
```

Figure 1(c)

```
HHV8PEP        RTN---SKDVCYARPLVTFKFLNSSNLFTGQLGARNEIILTNNQVETCKDTCEHYFITRN
RHESRHADPEP    RTS---TPGMCYSRPPVTFRFLNSTTLFKGQLGPRNEIILTDNQVEACKETCEHYFIASN
MURH68PEP      RLQH--DKTTCYSRPRVTFKFINSTDPLTGQLGPRKEIILSNTNIETCKDESEHYFIVGE
BOVINEH4PEP    RTD---DPKVCYSRPLVTFKFVNSTATFRGQLGTRNEILLTNTHVETCRPTADHYFFVKN
ATELINEH3PEP   KTT---NNDVCYSRPPVTFKFVNSSQLFKGQLGARNEILLSESLVENCHQNAEHFFTAKN
SAIMIRIPEP     KTE---NNDICYSRPPVTFKFVNSSQLFKGQLGARNEILLSESLVENCHQNAETFFTAKN
EQH2PEP        KVPG--KEDLCYTRPVVGPKFINGSELFAGQLGPRNEIVLSTSQVEVCQHSCEHYFQAGN
EQH5PEP        RVPG--SKDLCYTRPVVGFKFINGSELFVGQLGARNEILLSTNLVEVCQHSCEHYFQGGN
ALCELPEP       RVPGRDKTHECYSRPPVTFKFINDSHLYKGQLGVNNEILLTTTAVEICHENTEHYFQGGN
EBVPEP         RVPG--SETMCYSRPLVSFSFINDTKTYEGQLGTDNEIFLTKKMTEVCQATSQYYFQSGN

HHV8PEP        ETLVYKDYAYLRTINTTDISTLNTFIALNLSFIQNIDFKAIELYSSAEKRLASSVFDLET
RHESRHADPEP    VTYYYKDYVFVKKINTSEISTLGTFIALNLSFIENIDFRVIELYSRAEKKLSGSVFDIET
MURH68PEP      YIYYYKNYIFEEKLNLSSIATLDTFIALNISFIENIDFKTVELYSSTERKLASSVFDIES
BOVINEH4PEP    MTHYFKDYKFVKTMDTNNISTLDTFLTLNLTFIDNIDFKTVELYSETERKMAS-ALDLET
ATELINEH3PEP   ETYHFKNYLHVETLPLTNISTLDTFLALNLTFIENIDFKAVELYSSGERKLAN-VFDLET
SAIMIRIPEP     ETYHFKNYVHVETLPVNNISTLDTFLALNLTFIENIDFKAVELYSSGERKLAN-VFDLET
EQH2PEP        QMYKYKDYYYVSTLNLTDIPTLHTMITLNLSLVENIDFKVIELYSKTEKRLSN-VFDIET
EQH5PEP        HIYKYKNYEYVSTMNLTDVPTLHTMITLNLSLVENVDFQVIQLYSQKEKKLSN-VFDIET
ALCELPEP       NMYFYKNYRHVKTMPVGDVATLDTFMVLNLTLVENIDFQVIELYSREEKRMST-AFDIET
EBVPEP         EIHVYNDYHHFKTIELDGIATLQTFISLNTSLIENIDFASLELYSRDEQRASN-VFDLEG

HHV8PEP        MFREYNYYTHRLAGLREDLDNTIDMNKERFVRDLSEIVADLGGIGKTVVNVASSVVTLCG
RHESRHADPEP    MFREYNYYTQRLAGLREDLDNTIDLNRDRLARDLSEIVADLGDVGRTVVNVASSVITLFG
MURH68PEP      MFREYNYYTYSLAGIKKDLDNTIDYNRDRLVQDLSDMMADLGDIGRSVVNVVSSVVTFFS
BOVINEH4PEP    MFREYNYYTQKLASLREDLDNTIDLNRDRLVKDLSEMMADLGDIGKVVVNTFSGIVTVFG
ATELINEH3PEP   MFREYNYYAQSISGLRKDFDNSQRNNRDRIIQDFSEILADLGSIGKVIVNIASSAFSLFG
SAIMIRIPEP     MFREYNYYAQSISGLRKDFDNSQRNNRDRIIQDFSEILADLGSIGKVIVNVASGAFSLFG
EQH2PEP        MFREYNYYTQNLNGLRKDLDDSIDHGRDSFIQTLGDIMQDLGTIGKVVVNVASGVFSLFG
EQH5PEP        MFREYNYYTQNLKGLRKDLDDSIHDGRDSFIQFLGDLVQDLVPVGDVIVNVASGVFSLFG
ALCELPEP       MFREYNYYTQRVTGLRRDLTD-LATNRNQFVDAFGSLMDDLGVVGKTVLNAVSSVATLFS
EBVPEP         IFREYNFQAQNIAGLRKDLDNAVSNGRNQFVDGLGELMDSLGSVGQSITNLVSTVGGLFS

HHV8PEP        SLVTGFINFIKHPLGGMLMIIIVIAIILIIFMLSRRTNTIAQAPVKMIYP----DVDRRA
RHESRHADPEP    SIVSGFINFIKSPFGGMLMILVIVAVVLIVFALNRRTNAIAQAPIRMIYP----DIDKMQ
MURH68PEP      SIVTGFIKFFTNPLGGIFILLIIGGIIFLVVVLNRRNSQFHDAPIKMLYPSVENYAARQA
BOVINEH4PEP    SIVGGFVSFFTNPIGGVTIILLLIVVVFVVFIVSRRTNNMNEAPIKMIYP----NIDKAS
ATELINEH3PEP   GIVTGILNFIKNPLGGMLTFLLVGAIIILVILLVRRTNNMSQAPIRMIYP----DIEKSR
SAIMIRIPEP     GIVTGILNFIKNPLGGMFTFLLIGAVIILVILLVRRTNNMSQAPIRMIYP----DVEKSK
EQH2PEP        SIVSGVISFFKNPFGGMLLIVLIIAGVVVVYLFMTRSRSIYSAPIRMLYP----GVERAA
EQH5PEP        SIVSGVISFLKNPLGAILTIALIVGGIIVLYLFITRSRTVYQAPIRMLYP----EVDRAP
ALCELPEP       SIVSGIINFIKNPFGGMLLFGLIAAVVITVILLNRKAKRFAQNPVQMIYP----DIKTIT
EBVPEP         SLVSGFISFFKNPFGGMLILVLVAGVVILVISLTRRTRQMSQQPVQMLYP----GIDELA

HHV8PEP        PP------SGGAPTREEIKNILLGMHQLQQ----ERQKADDLKKSTPSVFQRTANGLR
RHESRHADPEP    P-------SGGKVDQEQIKNILAGMHQLQQ----EERRRLDEQQRSAPSLFRRASDGLK
MURH68PEP      PPPYSA---SPPAIDKEEIKRILLGMHQVHQ----EEKEAQKQLTNSGPTLWQKATGFLR
BOVINEH4PEP    EQE-----NIQPLPGEEIKRILLGMHQLQQ----SEHGKSEEEASHKPGLFQLLGDGLQ
ATELINEH3PEP   S-------SVTPTEPEVIKQILLGMHNMQQ----EEYKKREEHKASQPSFLKRATDAFL
SAIMIRIPEP     S-------TVTPMEPETIKQILLGMHNMQQ----EAYKKKEEQRAARPSIFRQAAETFL
EQH2PEP        QEP-----GAHPVSEDQIRNILMGMHQFQQRQRAEEEARREEEVKGKRTLFEVIRDSAT
EQH5PEP        QQ------NVQPIPEDQVRSILLAMHQFQQQQQQQQQQEEHTQ-RRSIFDTIRESTS
ALCELPEP       SQREEL---QVDPISKHELDRIMLAMHDYHASK--QPESKQDEEQGSTTSPADWLNKAK
EBVPEP         QQHASGEGPGINPISKTELQAIMLALHEQNQ------EQKRAAQRAAGPSVASRALQAAR
```

Figure 2

```
ATGGCAGGTA GCTTAAAACT TAGGGGATCT GTTCTAGCAC TGTGGTACCT GTATCAGGTG   60
GCTCTTTATT CACTTAGTAT AGCAGAGACC GGTGTAACCT CACCTCCAAA TACAGCGACC  120
TGGTCTACTG AATCGCCGCT AACAGGTCAC TATGGAACAC ACGATTCAAG CCATGGTGAA  180
AGAGGAAACA ACGAAACAG AGATTCAGAA GAGCAAAATA AAAACATTTA TGGATCGCCT  240
TCTACGTTTC CTTACAGAGT ATGCAGTGCC TCCGGAGTTG GAGATGTCTT TAGATTTCAG  300
ACCGACCATG TGTGTCCCGA TGCCAGTGAT ATGGTACACA GTGAGGGGAT TCTACTAATT  360
TACAAACAGA ACATTATTCC ATTTATGTTT AGAGTTAGGA AATATAGAAA AGTTGTTACA  420
ACAAGTACTG TCTACAATGG TATTTATTCT GACTCTATTA CCAACCAACA TACTTTCTAT  480
AAATCAATCG AACCTTGGGA GACAGAAAAG ATGGACACAA TATATCAGTG TTTTAATTCT  540
TTAAGACTAA ACACAGGTGG AAATCTGCTT ACTTATGTAG ATAGAGATGA TATAAATATG  600
ACAGTGTTTC TGCAACCTGT TGACGGTGTG ACGCCCGATG TGAAGAGGTA TGGCAGTCAA  660
CCAGAGCTGT ACCTTGAACC TGGCTGGTTT TGGGGTAGTT ATAGAAGACG AACTACAGTG  720
AACTGTGAAC TAATGGACAT GTTTGCAAGA TCAAATCCTC CATTTGATTT CTTTGTTACA  780
GCTACAGGTG ATACGGTGGA AATGTCTCCA TTTTGGAGTG GTGAAGATGA TCATGAAAAT  840
AAGATGCACG AGAAGCCATG GTTTGTTAGT GTGATAAATA ACTACAAGGT GGTGGACTAT  900
CAAAACAGAG GGACTGTACC CCTTGGAAAA ACAAGGATAT TTCTAGATAG GAAGAGTAT  960
ACATTATCTT GGGAAAAGCA TCTAAAAAAT ATGTCATATT GTCCACTAAC ATTATGGAAA 1020
GCATTTTACA ATGGAATCCA GACGGAGCAT TCAGGCTCAT ATCATTTGT AGCCAATGAC 1080
ATCACAGCGT CATTCACAAC TAGTAAAGAA GACATGAAAG AGTTCAATAC GACATATCAT 1140
TGTCTCAACG AGGAAATAAA GGCAGAAATA GAGAAGAAAT ATGCAAAAGT AAACTCAACT 1200
CACTCTAAAT ATGGAGATCT GAAATACTTT AAAACAGATG GGGGTCTCTA TTTAGTCTGG 1260
CAACCTCTTA TTCAAAACAG GCTTCTTGAT GCTAAGAACA AACTGAACAA TGAGACTTAT 1320
TCCAGGAGAT CACGACGTCA GGCAGAATCT ACTACTGACC CAATGATGGA GATGACTGGA 1380
AATGGAGCAG GTGGAGAATA TAGCAGTGAA AATTCAATCA CGGTGGCGCA GGTGCAGTAT 1440
GCCTATGACA ATCTTCGTAT CAGAATAAAT AACATTTTGG AAGATTTGTC AAAGGCATGG 1500
TGTCGTGAGC AGCATAGAGC TGCTCTGGTG TGGAATGAGC TCAGCAAGAT TAATCCCACA 1560
AGCGTCATGA GCATGATTTA CAATAGACCC GTATCAGCCA AAGAATAGG AGATGTCATT 1620
TCAGTCTCTA ACTGTATTGT GGTAGACCAA ACCAGTGTCT CATTACATAA AAGTCTCAGG 1680
CTTCTCAGTG CATCGGATGA AAAGTGCTTC TCTAGACCTC CAGTGACATT TAAGTTTATG 1740
AATGACAGTA CTATTTACAA AGGGCAACTA GGAGTCAATA ATGAGATTCT CTTAACCACA 1800
ACATACCTTG AAACATGTCA GGAAAACACT GAGTATTACT TCAGGCAAA GACAGACATG 1860
TACATTTACA AAAACTATGA GCATTTGAAG ACTGTGCCTT TATCTTCGAT CACCACACTA 1920
GATACATTTA TAGCCCTTAA TTTTACACTA TTGGAGAATG TTGACTTTAA AGTCATTGAA 1980
CTTTATACCA GGGACGAGAA GAGGCTTAGT AATGTCTTTG ACATTGAAAC AATGTTTAGG 2040
GAATATAACT ACTATGCTCA GAGGGTCAGT GGCCTCAGAA AGGATTTGCT GGATCTAAGC 2100
ACCAATAGAA ATCAATTTGT GGATGCATTT GGTAGTCTTA TGGATGATTT GGGTGCTGTT 2160
GGGCAGACAG TTGTAAATGC TGTAAGTGGT GTGGCTACGC TGTTTAGCTC AATTGTAACA 2220
GGATTATTA ATTCATTAA AAACCCATTT GGTGGAATGT TAATGATTAT TGTTGTTATT 2280
GGTGTGCTAT TTGCCATCTA CTTTCTGACC AAAAAGACGA AGATATATGA GACGGCACCG 2340
ATTAAGATGA TTTATCCTGA AATTGACAAG CTGAAAGAAC GTGAGGGAAA ATCAGAAATA 2400
GCACCAATCA GTGAAGAAGA GCTGGAGAGA ATTGTACTTG CTATGCACAT CCATCAACAA 2460
AATTCACATA TGGAAACAAA AACAAGGAAG GATCCCAAAG ACAGCATATT AACAAGGGCA 2520
CAAAATATGC TACGCAAAAG ATCAGGATAT TCTAATTTAA AAAATGCTGA ATCTGTGGAG 2580
ATGTTAAACA CTTTATAA                                               2598
```

Figure 3

```
MAGSLKLRGS  VLALWYLYQV  ALYSLSIAET  GVTSPPNTAT  WSTESPLTGH         50
YGTHDSSHGE  RGNNENRDSE  EQNKNIYGSP  STFPYRVCSA  SGVGDVFRFQ        100
TDHVCPDASD  MVHSEGILLI  YKQNIIPFMF  RVRKYRKVVT  TSTVYNGIYS        150
DSITNQHTFY  KSIEPWETEK  MDTIYQCFNS  LRLNTGGNLL  TYVDRDDINM        200
TVFLQPVDGV  TPDVKRYGSQ  PELYLEPGWF  WGSYRRRTTV  NCELMDMFAR        250
SNPPFDFFVT  ATGDTVEMSP  FWSGEDDHEN  KMHEKPWFVS  VINNYKVVDY        300
QNRGTVPLGK  TRIFLDREEY  TLSWEKHLKN  MSYCPLTLWK  AFYNGIQTEH        350
SGSYHFVAND  ITASFTTSKE  DMKEFNTTYH  CLNEEIKAEI  EKKYAKVNST        400
HSKYGDLKYF  KTDGGLYLVW  QPLIQNRLLD  AKNKLNNETY  SRRSRRQAES        450
TTDPMMEMTG  NGAGGEYSSE  NSITVAQVQY  AYDNLRIRIN  NILEDLSKAW        500
CREQHRAALV  WNELSKINPT  SVMSMIYNRP  VSAKRIGDVI  SVSNCIVVDQ        550
TSVSLHKSLR  LLSASDEKCF  SRPPVTFKFM  NDSTIYKGQL  GVNNEILLTT        600
TYLETCQENT  EYYFQAKTDM  YIYKNYEHLK  TVPLSSITTL  DTFIALNFTL        650
LENVDFKVIE  LYTRDEKRLS  NVFDIETMFR  EYNYYAQRVS  GLRKDLLDLS        700
TNRNQFVDAF  GSLMDDLGAV  GQTVVNAVSG  VATLFSSIVT  GFINFIKNPF        750
GGMLMIIVVI  GVLFAIYFLT  KKTKIYETAP  IKMIYPEIDK  LKEREGKSEI        800
APISEEELER  IVLAMHIHQQ  NSHMETKTRK  DPKDSILTRA  QNMLRKRSGY        850
SNLKNAESVE  MLNTL                                                 865
```

Figure 4

```
pGHV-gpB DNA.txt       ---------- ---------- -----AATCT TCGTATCAGA ATAAATAACA   25
pGHV1 DNA.641-1300)    CGCCGCCGTC CGGCTCCACG GTGGTGCGGC TGGAGCCCGA GCAGGC--CT  688
                                                 T G   C GA   A        C pGHV-gpB DNA.txt       TTTTGGAAGA TTTGTCAAAG GCATGGTGTC GTGAGCAGCA TAGAGCTGCT   75
pGHV1 DNA.(641-1300)   GCCCCGAGTA CTCG-CAGGG GCGCAACTTC ACGGAGGGGA TCGCCGTGCT  737
                            GA A  T G CA  G GC       TC   G     GA T G   TGCT pGHV-gpB DNA.txt       CTGGTGTGGA ATGAGCTCAG CAAGATTAAT CCCACAAGCG TCATGAGCAT  125
pGHV1 DNA.(641-1300)   CT----T-CA AGGAGAACAT C--G-CC--C CGCACAAGT- TCAAGGCCCA  776
                       CT     T  A A GAG  CA   C   G       C CACAAG   TCA G  C pGHV-gpB DNA.txt       GATTTACAAT -AGACCCGTA TCAGC-CAAA AGAATAG-GA GATGTCATTT  172
pGHV1 DNA.(641-1300)   CATCTACTAC AAGAACGTCA TCGTCACGAC CGTGTGGTCC GGGAGCACGT  826
                         AT TAC A   AGA C    A TC   C A   G TG    G    CA T pGHV-gpB DNA.txt       CAGTCTCTAA C-TGTATTG- -TGGTAGACC AAACCAGTGT CTCATTACAT  219
pGHV1 DNA.(641-1300)   ACGCGGCCAT CACGAACCGC TTCACAGACC GCGTGCCCGT CCCCGTGCAG  876
                           G   CA  C  G AG    T   AGACC          GT C C T CA pGHV-gpB DNA.txt       AAAAGTCTCA GGCTTCTCAG TGCATCGGAT GAAAAGTGCT TCTCTAGACC  269
pGHV1 DNA.(641-1300)   GAGA-TCACG GACGTGATCG ACCGCCG--C GGCAAGTGCG TCTCCA-AGG  922
                        A  A TC C    C T   G  C  CG     G  AAGTGC  TCTC A  A pGHV-gpB DNA.txt       TCCAGTGACA T--TTAA-GT TTATGA-ATG ACAGTACT-A TTTACAAAGG  314
pGHV1 DNA.(641-1300)   CCGAGT-ACG TGCGCAACAA CCACAAGGTG ACCGCCTTCG ACCGCGACGA  971
                         C AGT AC  T     AA     A A TG AC G  T        C AG pGHV-gpB DNA.txt       GCAACTAG-- GAGTCAATAA TGAGATTCT- ----CTTAAC ---CACAACA  354
pGHV1 DNA.(641-1300)   CAACCCCGTC GAGGTGGACC TGCGCCCCTC GCGCCTGAAC GCGCTCGGCA 1021
                       G  A C     GAG        TG G  CT       CT AAC     C   C pGHV-gpB DNA.txt       TAC-C--TTG AAACA-TGTC -AGGAAA--- ACACTGAGTA TTAC-TTTCA  395
pGHV1 DNA.(641-1300)   CCCGCGGCTG GCACACCACC AACGACACCT ACACCAAGAT CGGCGCCGCG 1071
                         C   TG   ACA    C   A GA A    ACAC  AG    C      C pGHV-gpB DNA.txt       GGCAAAGACA GACATGTACA TTTACAAAAA CT--AT---- GAGCATTTGA  439
pGHV1 DNA.(641-1300)   GGCTTCTAC- CACACGGGCA CCTCCGTCAA CTGCATCGTC GAGGAGGTGG 1120
                       GGC    AC  ACA G  CA    T C   AA CT AT      GAG A  TG pGHV-gpB DNA.txt       AGAC------ --TGTGCCTT TA-----TCT TCGATCACCA CACTAGATAC  476
pGHV1 DNA.(641-1300)   AGGCGCGCTC CGTGTACCCC TACGACTCCT TCGCCCTGTC CACGGGGGAC 1170
                       AG C         TGT CC   TA     CT TCG C      CAC G AC pGHV-gpB DNA.txt       ATT---TATA GCCCTTAATT TTAC--ACTA TTGGAGAATG TTGACTTTAA  521
pGHV1 DNA.(641-1300)   ATTGTGTACA TGTCCCCCTT CTACGGCCTG CGCGAGGGGG CCCACGGGGA 1220
                       ATT   TA A   C     TT  TAC  T    G GAG  G   AC    A pGHV-gpB DNA.txt       AGTCATTGAA CTTTATACCA GGG----ACG AG-AAGAGGC TTAGTA--AT  564
pGHV1 DNA.(641-1300)   GCACATCG-G CTACGCGCCC GGGCGCTTCC AGCAGGTGGA GCACTACTAC 1269
                           CAT G    CT    CC  GGG    C  AG   G  GG   A TA  A pGHV-gpB DNA.txt       GTCTTTGACA TTGAAACAAT G--------- --  585
pGHV1 DNA.(641-1300)   CCCATCGAC- CTGGACTCGC GCCTCCGCGC CT 1300
                         C T GAC    TG A        G
```

Figure 5

```
pGHV-gpB prot        -------------------- ----------N LRI------- ----------      4
PGHV1Prot.(491-850)  PAAPAAARRA RRSPGPAGTP EPPAVNGTGH LRITTGSAEF ARLQFTYDHI    540
                                                     LRI pGHV-gpB prot        --RINNILED LSKAWCREQH RAALVWNELS KINPTSVMSM IYNRPVSAKR     52
PGHV1Prot.(491-850)  QAHVNDMLGR IAAAWCELQN KDRTLWSEMS RLNPSAVATA ALGQRVSARM    590
                       N L        AWC Q         WES    NP V        VSA pGHV-gpB prot        IGDVISVSNC IVVDQTSVSL HKSLRLLSAS DEKCFSRPPV TFKFMNDSTI    102
PGHV1Prot.(491-850)  LGDVMAISRC VEV-RGGVYV QNSMR-VPGE RGTCYSRPLV TFE-HNGTGV    637
                      GDV  S C   V     V     S R         C SRP V TF   N pGHV-gpB prot        YKGQLGVNNE ILLTTTYLET CQENTEYYFQ AKTDMYIYKN YEHLKTVPLS    152
PGHV1Prot.(491-850)  IEGQLGDDNE LLISRDLIEP CTGNHRRYFK LGSGYVYYED YNYVRMVEVP    687
                       GQLG NE   L      E    C N  YF             Y  Y     V pGHV-gpB prot        SITTLDTFIA LNFTLLENVD FKVIELYTRD E--------- ----KR----    185
PGHV1Prot.(491-850)  --ETISTRVT LNLTLLEDRE FLPLEVYTRE ELADTGLLDY SEIQRRNQLH    735
                         T      LN TLLE     F   E YTR  E                R pGHV-gpB prot        ---------- ---------- ---------- ---------- ----------    185
PGHV1Prot.(491-850)  ALKFYDIDRV VKVDHNVVLL RGIANFFQGL GDVGAAVGKV VLGATGAVIS    785 pGHV-gpB prot        --------LS NVF------- ---------- ---------- ----------    190
PGHV1Prot.(491-850)  AVGGMVSFLS NPFGALAIGL LVLAGLVAAF LAYRHISRLR RNPMKALYPV    835
                            LS N F pGHV-gpB prot        --------DI E--TM                                          195
PGHV1Prot.(491-850)  TTKTLKEDGV DEGDV                                          850
```

Figure 6

```
pGHV-gpB DNA.txt   ----------  ----------  ----------  ----------  ----------
pGHV2 DNA.txt      CCAGCATAAT  GATAGCCAAT  AATCTGTGTT  ACTCTACCCT  GATCTTAAAT    50 pGHV-gpB DNA.txt   ----------  ----------  ----------  ----------  -----AATCT     5
pGHV2 DNA.txt      GACGAGGACG  TGACGGGGAT  CGACGAGAAA  GATATTCTGA  CGGTGCATGT   100
                                                                   AT T pGHV-gpB DNA.txt   TCGTATCAGA  ATA-AAT-AA  CATTTTGGAA  GATTTGTCAA  AGGCATGGTG    53
pGHV2 DNA.txt      --AAACAAGA  ATACCGTGTA  CAGGTTCG-T  TAGGAG-CAG  CGTCAGGGAG   146
                     A  AGA ATA    T  A  CA  TT  G     A   G CA    G CA GG  G pGHV-gpB DNA.txt   TC-GTGAGCA  GCATAGAGCT  GCTCTGGTGT  GGAATGAGCT  CAGCAAGATT   102
pGHV2 DNA.txt      TCTATACTCG  GCAC---GCT  GCT---GTCT  AG-ATG-GCT  CAGGAAGAGA   188
                   TC  T   C   GCA    GCT  GCT   GT T   G ATG GCT  CAG AAGA pGHV-gpB DNA.txt   AATCCCACAA  GCG-TCATGA  GCATGATTTA  CAAT-AGACC  CGTAT-CAGC   149
pGHV2 DNA.txt      AA----GGAA  GTGAAGGCGC  GCATGAAACG  CTGTGAGGAC  CCTATGTTGG   234
                   AA     AA  G G     G   GCATGA      C  T AG  C  C TAT    T pGHV-gpB DNA.txt   CAAAAGAATA  GGAGATGTCA  TTTCAGTCTC  TAACTGTATT  GTGGTAGACC   199
pGHV2 DNA.txt      C-ACTG-AT-  --ACTTGACA  -AGCAGCAGC  TTGC--CCTC  AAGGT-GAC-   274
                   C A  G AT    A  TG CA   CAG    C T    C     T     GGT GAC pGHV-gpB DNA.txt   AAACCAGTGT  CTCATTACAT  AAAAGTCTCA  GGCTTCTCAG  TGCATCGGAT   249
pGHV2 DNA.txt      -GTGCAATGC  GTT-TTAC--  ---GGCTTCA  CGGGAGCC-G  TGCA-CGG-T   314
                    CA TG      T   TTAC        G TCA  G       C G  TGCA CGG  T pGHV-gpB DNA.txt   GAAAAGTGCT  TCTCTAGACC  TCCAGTGACA  TTTAAGTTTA  TGAATGACAG   299
pGHV2 DNA.txt      CTGCTGC-CG  TGTCT--CCC  TCTAGCGGCG  TCCA---TCA  CCAGC-ATAG   357
                      G   C    T TCT   CC  TC AG G C   T  A   T A    A  A AG pGHV-gpB DNA.txt   TACTATTTAC  AAAGGGCAAC  TAGGAGTCAA  TAATGAGATT  CTCTTAACCA   349
pGHV2 DNA.txt      GGC--GGGAC  A---TGC--T  TAGG---CA-  -GACGAG-TG  ACTTTATCAA   394
                     C    AC A     GC     TAGG   CA      A GAG T     TTA C A pGHV-gpB DNA.txt   CAACATACCT  TGAAACATGT  CAGGAAAACA  CTGAGTATTA  CTTTCAGGCA   399
pGHV2 DNA.txt      CAATGT-CCT  T-----TCGT  CTAGAGAATA  CG--------  ----------   420
                   CAA  T CCT  T        GT  C  GA AA A  C pGHV-gpB DNA.txt   AAGACAGACA  TGTACATTTA  CAAAAACTAT  GAGCATTTGA  AGACTGTGCC   449
pGHV2 DNA.txt      ----------  ----------  ----------  ----------  ----------   420 pGHV-gpB DNA.txt   TTTATCTTCG  ATCACCACAC  TAGATACATT  TATAGCCCTT  AATTTTACAC   499
pGHV2 DNA.txt      ----------  ----------  ----------  ----------  ----------   420 pGHV-gpB DNA.txt   TATTGGAGAA  TGTTGACTTT  AAAGTCATTG  AACTTTATAC  CAGGGACGAG   549
pGHV2 DNA.txt      ----------  ----------  ----------  ----------  ----------   420 pGHV-gpB DNA.txt   AAGAGGCTTA  GTAATGTCTT  TGACATTGAA  ACAATG                    585
pGHV2 DNA.txt      ----------  ----------  ----------  ------                    420
```

Figure 7

```
pGHV-gpB prot    NLRIRINNIL  EDLSKAWCRE  QHRAALVWNE  LSKINPTSVM  SMIYNRPVSA      50
pGHV2 prot.txt   S--IMIANNL  -------C--  --YSTLI---  LNDEDVTG--  -------IDE      25
                    I I N L          C      L         L    T pGHV-gpB prot    KRIGDVISVS  NCIVVDQTSV  SLHKSLRLLS  ASDEKCFSRP  PVTFKFMNDS     100
pGHV2 prot.txt   K---DILTVH  ----VMKNTV  ----------  ----------  ---YRFVRSS      45
                 K    D  V        V  V                                F   S pGHV-gpB prot    ---TIYKGQL  GV-NNEILLT  TTYLETCQEN  TEYYFQAKTD  MYI---YKN-     142
pGHV2 prot.txt   VRESILGTLL  SRWLRKRKEV  KARMKRCEDP  MLALILDKQQ  LALKVTCNAF      95
                      I  L                      C              K pGHV-gpB prot    YEHLKTVP--  LSSITTLDTF  IALNFTLL-E  NVDFKVIELY  TRD---EK-R     185
pGHV2 prot.txt   YGFTGAVHGL  LPCLPLAASI  TSIGRDMLRQ  TSDFINNVLS  SREYVSEKFS     145
                 Y     V     L                L      DF    L     R    EK pGHV-gpB prot       LSNV-F--DI  ETM-             195
pGHV2 prot.txt      LSDGDFQGDF  SPEC             159
                    LS   F  D
```

Figure 8

```
pGHV-gpB DNA        AATCTTCGTA TCAGAATAAA TAACATTTTG GAAGATTTGT CAAAGGCATG    50
AF118399 DNA.txt    ---------- ---------- ---------- ---------- ---------- pGHV-gpB DNA        GTGTCGTGAG CAGCATAGAG CTGCTCTGGT GTGGAATGAG CTCAGCAAGA   100
AF118399 DNA.txt    ---------- ---------- ---------- ---------- ---------- pGHV-gpB DNA        TTAATCCCAC AAGCGTCATG AGCATGATTT ACAATAGACC CGTATCAGCC   150
AF118399 DNA.txt    ---------- ---------- ---------- ---------- ---------- pGHV-gpB DNA        AAAAGAATAG GAGATGTCAT TTCAGTCTCT AACTGTATTG TGGTAGACCA   200
AF118399 DNA.txt    ---------- ---------- ---------- ---------- ---------- pGHV-gpB DNA        AACCAGTGTC TCATTACATA AAAGTCTCAG GCTTCTCAGT GCATCGGATG   250
AF118399 DNA.txt    ---------- ---------- ---------- ---------- ---------- pGHV-gpB DNA        AAAAGTGCTT CTCTAGACCT CCAGTGACAT TTAAGTTTAT GAATGACAGT   300
AF118399 DNA.txt    ---------- ---------- ---------- ------TAAT CTATGTCACT    14
                                                        T AT     ATG CA T pGHV-gpB DNA        ACTATTTACA AAGGGCAACT AGGA-GTCAA TAATGAGATT CTCTTAACCA   349
AF118399 DNA.txt    -CTACCC-TA ATCCATCATG AAGACCTGCA TAAATATCCT CAATTAAAGG    62
                     CTA   A  A      A    A GA  T A TAA  A   T A  TTAA pGHV-gpB DNA        CAACATACCT TGAAACATGT CAGGAAAACA CTGAGTATTA CTTTCAGGCA   399
AF118399 DNA.txt    AGGAGGATTA TGAAACAT-- ---------- ---------- -TTT------    83
                      A         TGAAACAT                              TTT pGHV-gpB DNA        AAGACAGACA TGTACATTTA CAAAAACTAT GAGCATTTGA AGACTGTGCC   449
AF118399 DNA.txt    ---------- TG---ATT-- ---------- -AG---TT-- ---CTG----    95
                                TG   ATT                  AG   TT      CTG pGHV-gpB DNA        TTTATCTTCG ATCACCACAC TAGATACATT TATAGCCCTT AATTTTACAC   499
AF118399 DNA.txt    ---------- ---------- ---------- ----GTCC-- ----------    99
                                                        GTCC pGHV-gpB DNA        TATTGGAGAA TGTTGACTTT ------AAAG TCAT-T--GA A---CTT----  534
AF118399 DNA.txt    ---------- TGTTCACTTT GTAAAAAAAC ACATATCAGA ATCTCTTCTG   139
                                TGTT ACTTT       AAA    CAT T  GA A    CTT pGHV-gpB DNA        --TA------ -TAC--CA-- G--GG--ACG AGA------- --AG--AGG-   555
AF118399 DNA.txt    TCTAACCTGC TTACAACATG GCTGGCTAAG AGAAAAATGA TCAGAAGGA    189
                      TA         TAC CA    G  GG  A G AGA            AG   AGG pGHV-gpB DNA        CTTAGTA--A TGT-CT--TT GACA-TTGA- AACAATG--- ----------   585
AF118399 DNA.txt    ATTAGCAGCA TGTGCTGACC CAAAGCTCAG GACAAT-TTT AGATAAACAG   238
                     TTAG A  A TGT CT     A  T    A  ACAAT pGHV-gpB DNA        ---------- ---------- ---------- ---------- ----------   585
AF118399 DNA.txt    CAGCTTGCAA TTAAGGTGAC ATGCAATGCT GTGTATGGGT TCACTGGTGT   288 pGHV-gpB DNA        ---------- ---------- ---------- ---------- ----------   585
AF118399 DNA.txt    TGCATCTGGT ATGCTGCCCT GTCTCAAGAT TGCAGAGACC ATAACTATGC   338 pGHV-gpB DNA        ---------- ---------- ---------- ---------- ----------   585
AF118399 DNA.txt    AAGGAAGGGC CATGTTGGAA AAGACAAAAG TATTTGTAGA GAATTTAAGT   388 pGHV-gpB DNA        ---------- ---------- ---------- ---------- ----------   585
AF118399 DNA.txt    CATGAGGATC TCCATTCCAT CTGTAAGGTT GGCTTTATGC CTCAGTCACC   438 pGHV-gpB DNA        ---------- ---------- ---------            585
AF118399 DNA.txt    AAACAGCATT GATAAACCCT TCAAGGTG             466
```

Figure 9

```
pGHV-gpB DNA     ---------- ---------- ---------- ---------- ----------
AF118401 DNA.txt GAGGACCTGC ATAAGTATCC TCAATTAAAG GAGGATGATT ATGAAACATT   50 pGHV-gpB DNA     ---------- ---------- ---------- ---AATCTTC GTATCAGAAT   17
AF118401 DNA.txt TTTGATTAGT TCTGGCCCTG TTCACTTTGT AAAAAAACAC ATATCAGAAT  100
                                                 AA        C  TATCAGAAT pGHV-gpB DNA     AAATAACATT TTGGAAGATT TGTCAAAGGC ATGGTGTCGT GAGCAGCATA   67
AF118401 DNA.txt ------C-TC TT-------- ---------- ---------- ----------  105
                       C T  TT pGHV-gpB DNA     GAGCTGCTCT GGTGTGGAAT GAGCTCAGCA AGATTAATCC CACAAGCGTC  117
AF118401 DNA.txt ---CTG-TC- ------GAA- ---CTT---- -G------CT CACAA----C  125
                    CTG TC        GAA      CT     G       C  CACAA    C pGHV-gpB DNA     ATGAGCATGA TTTACAATAG ACCCGTATCA GCCAAAAGAA ------T---  158
AF118401 DNA.txt ATG-GC-TG- ---------- ---------- GCCAAGAGAA AAATGATCAG  152
                 ATG GC TG                                            T pGHV-gpB DNA     --AGG----- --AG-ATGT- ---------- --------CA --TTT-----  172
AF118401 DNA.txt AAAGGAATTG ACAGCATGTG CTGATCCAAA GCTCAGGACA ATTTTAGATA  202
                   AGG          AG ATGT                         CA   TTT pGHV-gpB DNA     -----CAGTC T----CTA-- ---AC-TGTA TTG-TG-GTA --GA-CCA--  200
AF118401 DNA.txt AACAGCAGCT TGCAATTAAG GTGACATGCA ATGCTGTGTA TGGATTCACT  252
                      CAG    T    TA       AC TG A  TG TG GTA    GA  CA pGHV-gpB DNA     --------A- -----AC-CA G---TGTCTC A--------- ------TTAC  217
AF118401 DNA.txt GGTGTTGCAT CTGGTATGCT GCCATGTCTC AAGATTGCAG AGACCATCAC  302
                         A        A  C  G   TGTCTC A                 TCAC pGHV-gpB DNA     ---------- ---------- --------AT AAAAGT--CT -CAG-GCTTC  235
AF118401 DNA.txt TATGCAAGGA AGGGCCATGT TGGAAAAGAC AAAAGTATTT GTAGAGAATC  352
                                                A  AAAAGT  T  AG G  TC pGHV-gpB DNA     TCAG---TGC A-----TCGGA T-GAAAAGT- -GCTT--CTC TAGACCTCCA  273
AF118401 DNA.txt TGAGTCATGA AGATCTCCGT TCCATATGTA AGGTTGGCTC TATACCTC-A  401
                 T AG   TGC A      TC G  T     A GT   G TT  CTC  TA ACCTC A pGHV-gpB DNA     GTGACATTTA AGTTTATGAA TGACAGTACT ATTTACAAAG GGCAACTAGG  323
AF118401 DNA.txt GT--CA-TCA A-----ACG-- TG-------- -TTT------ ----------  417
                 GT  CA T A  A      A G    TG            TTT pGHV-gpB DNA     AGTCAATAAT GAGATTCTCT TAACCACAAC ATACCTTGAA ACATGTCAGG  373
AF118401 DNA.txt -G---ATAAA ---------- ---------- ---------- ----------  423
                  G    ATAA pGHV-gpB DNA     AAAACACTGA GTATTACTTT CAGGCAAAGA CAGACATGTA CATTTACAAA  423
AF118401 DNA.txt ---------- ---------- ---------- ---------- ----------  423 pGHV-gpB DNA     AACTATGAGC ATTTGAAGAC TGTGCCTTTA TCTTCGATCA CCACACTAGA  473
AF118401 DNA.txt ---------- ---------- ---------- ---------- ----------  423 pGHV-gpB DNA     TACATTTATA GCCCTTAATT TTACACTATT GGAGAATGTT GACTTTAAAG  523
AF118401 DNA.txt ---------- ---------- ---------- ---------- ----------  423 pGHV-gpB DNA     TCATTGAACT TTATACCAGG GACGAGAAGA GGCTTAGTAA TGTCTTTGAC  573
AF118401 DNA.txt ---------- ---------- ---------- ---------- ----------  423 pGHV-gpB DNA     ATTGAAACAA TG   585
AF118401 DNA.txt ---------- --   423
```

Figure 10

```
Query:    1970  aagtcattgaactttataccagggacgagaagaggcttagtaatgtctttgacattgaaa  2029
                ||||  ||  |||||  ||     ||  ||  ||||||||||   |  ||   ||    ||  ||    |||||  ||   ||  |
Sbjct:   18669  aagtaatagaactatactctagagaagagaagaggatgagcactgcatttgatatagaga 18728

Query:    2030  caatgtttagggaatataactactatgctcagagggtcagtggcctcagaaaggatttgc 2089
                |  ||||||||  |||||  ||||||||     |  |||||||||||  ||||||    |     |   |||  |||
Sbjct:   18729  ccatgtttagagaatacaactactacacacagagggtcactggcctgcgggagggacttga 18788

Query:    2090  tggatctaagcaccaatagaaatcaatttgtggatgcatttggtagtcttatggatgatt 2149
                ||  |||        ||  ||   |||||||||||||||||  |||||  ||!||  ||  ||  |||||  ||  |
Sbjct:   18789  cagacctagctacaaacagaaatcaatttgtagatgcctttggcagcctcatggacgact 18848

Query:    2150  tgggtgctgttgggcagacagttgtaaatgctgtaagtggtgtggctacgctgtttagct 2209
                ||||   |    ||  |||    |   ||    |     ||||||||||  ||    |||||||  ||    ||    ||   ||||
Sbjct:   18849  tggggtcgtggggaaaacggtgttgaatgctgtgagcagtgtggccacactcttcagct 18908

Query:    2210  caattgtaacaggattttattaatttcattaaaaacccatttggtggaatgtt 2261
                |  ||    ||      ||||        |   ||   |||||||||||||||||||||  |||||   |||||||
Sbjct:   18909  ctatagtctcagggatcatcaatttcattaaaaacccctttgggggaatgtt 18960
```

Score = 91.1 bits (47), Expect = 7e-16
Identities = 117/152 (76%), Positives = 117/152 (76%)

```
Query:    1498  tggtgtcgtgagcagcatagagctgctctggtgtggaatgagctcagcaagattaatccc 1557
                |||||  |||||||||||||  ||||   ||||    ||||||||  ||||| |||||  ||  ||  ||
Sbjct:   18194  tggtgccgtgagcagcaccgagcctctctcatgtggaacgagctaagcaaaatcaaccct 18253

Query:    1558  acaagcgtcatgagcatgatttacaatagacccgtatcagccaaaagaataggagatgtc 1617
                ||  ||  ||  |||||||     ||  |||         |  ||  ||||||  ||||||||||||  |||||||
Sbjct:   18254  accagtgtgatgagctctatatacgggcggccagtatctgccaaaagaattggagatgtg 18313

Query:    1618  atttcagtctctaactgtattgtggtagacca 1649
                ||  ||  ||||||  |||||  |  |||||  |||||
Sbjct:   18314  atatctgtctctcactgtgtggtggtggacca 18345
```

Figure 11(a)

```
gi|2337975 (AF005370) glycoprotein B [Alcelaphine herpesvirus 1]
         Length = 854

Score = 953 bits (2437), Expect = 0.0
  Identities = 463/804 (57%), Positives = 589/804 (72%), Gaps = 26/804 (3%)

Query:  74  KNIYGSPSTFPYRVCSASGVGDVFRFQTDHVCPDASDMVHSEGILLIYKQNIIPFMFRVR  133
            K I+  PS FP+RVCSAS +GD+FRFQT H CP+   D  H+EGILLI+K+NI+P++F+VR
Sbjct:  55  KGIHSDPSAFPFRVCSASNIGDIFRFQTSHSCPNTKDKEHNEGILLIFKENIVPYVFKVR  114

Query: 134  KYRKVVTTSTVYNGIYSDSITNQHTFYKSIEPWETEKMDTIYQCFNSLRLNTGGNLLTYV  193
            KYRK+VTTST+YNGIY+D++TNQH F KS+  +ET +MDTIYQC+NSL +  GGNLL Y
Sbjct: 115  KYRKIVTTSTIYNGIYADAVTNQHVFSKSVPIYETRRMDTIYQCYNSLDVTVGGNLLVYT  174

Query: 194  DRDDINMTVFLQPVDGVTPDVKRYGSQPELYLEPGWFWGSYRRRTTVNCELMDMFARSNP  253
            D D  NMTV LQPVDG++  V+RY SQPE++ EPGW  G YRRRTTVNCE+    AR+ P
Sbjct: 175  DNDGSNMTVDLQPVDGLSNSVRRYHSQPEIHAEPGWLLGGYRRRTTVNCEVTETDARAVP  234

Query: 254  PFDFFVTATGDTVEMSPFWSGEDDHENKMHEKPWFVSVINNYKVVDYQNRGTVPLGKTRI  313
            PF +F+T GDT+EMSPFWS    +     E   ++V  +Y+VVDY+ RGT P G TRI
Sbjct: 235  PFRYFITNIGDTIEMSPFWSKAWNETEFSGEPDRTLTVAKDYRVVDYKFRGTQPQGHTRI  294

Query: 314  FLDREEYTLSWEKHLKNMSYCPLTLWKAFYNGIQTEHSGSYHFVANDITASFTTSKEDMK  373
            F+D+EEYTLSW + +N+SYC   WK+F N I+TEH  S HFVANDITASF T     +
Sbjct: 295  FVDKEEYTLSWAQQFRNISYCRWAHWKSFDNAIKTEHGKSLHFVANDITASFYTPNTQTR  354

Query: 374  EFNTTYHCLNXXXXXXXXXXXXXXXVNSTHSKYGDLKYFKTDGGLYLVWQPLIQNRLLDAKN  433
            E   + CLN              VN THS G +Y+ T+GGL LVWQPL+Q +LLDAK
Sbjct: 355  EVLGKHVCLNNTIESELKSRLAKVNDTHSPNGTAQYYLTNGGLLLVWQPLVQQKLLDAKG  414

Query: 434  KLN---------NETYSRRSRRQAESTTDPMMEMTGNGAGGEYSSENSITVAQVQYAYDN  484
            L+          T + RSRRQ  S +      +G   Y++E++I + Q+Q+AYD
Sbjct: 415  LLDAVKKQQNTTTTTTTTRSRRQRRSVS--------SGIDDVYTAESTILLTQIQFAYDT  466

Query: 485  LRIRINNILEDLSKAWCREQHRAALVWNELSKINPTSVMSMIYNRPVSAKRIGDVISVSN  544
            LR +INN+LE+LS+AWCREQHRA+L+WNELSKINPTSVMS IY RPVSAKRIGDVISVS+
Sbjct: 467  LRAQINNVLEELSRAWCREQHRASLMWNELSKINPTSVMSSIYGRPVSAKRIGDVISVSH  526

Query: 545  CIVVDQTSVSLHKSLRLLSA-SDEKCFSRPPVTFKFMNDSTIYKGQLGVNNEILLTTTYL  603
            C+VVDQ SVSLH+S+R+      +C+SRPPVTFKF+NDS +YKGQLGVNNEILLTTT +
Sbjct: 527  CVVVDQDSVSLHRSMRVPGRDKTHECYSRPPVTFKFINDSHLYKGQLGVNNEILLTTTAV  586

Query: 604  ETCQENTEYYFQAKTDMYIYKNYEHLKTVPLSSITTLDTFIALNFTLLENVDFKVIELYT  663
            E C ENTE+YFQ   +MY YKNY H+KT+P+   TLDTF+ LN TL+EN+DF+VIELY+
Sbjct: 587  EICHENTEHYFQGGNNMYFYKNYRHVKTMPVGDVATLDTFMVLNLTLVENIDFQVIELYS  646

Query: 664  RDEKRLSNVFDIETMFREYNYYAQRVSGLRKDLLDLSTNRNQFVDAFGSLMDDLGAVGQT  723
            R+EKR+S  FDIETMFREYNYY QRV+GLR+DL DL+TNRNQFVDAFGSLMDDLG VG+T
Sbjct: 647  REEKRMSTAFDIETMFREYNYYTQRVTGLRRDLTDLATNRNQFVDAFGSLMDDLGVVGKT  706
```

Figure 11(b)

```
Query:  724 VVNAVSGVATLFSSIVTGFINFIKNPFGGMLMIIVVIGVLFAIYFLTKKTKIYETAPIKM 783
            V+NAVS VATLFSSIV+G INFIKNPFGGML+  ++  V+  +  L +K K    P++M
Sbjct:  707 VLNAVSSVATLFSSIVSGIINFIKNPFGGMLLFGLIAAVVITVILLNRKAKRFAQNPVQM 766

Query:  784 IYPEIDKLKEREGKSEIAPISEEELERIVLAMHIHQQNSHMETK------TRKDPKDSI 836
            IYP+I  +  +  + ++ PIS+ EL+RI+LAMH  +    E+K       T    P D
Sbjct:  767 IYPDIKTITSQREELQVDPISKHELDRIMLAMHDYHASKQPESKQDEEQGSTTSGPAD-W 825

Query:  837 LTRAQNMLRKRSGYSNLKNAESVE 860
            L +A+N+LR+R+GY  LK  +S E
Sbjct:  826 LNKAKNVLRRRAGYKPLKRTDSFE 849
```

GAMMA HERPESVIRUS DNA AND METHODS OF USE

This application is a divisional of U.S. application Ser. No. 09/612,204, filed 7 Jul. 2000, and claims the benefit of U.S. Provisional Application No. 60/168,532, filed 2 Dec. 1999, and U.S. Provisional Application No. 60/142,736, filed 8 Jul. 1999, the disclosures of which are hereby incorporated by reference in their entirety.

FIELD OF THE INVENTION

The present invention relates to newly identified polynucleotides, polypeptides, and fragments thereof encoded by porcine gamma-herpesvirus sequences, and methods of using the porcine gamma-herpesvirus nucleic acids and polypeptides.

BACKGROUND OF THE INVENTION

Organ procurement currently poses one of the major problems in solid organ transplantation, since the number of patients requiring transplants far exceeds the number of organs available. One means of eliminating the shortage of donor organs for allotransplantation is to develop the technologies required to transplant non-human organs into humans, i.e., xenotransplantation. The development of clinical xenotransplantation will also allow for the transplantation of non-human cells and tissues.

A potential problem lies in the fact that human and animal organs may be of very different size, depending on the species serving as donor, and on the possibility of infection due to microorganisms present in the donor tissues and having an ability to infect humans. Consequently, one strain of the domesticated pig, denoted miniature swine (*Sus scrofa*), appears suitable for such transplants because of its similar size to humans (see below). Furthermore, any use of pigs as organ donors in xenotransplantation would obviate problems associated with the consideration of non-human primates as donors. Xenografts from non-human primates, for example, present considerable risk of transmission of pathogens and the consequent development of emerging infections. In addition, several pathogens that cause disease are known to infect both humans and non-human primates, for example, in the transmission of HIV from the chimpanzee to humans. Furthermore, chimpanzees and orangutans, the closest non-human primates phylogenetically, are endangered species and far too rare to be considered for organ transplantation purposes. Baboons are too small to be an appropriate donor for most organ transplants. Even the largest baboons weigh less than 40 kg. In addition, the gestation times and productivity of primates would not allow a commercially significant generation of source animals.

The physiology of many organ systems of pigs has been shown to be highly similar to the human counterparts (Sachs, D. H. (1994) *Veterinary Immunology & Immunopathology* 43:185–191). Thus, the miniature swine offers numerous advantages as potential xenograft donors. They achieve adult weights of approximately 100–150 kg, a size that is more compatible to human weights than that of the domestic pig, which reaches weights of over 500 kg. Through a selective breeding program over the past 20 years, partially inbred, miniature swine have been produced (Sachs et al. (1976) *Transplantation* 22: 559–567; Sachs, D. H. (1992) *In Swine as models in biomedical research*, eds M. Swindle, D. Moody, and L. Phillips, pp. 3–15. Ames Iowa State Univ. Press; Sachs, (1994) *Veterinary Immunology & Immunopathology* 43: 185–191). This breeding program has resulted in herds of animals that are genetically well characterized and inbred at the major histocompatibility complex (MHC). These animals have been used in large animal model studies for many years and have, like their domestic counterparts, very favorable breeding characteristics for being used as donors of organs in xenotransplantation.

A central concern regarding xenotransplantation is the risk of xenosis, infection by organisms transferred with the xenograft into both the transplant recipient and the general population. In particular, "emerging infections" caused by new and previously unknown infectious agents with altered pathogenicity, have to be considered as a potential risk associated with xenotransplantation. The risk of viral infection is increased in transplantation by the presence of factors commonly associated with viral activation, e.g., immune suppression, graft-versus-host disease, graft rejection, viral co-infection, and cytotoxic therapies.

Herpesviruses are the causative agents of many diseases that share a commonality of latency and recurrent infections. Herpesviruses may persist for years in a dormant state and become reactivated after later provocation. While the herpesviruses are widely separated in terms of genomic sequence and proteins, many are similar in terms of virion structure and genome organization. Herpesvirus represents a DNA virus family containing a central icosahedral core of double-stranded DNA. There is a lipoprotein envelope that is trilaminar and 100–200 nm in diameter and a nucleus that is 30–43 nm in diameter. The genome size is large, up to 235 kbp DNA. Based upon the structural and morphological features, the herpesvirus family is divided into three main families: alpha, beta, and gamma. Examples of alpha herpesviruses are herpes simplex and varicella zoster, examples of beta herpesviruses are cytomegalovirus and human herpesvirus 6 while examples of gamma-herpesviruses are Epstein Barr virus and human herpesvirus 8.

Prior to this invention, members of three porcine herpesvirus families had been identified, namely of the alpha, beta, and gamma-herpesvirus families. Suid herpesvirus 1 (SHV1), which causes pseudorabies (PRV) in pigs, is an alpha-herpesvirus and results in neonatal death of piglets, and can be eradicated by vaccination. The glycoprotein II gene of SHV1 is reportedly closely related to the gpB gene of other herpesviruses (Robbins et al. (1987) *J. Virology.* 61:2691–2701). Suid herpesvirus 2 (SHV2), also known as pig cytomegalovirus (pCMV), is found in the respiratory tract of pigs and causes atopic rhinitis, abortion, or neonatal piglet losses. Only the DNA polymerase gene of SHV2 has been reported (Genbank Accession Number AJ222640). Detection of two novel porcine herpesviruses with high similarity to other gamma-herpesviruses were recently reported (Ehlers et al. (1999) *J. General Virology,* 80:971–978), wherein the sequence of the DNA polymerase gene was reported (Genbank Accession Numbers AF118399 and AF118401).

Subsequent examination, as disclosed herein, of pigs for the presence of a gamma-herpesvirus by PCR methods designed to amplify the DNA regions encoding all or part of the glycoprotein B (gpB) envelope molecule has resulted in the detection of sequence similarity to other known gamma-herpesviruses.

BRIEF SUMMARY OF THE INVENTION

It is an object of the present invention to provide isolated polynucleotide sequences encoding a polypeptide that corresponds to a novel porcine gamma-herpesvirus glycoprotein B, herein called pGHV-gpB. Such sequences may be derived from genomic DNA.

It is another object of the present invention to provide immunogenically active fragments and segments of said polynucleotide for use as probes in the detection of similar sequences in related organisms.

A further object of this invention is to use the polypeptides and fragments thereof of the invention to provide a vaccine against porcine gamma-herpesvirus organisms, which vaccine is useful to protect a pig from productive proliferation of this, or related, gamma-herpesvirus organisms.

A still further object of the present invention is to provide antibodies that are capable of binding to an epitope on the porcine gamma-herpesvirus gpB polypeptides, and fragments, of the invention. Such antibodies are useful for diagnosis of the presence of pGHV-gpB polypeptides or as part of a vaccination program.

BRIEF DESCRIPTION OF THE DRAWINGS

FIG. 1 shows the alignment of Glycoprotein-B (gpB) protein sequences from several known gamma-herpesviruses. The following gamma-herpesviruses were used for the analysis: human herpesvirus 8 (HHV8PEP; Genbank accession number AF092928), rhesus monkey rhadinovirus (RHESRHADPEP; Genbank accession number AF029302), murine herpesvirus 68 (MURH68PEP; Genbank accession number U97553), bovine herpesvirus 4 (BOVINEH4PEP; Genbank accession number Z15044), ateline herpesvirus 3 (ATELINEH3PEP; Genbank accession number AF083424), herpesvirus saimiri (SAIMIRIPEP; Genbank accession number X64346), equine herpesvirus 2 (EQH2PEP; Genbank accession number U20824), Epstein-Barr virus (EBVPEP; Genbank accession number V01555), Alcelaphine herpesvirus 1 (ALCELPEP; Genbank accession number AF005370), and equine herpesvirus 5 (EQH5PEP; Genbank accession number AF050671). Degenerate primers were designed for conserved regions (underlined) along with specific primers for Epstein-Barr Virus (EBV) for control and optimization purposes. Such sequences are continued through FIGS. 1(a), 1(b) and 1(c).

FIG. 2 shows the DNA sequence of the pGHV-gpB gene (SEQ ID NO: 23) that encodes a gamma-herpesvirus gpB polypeptide of the present invention. A fragment of this is shown as SEQ ID NO: 1.

FIG. 3 shows the deduced polypeptide sequence of the pGHV-gpB cDNA shown in FIG. 2 (SEQ ID NO: 24). The amino acids of the sequence are represented by standard one-letter codes. A fragment of this is shown as SEQ ID NO: 2.

FIG. 4 shows a comparison of the nucleic acid sequences of pGHV-gpB and SHV1 and is therefore an illustration of the nucleic acid sequence identity between SEQ ID NO: 1 (a portion of the sequence of FIG. 2) and a portion of Suid herpesvirus 1 (SHV1, Genbank accession number M17321 nucleotides 641–1300). Row 1 (pGHV-gpB DNA) of the compared sequences is SEQ ID NO: 1 (a portion of the sequence of FIG. 2), row 2 is SHV1 (pGHV1 in the figure), nucleotides 641–1300, and row 3 indicates the nucleotides that show identity. Dashes indicate gaps that were inserted in the alignment process to maximize sequence identity.

FIG. 5 is a comparison of the protein sequences of pGHV-gpB and SHV1 and thus an illustration of the identity between the deduced amino acid sequence of SEQ ID NO: 2 (a portion of the sequence of FIG. 3) and SHV1. The amino acids of the sequence are represented by standard one-letter codes.

Row 1 of the compared sequences is SEQ ID NO: 2, row 2 is the amino acid sequence of SHV1 (pGHV1; amino acids 491–850) and row 3 indicates the amino acids that show identity. Dashes indicate gaps that were inserted in the alignment process to maximize sequence identity.

FIG. 6 is a comparison of the nucleic acid sequences of pGHV-gpB and SHV2 and illustrates the nucleic acid sequence identity between SEQ ID NO: 1 and a portion of suid herpesvirus 1 (SHV2, Genbank accession number AJ222640). Row 1 of the compared sequences is SEQ ID NO: 1, row 2 is SHV2, and row 3 indicates the nucleotides that show identity. Dashes indicate gaps that were inserted in the alignment process to maximize sequence identity.

FIG. 7 shows a comparison of the protein sequences of pGHV-gpB and SHV2 and illustrates the identity between the deduced amino acid sequence of SEQ ID NO: 2 and that of SHV2. The amino acids are represented by standard one-letter codes. Row 1 of the compared sequences is SEQ ID NO: 2, row 2 is the amino acid sequence of SHV2, and row 3 indicates the amino acids that show identity. Dashes indicate gaps that were inserted in the alignment process to maximize sequence identity.

FIG. 8 is an illustration of the nucleic acid sequence identity between SEQ ID NO:1 and a portion of the porcine gamma-herpesvirus polymerase (AF118399). Row 1 of the compared sequences is SEQ ID NO:1, row 2 is AF118399 and row 3 indicates the nucleotides that show identity. Dashes indicate gaps that were inserted into the alignment process to maximize sequence identity.

FIG. 9 is an illustration of the nucleic acid sequence identity between SEQ ID NO:1 and a portion of the porcine gamma-herpesvirus polymerase (AF118401). Row 1 of the compared sequences is SEQ ID NO:1, row 2 is AF118401 and row 3 indicates the nucleotides that show identity. Dashes indicate gaps that were inserted into the alignment process to maximize sequence identity.

FIG. 10 shows a Blast 2 sequence comparison of the nucleic acid sequence of pGHV-gpB and Acelaphine herpesvirus (GenBank Accession No. AF005370). The vertical lines indicate matches between the two sequences. The upper "Query" sequence represents the gpB nucleotide sequence while the lower "subject" sequence is the Acelaphine herpesvirus sequence. The numbers for the upper sequence correspond to the residue numbers shown for the sequence of FIG. 2 (SEQ ID NO: 23). About 76% of the residues matched.

FIGS. 11(*a*) and (*b*) show a comparison of the protein sequences of pGHV-gpB and Acelaphine herpesvirus (GenBank Accession No. gi/2337975 (AF005370). The amino acids of these sequences are represented by the standard one-letter codes. Row 1 (query) of the compared sequences is the pGHV-gpB while the lower row (the "subject" sequence) is the Acelaphine herpesvirus sequence. The numbers for the upper row correspond to the residue numbers shown in FIG. 3 (SEQ ID NO: 24).

DETAILED DESCRIPTION OF THE INVENTION

In accordance with one aspect of the present invention, there is disclosed herein an isolated polynucleotide which encodes the polypeptide comprising the amino acid sequence of SEQ ID NO: 24, corresponding to the gpB envelope protein of porcine gamma herpesvirus. Also disclosed are fragments of these polynucleotide and polypeptide sequences, especially that of SEQ ID NO:1 (polynucleotide) and SEQ ID NO:2 (polypeptide).

Polynucleotide sequences of the present invention have been isolated from genomic DNA of miniature swine. These sequences show only low sequence similarity with other known porcine herpesvirus sequences (SHV1 and SHV2 and gamma-herpesvirus polymerase gene), including the sequences corresponding to Genbank Accession Numbers M17321, AJ222640, AF118399 and AF118401, respectively.

In accordance with a further aspect of the present invention the nucleic acid sequences of SEQ ID NO: 23, including fragments thereof, may be utilized under stringent hybridization conditions to isolate from porcine tissue by procedures known in the art, DNA sequences corresponding to porcine gamma-herpesvirus gpB regions and for complete porcine gamma-herpesvirus sequences.

Fragments of the polynucleotide sequences of the present invention were used as hybridization probes for a cDNA or DNA library to isolate the full-length gamma-herpesvirus sequence or fragments thereof. Such fragments also find use as probes in identifying other similar sequences of related organisms. Thus, the present invention further provides an isolated porcine gamma-herpesvirus polynucleotide fragment that is capable of stringently hybridizing to a porcine gamma-herpesvirus polynucleotide sequence. In this manner, the present invention provides probes and/or primers for use in ex vivo porcine gamma-herpesvirus detection studies. Typical detection methods involve use of the polymerase chain reaction, sequence analysis, and hybridization techniques. Thus, the present invention also provides pGHV-gpB specific oligonucleotide probes and primers.

The present invention further relates to a method of detecting the presence of gamma herpesvirus in a sample comprising detecting the presence in said sample of a polynucleotide having a sequence at least 80%, preferably at least 90%, most preferably 95% identical to a sequence encoding a polypeptide of the present invention. Said sample may be blood or other tissue sample. The presence of a polypeptide, or immunogenic fragments thereof, of the present invention may also be detected in such samples.

In addition, the present invention also relates to an isolated nucleic acid probe comprising an oligonucleotide whose sequence is at least 95% identical to a fragment, portion or segment of a polynucleotide encoding a polypeptide of the present invention. Such oligonucleotide probe may be either a DNA (i.e., a polydeoxyribonucleotide) or an RNA (i.e., a polyribonucleotide). In a preferred embodiment, said oligonucleotide probe and said fragment have the same sequence.

In a particular embodiment, said isolated nucleic acid probe will comprise an oligonucleotide that is at least 15 nucleotides in length, preferably at least 30 nucleotides in length, most preferably at least 60 nucleotides in length, and especially where said probe is at least 100 nucleotides in length. Such probes commonly hybridize to said oligonucleotides under stringent conditions, as defined herein. SEQ ID NO: 1. In another specific embodiment, the isolated nucleic acid probe oligonucleotide has the sequence of SEQ ID NO: 1.

In a separate embodiment, the isolated nucleic acid probe oligonucleotide of the present invention has a sequence at least 95% identical to the sequence, and is preferably identical to a sequence, selected from the group consisting of the sequences of SEQ ID NO: 25, 26, 27, 28, 29, 30, 31, 32, 33, 34, 35, and 36.

The method of the present invention also provides a means wherein the polynucleotide coding for gpB protein is detected using a probe as disclosed herein. Useful probes also include oligonucleotides whose sequence is selected from the group consisting of SEQ ID NO: 25, 26, 27, 28, 29, 30, 31, 32, 33, 34, 35, and 36.

Porcine gamma-herpesvirus specific oligonucleotides can be detected and/or prepared from the porcine gamma-herpesvirus gpB sequence of the present invention and can be synthesized according to known techniques. They will have substantial sequence identity (e.g., at least 75%, preferably at least 90%, most preferably at least 95%, and most especially 100% sequence identity) with one of the strands (either plus or minus) shown herein (SEQ ID NO: 23, which shows the sense, or plus, or coding, or anti-template strand) or an RNA equivalent, or with part of such a strand, or with a complement thereof.

The present invention further relates to isolated polynucleotides having at least 75% identity to the nucleotide sequence of SEQ ID NO: 23, preferably at least 90% sequence identity thereto, most preferably at least 95% sequence identity thereto, with the preferred embodiment being an isolated polynucleotide comprising the nucleotide sequence of SEQ ID NO: 23.

Likewise, polypeptides comprising the peptides encoded by porcine gamma-herpesvirus sequences are useful for generating antibodies to detect the presence of gamma-herpesvirus polypeptides when they are expressed in porcine tissues. Most useful is the polypeptide sequence of SEQ ID NO:24 (gpB protein) as well as immunogenically active fragments thereof (for example, the fragment whose sequence is that of SEQ ID NO: 2).

The present invention also relates to fragments, portions and segments of the polynucleotides and polypeptides disclosed herein, especially where said fragments, portions or segments are useful as probes (in the case of polynucleotides) or have immunogenic activity (in the case of polypeptides). Polypeptides of the present invention include fragments having at least 30, preferably at least 50, and most preferably at least 70 amino acid residues in common with some portion of the sequence of SEQ ID NO: 24.

"Polynucleotide sequences" as used herein refers to a chain of nucleotides such as deoxyribose nucleic acid (DNA) and transcription products thereof, such as RNA. The polynucleotides of the present invention include DNA, which includes cDNA, genomic DNA, non-genomic DNA, and synthetic DNA, and RNA, such as mRNA present in infected cells.

The term "oligonucleotide" encompasses nucleotides of preferably at least 15 bases (e.g. 15 bases to 600 bases) in length, more preferably 15 bases to 50 bases and most preferably 15 bases to 100 bases.

The term "gene" means the segment of DNA involved in producing a polypeptide chain; it includes regions preceding and following the coding region (leader and trailer sequences) as well as intervening sequences (introns) between individual coding segments (exons).

"Stringent hybridization" or "hybridization under stringent conditions" means hybridization that can be effected at a temperature of between 50° C. and 70° C. in 2×SSC (1×SSC is 17.5 g NaCl, 8.8 g of sodium citrate in 800 ml of $H_2O$, the pH is adjusted to 7.4 with NaOH and the volume adjusted to one liter), containing 0.1% sodium dodecyl sulfate (SDS). In a most preferred embodiment, the sample and probes are sufficiently similar that the hybridization is unaffected by treatment with 0.1×SSC and 0.1% SDS at 65° C. Gamma-herpesvirus gpB specific oligonucleotides can be designed to specifically hybridize to gamma-herpesvirus specific nucleic acids. They can also be synthesized by known techniques and used as primers in PCR (i.e., polymerase chain reaction), or sequencing reactions, or as probes in hybridizations designed to detect the presence of gamma herpesvirus material in a sample. The oligonucleotides may be labeled by suitable labels known in the art, such as radioactive labels, chemiluminescent labels or fluorescent labels and the like.

In accordance with the present invention, the term "Percent Identity" or "Percent Identical", when referring to a sequence, means that a sequence is compared to a claimed or described sequence after alignment of the sequence to be compared (the "Compared Sequence") with the described or claimed sequence (the "Reference Sequence"). The percent identity is then determined according to the following formula:

Percent Identity=100[1−(C/R)]

wherein C is the number of differences between the Reference Sequence and the Compared Sequence over the length of alignment between the Reference Sequence and the Compared Sequence wherein (i) each nucleotide or amino acid in the Reference Sequence that does not have a corresponding aligned nucleotide or amino acid in the Compared Sequence and (ii) each gap in the Reference Sequence and (iii) each aligned nucleotide or amino acid in the Reference Sequence that is different from an aligned nucleotide or amino acid in the Compared Sequence, constitutes a difference; and R is the number of nucleotides or amino acids in the Reference Sequence over the length of the alignment with the Compared Sequence with any gap created in the Reference Sequence also being counted as a nucleotide or amino acid. If an alignment exists between the Compared Sequence and the Reference Sequence for which the Percent Identity as calculated above is about equal to or greater than a specified minimum Percent Identity then the Compared Sequence has the specified minimum Percent Identity to the Reference Sequence even though alignments may exist in which the hereinabove calculated Percent Identity is less than the specific Percent Identity.

Typically, the melting temperature ($T_m$) of an oligonucleotide less than 30 nucleotides may be calculated according to the formula:

$T_m$=86.35−0.41[%(G+C)]−600/N where N=Chain Length (i.e., number of base pairs)

The present invention also relates to vectors that include the novel polynucleotides (including fragments, segments and portions thereof, as defined below) disclosed herein, host cells which are genetically engineered with or without vectors of the invention to contain said polynucleotides and express said polypeptides, and the synthesis of polypeptides of the invention by recombinant techniques or by direct chemical synthesis.

As used herein, the terms "portion," "segment," and "fragment," when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to a polynucleotides, such terms refer to the products produced by treatment of said polynucleotides with any of the common endonucleases or exonucleases.

A polypeptide of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The present invention further relates to a polypeptide which comprises the deduced amino acid sequence of SEQ ID NO: 24, as well as fragments thereof. Preferred are fragments comprising 25 or more consecutive amino acids, more preferred are fragments are fragments with at least 40 amino acids and even more preferred are fragments comprising 50 or more amino acids of the polypeptide of SEQ ID NO: 24. A preferred embodiment is the sequence of SEQ ID NO: 2.

The present invention further relates to variants of the disclosed polynucleotides which encode fragments, including analogs and derivatives, of the polypeptide comprising the amino acid sequence of SEQ ID NO: 24. Such variants may be naturally occurring allelic variants of the polynucleotides or may be non-naturally occurring (for example, variants produced by mutagenesis techniques).

Additional preferred embodiments include polynucleotides encoding gamma herpesvirus polypeptide variants, analogs, derivatives and fragments, and variants, analogs and derivatives of the fragments, which comprise the amino acid sequence of SEQ ID NO:2 in which one or more of the amino acids have optionally been replaced so long as said polypeptide still retains at least 80% identity with the amino acid sequence of SEQ ID NO 24, more preferably 90% sequence identity therewith, most preferably 95% sequence identity therewith and most especially being identical to the sequence of SEQ ID NO: 24, regardless of whether such sequence identities are achieved through addition, deletion, or substitution of amino acid residues.

Especially preferred among these are conservative substitutions, additions and deletions, which do not alter the properties and activities of the gamma herpesvirus gpB polypeptide. Also especially preferred are conservative substitutions. Most highly preferred are mature polypeptides comprising the amino acid sequence set forth in SEQ ID NO: 24 without substitutions.

Thus, the present invention includes polynucleotides encoding polypeptides comprising the sequence of SEQ ID NO: 24 as well as variants of such polynucleotides which variants encode a fragment, derivative or analog of the polypeptides set forth in SEQ ID NO: 24. Such nucleotide variants include deletion variants, substitution variants and addition or insertion variants.

As hereinabove indicated, the polynucleotides may have a coding sequence which is a naturally occurring allelic variant of the coding sequences comprising the coding portion of the polynucleotide sequence shown in FIG. 2 (of SEQ ID NO: 23). As known in the art, an allelic variant is an alternate form of a polynucleotide sequence which may have a substitution, deletion or addition of one or more nucleotides, which does not substantially alter the function of the encoded polypeptide.

The present invention also encompasses polynucleotides which may be fused in the same reading frame to a polynucleotide sequence which aids in expression and secretion of a polypeptide from a host cell, for example, a leader sequence which functions as a secretory or signal sequence for controlling transport of a polypeptide from the cell. The polypeptide having a leader sequence is a pre-protein and may have the leader sequence cleaved by the host cell to form the secreted form of the polypeptide.

The polynucleotides of the present invention may also have the coding sequence fused in frame to a marker sequence which allows for purification of the polypeptides of the present invention. The marker sequence may be a hexa- histidine tag supplied by a pQE-9 vector to provide for purification of the mature polypeptides fused to the marker in the case of a bacterial host, or, for example, the marker sequence may be a hemagglutinin (HA) tag when a mammalian host, e.g. COS7 cells, is used. The HA tag corresponds to an epitope derived from the influenza hemagglutinin protein (Wilson, I., et al. 1984. *Cell* 37:767).

The terms "derivative" and "analog" when referring to the polypeptides comprising the polypeptide as set forth in SEQ ID NO:24, means polypeptides which retain essentially the same biological function or activity as such polypeptides. Thus, an analog includes a pre-protein which can be secreted following cleavage of the pre-protein portion to produce an secretable polypeptide.

The polypeptides of the present invention may be recombinant polypeptides, natural polypeptides or synthetic polypeptides, preferably recombinant polypeptides.

The fragment, derivative or analog of the polypeptides comprising the amino acid sequence set forth in SEQ ID NO: 24 may be one in which one or more of the amino acid residues are substituted with a conserved or non- conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the polypeptide, such as a leader or secretory sequence or a sequence which is employed for purification of the mature polypeptide or a pre-protein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include polypeptides comprising the polypeptide of SEQ ID NO:2 or a fragment thereof, which fragment may be all or a portion of the polypeptide of SEQ ID NO:2, as well as polypeptides which have at least 80% similarity to such polypeptides, preferably at least 90% similarity, more preferably at least 95% similarity, and most preferably are identical to polypeptides comprising the amino acid sequence of SEQ ID NO:2 and include portions or fragments of such polypeptides with such portion or fragment comprising at least 30 amino acids, preferably at least 40 amino acids and most preferably at least 50 amino acids. Preferred embodiments are fragments comprising 30 or more consecutive amino acids, more preferred are fragments with at least 40 amino acids and even more preferred are fragments comprising 50 or more amino acids of the polypeptide of SEQ ID NO:24, such as SEQ ID NO: 2 (which corresponds to residue numbers 484–678 of SEQ ID NO: 24 (shown in FIG. 3).

As known in the art "similarity" between two polypeptides is determined by comparing the amino acid sequence and its conserved amino acid substitutes of one polypeptide to the sequence of a second polypeptide. For such a determination, two amino acid sequences are compared along a stretch of their sequences, any gap (or gaps) introduced in one sequence to improve the alignment and similarity to the other sequences is counted as spaces of dissimilarity equal to the number of amino acids corresponding to the gap which are present in the second sequence, and the total number of similar amino acids are divided by the total number of amino acids present in the comparison area which counts the spaces of gaps as part of the comparison area.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides, and fragments thereof, of the present invention, host cells which are genetically engineered with vectors of the invention and the production of polypeptides of the invention by recombinant techniques.

Host cells are genetically engineered (transduced or transformed or transfected) with the vectors of the invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli*. lac or trp, the phage lambda PL promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli, Streptomyces, Salmonella typhimurium*; fungal cells, such as yeast; insect cells such as Drosophila S2 and Spodoptera Sf9 animal cells such as CHO, COS or Bowes melanoma; adenoviruses; plant cells, etc. The selection of an appropriate host is deemed to be within the scope of those skilled in the art from the teachings herein.

More particularly, the present invention relates to recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pBluescript—SK, pBSKS, pNH8A, pNH16a, pNH18A, pNH46A (Stratagene); pTRC99a, pKK2233, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host. Baculovirus systems are especially useful in practicing the present invention.

Promoter regions can be selected from any desired gene using CAT (chloramphenicol transferase) vectors or other vectors with selectable markers. Two appropriate vdctors are pKK232-8 and pCM7. Particular named bacterial promoters include lacI, lacZ, T3, T7, gpt, lambda PRI PL and trp. Eukaryotic promoters include CMV immediate early, HSV thymidine kinase, early and late SV40, LTRs from retrovirus, and mouse metallothionein-1. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE Dextran mediated transfection, or electroporation (Davis, L., Dibner, M., Battey, I., Basic Methods in Molecular Biology, (1986)).

The constructs in host cells can be used in a conventional manner to produce the gene products encoded by the recombinant sequences. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), alpha-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *Escherichia coli, Bacillus subtilis, Salmonella typhimurium* and various species within the genera *Pseudomonas, Streptomyces*, and *Staphylococcus*, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS7 lines of monkey kidney fibroblasts, described by Gluzman (1981) *Cell*, 23:175, and other cell lines capable of expressing a compatible vector, for example, the C127, 3T3, CHO, HeLa, 293 and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the expressed polypeptide. Finally, high performance liquid chromatography (HPLC) can be employed for final purification steps.

The present invention also relates to diagnostic assays for detecting expression of the gamma-herpesvirus gpB polypeptide in various tissues. Assays used to detect levels of the gamma-herpesvirus gpB polypeptide in a sample derived from a host are well-known to those of skill in the art and include radioimmunoassays, competitive-binding assays, Western Blot analysis, ELISA assays and "sandwich" assay. An ELISA assay (Coligan, et al., Current Protocols in Immunology, 1(2), Chapter 6, (1991)) initially comprises preparing an antibody specific to the gamma-herpesvirus gpB polypeptide antigen, preferably a monoclonal antibody. In addition a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g. a polystyrene dish that binds the proteins in the sample. Any free protein binding sites on the dish are then covered by incubating with a non-specific protein like BSA (bovine serum albumin). Next, the monoclonal antibody is incubated in the dish during which time the monoclonal antibodies attach to gamma-herpesvirus gpB polypeptide attached to the polystyrene dish. All unbound monoclonal antibody is washed out with buffer. The reporter antibody linked, for example, to horseradish peroxidase is then placed in the dish resulting in binding of the reporter antibody to any monoclonal antibody bound to the gamma-herpesvirus gpB polypeptide. Unattached reporter antibody is then washed out. Peroxidase substrates are then added to the dish and the amount of color developed in a given time period is a measurement of the amount of the gamma-herpesvirus gpB polypeptide, or fragments thereof, present in a given volume of sample when compared against a standard curve.

A competition assay may be employed wherein antibodies specific to the gamma-herpesvirus gpB polypeptide, or fragments thereof, are attached to a solid support, labeled gamma-herpesvirus gpB polypeptide and a sample derived from the host are passed over the solid support, and the amount of label detected. The label can be detected, for example, by liquid scintillation chromatography and can be correlated to a quantity of the gamma-herpesvirus gpB polypeptide present in the sample.

A "sandwich" assay is similar to an ELISA assay. In a "sandwich" assay the gamma-herpesvirus gpB polypeptide, or a suitable fragment thereof, is passed over a solid support and binds to antibody attached to a solid support. A second antibody is then bound to the gamma-herpesvirus gpB polypeptide. A third antibody which is labeled and specific to the second antibody is then passed over the solid support and binds to the second antibody and an amount can then be quantified.

The present invention also relates to compositions comprising immunogenic polypeptides, and active fragments thereof, disclosed according to the invention. Where intended for use in a clinical setting, such compositions will commonly contain the polypeptides, and active fragments thereof, suspended in a pharmacologically acceptable diluent or excipient.

The present invention further relates to the use of such compositions as vaccines, wherein said vaccines comprise immunogenically effective amounts of said compositions. Additionally, the invention contemplates a method of vaccinating a pig against a porcine, or swine, gamma-herpesvirus by administering to said pig the vaccine of the present invention.

The present invention also relates to a method of immunizing an animal, especially a pig, against a porcine gamma-herpesvirus, comprising administering to said pig an isolated polynucleotide encoding a polypeptide (or immunogenically active fragments thereof) according to the invention, such that the encoded polypeptide is eventually expressed in an immunogenically effective amount.

Pharmaceutical compositions, such as those designed to vaccinate, or otherwise induce active immunity, may be administered in a convenient manner such as by topical, intravenous, intraperitoneal, intramuscular, intratumor, subcutaneous, intranasal or intradermal routes. Such pharmaceutical compositions are administered in an amount which is effective for treating and/or prophylaxis of the specific indication.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of a Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptide itself. In this manner, even a sequence encoding only a fragment of the polypeptide can be used to generate antibodies binding the whole native polypeptide. Such antibodies can then be used to isolate the polypeptide from tissue expressing that polypeptide.

Antibodies specific to the polypeptide of the present invention may be employed as a diagnostic to determine the presence of a gamma-herpesvirus in tissue, which gamma herpesvirus expresses the gpB polypeptide (or a related polypeptide) in a sample derived from a host by techniques known in the art. Such antibodies may be useful to provide passive immunity in a host.

More specifically, the present invention relates to a method for creating, or otherwise producing or inducing, passive immunity in a pig comprising administering to said pig an immunogenically effective amount of one or more antibodies specific for the polypeptides, or fragments thereof, disclosed herein.

For preparation of monoclonal antibodies, any technique which provides antibodies produced by continuous cell line cultures can be used. Examples include the hybridoma technique (Kohler and Milstein (1975) *Nature*, 256:495–497), the trioma technique, the human B-cell hybridoma technique (Kozbor et al. (1983) *Immunology Today* 4:72), and the EBV-hybridoma technique to produce human monoclonal antibodies (Cole et al. (1985) in *Monoclonal Antibodies and Cancer Therapy*, Alan R. Liss, Inc., pp. 77–96), to mention only a few. Newer technologies present no obstacles to practicing the present invention.

Antibodies specific for the polypeptides disclosed herein may also be generated by genetically engineered cells transformed by the introduction into the genome of said cells, or by introduction of non-integrating vectors into said cells, of either polynucleotides alone, or vectors containing said polynucleotides, coding for said antibodies.

Techniques described for the production of single chain antibodies (U.S. Pat. No. 4,946,778) can be adapted to produce single chain antibodies to immunogenic polypeptide products of this invention.

Such antibodies to the polypeptides of the present invention may be utilized to detect the presence or the absence of the polypeptides of the present invention. Thus, they are useful in an assay to verify the successful insertion of the polynucleotides of the present invention (as part of a construct) into a host cell. Thus, the protein encoded by the inserted polynucleotide according to the present invention, when expressed by the transformed host cell, serves as a "marker" for the successful insertion of the polynucleotide that can be detected by an antibody for the marker.

In general, antibodies against the polypeptides will be administered in an amount of at least about 10 mg/kg body weight and in most cases they will be administered in an amount not in excess of about 8 mg/kg body weight per day. In most cases, the dosage is from about 1 mg/kg to about 10 mg/kg body weight daily, taking into account the routes of administration, symptoms, etc.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid, or DNA fragment is used with about 2 units of enzyme in about 20 μl of buffer solution. For the purpose of isolating DNA fragments for plasmid construction, typically 5 to 10 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

General procedures useful in practicing the methods disclosed herein can be found in, for example, Sambrook et al., Molecular Cloning: A Laboratory Manual, Second Edition, Cold Spring Harbor, N.Y., (1989), Wu et al, *Methods in Gene Biotechnology* (CRC Press, New York, N.Y., 1997), and *Recombinant Gene Expression Protocols*, in *Methods in Molecular Biology*, Vol. 62, (Tuan, ed., Humana Press, Totowa, N.J., 1997), the disclosures of which are hereby incorporated by reference.

"Ligation" refers to the process of forming phosphodiester bonds between two double stranded nucleic acid fragments (See Sambrook et al, supra).

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The present invention will be further described with reference to the following examples; however, it is to be understood that the present invention is not limited to such examples. All parts or amounts, unless otherwise specified, are by weight. In order to facilitate understanding of the invention the following examples providing certain frequently occurring methods and/or terms will be described.

EXAMPLE 1

Isolation and Sequence Analysis of Porcine Gamma-Herpesvirus Glycoprotein B Gene Sequences Primers: Primers were synthesized for use in the amplification of pGHV-gpB gene sequences. Alignment of gpB protein sequences from several known gamma-herpesviruses (FIG. 1) showed that there are four conserved regions (identified by underlining). Degenerate primers corresponding to these regions were synthesized (Table 1).

TABLE 1

R = A or G   Y = C or T   M = A or C   K = G or T   S = G or C
W = A or T   H = A or T or C   B = G or T or C
D = G or A or T   N = A or G or C or T   V = G or A or C   I = Inosine F and R indicate whether the primers were in the sense or antisense direction respectively.

| Degenerate Primers | Polypeptide Sequence | Sequence (5' to 3') |
|---|---|---|
| RTT-F1 | Includes sequence RTTVNC | MGA ACA ACI GTY AAY TGY GA |
| RTT-F2 | Includes sequence RTTVNC | MGA ACA ACI GTY AAY TGY CT |
| RTT-F3 | Includes sequence RTTVNC | MGA ACA ACI GTY AAY TGY |

-continued

| Degenerate Primers | Polypeptide Sequence | Sequence (5' to 3') |
|---|---|---|
| QLIV-F4 | Includes sequence QXQF/YAY | CAR ITI CAR TWT GCM TAY GAC |
| QLIV-F5 | Includes sequence QXQF/YAY | CAR ITI CAR TWT GCM TAY G |
| NPTV-F6 | Includes sequence VMXS/T/AY | GTB ATG WSH AGV ATH TAY GG |
| NPTV-F7 | Includes sequence VMXS/T/AY | GTB ATG WSH GCV ATH TAY GG |
| NPTV-R1 | | SWC ATI ACR STI GTI GGR TT |
| FREYN-R3 | Includes sequence FREYN | TR IGY GTA RTA RTT RTA YTC YCT RAA |
| FREYN-R4 | Includes sequence FREYN | GTA RTA RTT RTA YTC YCT RAA |
| FREYN-R5 | Includes sequence FREYN | CTG RAA RTT RTA YTC YCG RAA |
| FREYN-R6 | Includes sequence FREYN | TG IGY CTG RAA RTT RTA YTC YCG RAA |

Primers were also designed to Epstein-Barr virus (EBV) for control and assay optimization purposes (Table 2). Primer names ending with an "F" are sense strand primers, primer names ending with an "R" are anti-sense strand primers.

TABLE 2

| Epstein-Barr Virus Control Primers | Similar to: | Sequence (5' to 3') |
|---|---|---|
| EBV-F2 | RTT-F2 | AGA ACT ACC GTC AAC TGC CT |
| EBV-F3 | RTT-F3 | AGA ACT ACC GTC AAC TGC |
| EBV-F4 | QLIV-F4 | CAG ATC CAA TTT GCC TAC GAC |
| EBV-F5 | QLIV-F5 | CAG ATC CAA TTT GCC TAC G |
| EBV-F6 | NPTV-F6 | GTC ATG TCC AGC ATC TAC GG |
| EBV-R1 | NPTV-R1 | GAC ATG ACG GTG GTT GGA TT |
| EBV-R3 | FREYN-R3 | TGC GCC TGG AAG TTG TAC TCC CGG AA |
| EBV-R5 | FREYN-R5 | CTG GAA GTT GTA CTC CCG GAA |

Oligonucleotides used to sequence the pGHV gpB gene were as follows:

| Sequencing Primers | Sequence (5' to 3') | Hybridizes To: |
|---|---|---|
| -47 Sequencing Primer | CGC CAG GGT TTT CCC AGT CAC GAC | TOPO-pCRII: bases 434–458 |
| M13 Reverse | CAG GAA ACA GCT ATG AC | TOPO-pCRII: bases 205–222 |
| TEF-14 | CAG GGA CGA GAA GAG GCT TA | pGHV gpB: bases 1989–2008 |
| TER-22 | ACA CCA GAG CAG CTC TAT G | pGHV gpB: bases 1513–1531 |
| TEF-23 | TAG CAC CAA TCA GTG AAG AAG AGC | pGHV gpB: bases 2399–2422 |
| TEF-24 | GCC AGT GAT ATG GTA CAC AGT G | pGHV gpB: bases 322–343 |
| TEF-25 | TAA CAG GTC ACT ATG GAA CAC ACG | pGHV gpB: bases 140–163 |
| TEF-26 | TTC TTT AAG ACT AAA CAC AGG TGG | pGHV gpB: bases 537–560 |
| TEF-27 | GGA GTG GTG AAG ATG ATC ATG | pGHV gpB: bases 815–835 |
| TER-28 | CCA TAA TGT TAG TGG ACA ATA TGA C | pGHV gpB: bases 993–1017 |
| TER-29 | ATG ACG CTG TGA TGT CAT TGG | pGHV gpB: bases 1073–1093 |
| TER-30 | GAT GCA CTG AGA AGC CTG AGA C | pGHV gpB: bases 1673–1694 |

Isolation and Sequence Analysis of Porcine Gamma-Herpesvirus Glycoprotein B

Equal amounts of genomic DNA from miniature swine #13432 and #13433 were pooled together. These animals (a/d haplotype) had been the recipients of bone marrow or stem cells from a/c haplotype animals and had been given cyclosporine treatment. The animals had both developed a lymphoma. Genomic DNA was extracted using Qiagen, Inc.'s QIAmp® Blood Kit (Chatsworth, Calif.). One hundred ng of the DNA pool was added to each polymerase chain reaction (PCR) tube along with reagents. The final 50 $\mu$l reaction mixtures included 25 mM KCl, 10 mM Tris-HCl (pH 8.3), 3.5 mM $MgCl_2$ (Stratagene, Los Angeles, Calif.), 0.2 mM dNTP and 2.5 units of Amplitaq Gold® DNA polymerase (Perkin-Elmer Corporation, Philadelphia, Pa.). Several different combinations of forward and reverse primers were used (20 pmoles of each primer per reaction). These are summarized as follows:

| Forward Primer | Reverse Primer |
|---|---|
| QLIV-F4 | FREYN-R5 |
| EBV-F4 | FREYN-R5 |
| QLIV-F4 | EBV-R5 |
| QLIV-F4 | FREYN-R6 |
| QLIV-F5 | FREYN-R5 |
| EBV-F5 | FREYN-R5 |
| QLIV-F5 | EBV-R5 |
| QLIV-F5 | FREYN-R6 |
| EBV-F4 | FREYN-R3 |
| EBV-F4 | FREYN-R4 |
| QLIV-F4 | FREYN-R3 |
| QLIV-F4 | FREYN-R4 |
| QLIV-F5 | FREYN-R3 |
| QLIV-F5 | FREYN-R4 |

The reactions were amplified in a Perkin-Elmer Gene-Amp® 9600 thermal cycler. The initial denaturing step was 9 minutes at 95° C. (required to activate the "hot-start" Amplitaq Gold®) followed by 30 cycles of 94° C. for 30 seconds, 45° C. for 60 seconds and 72° C. for 60 seconds. Thermal cycling was followed by a 5 minutes incubation at 72° C. and brought down to 4° C.

The PCR products were visualized on a 2% agarose gel stained with ethidium bromide. PCR products were visible using the following primer pairs: QLIV-F5/FREYN-R6, EBV-F4/FREYN-R4, QLIV-F4/FREYN-R4, QLIV-F5/FREYN-R3. The sizes of the product varied from approximately 350 base pairs to 800 base pairs (expected size of the product was approximately 600 base pairs). The PCR products were purified using Microspin G-50® columns (Amersham Pharmacia Biotech, Newark, N.J.) and TA-ligated into the pCRII-TOPO® vector (Invitrogen Corp., San Diego, Calif.). The ligation reactions were then transformed into competent TOP10F' E.coli supplied by Invitrogen Corp. The cells were incubated on carbenicillin (Sigma Chemical Company, St. Louis, Mo.)/IPTG/X-gal (Amresco, Inc., Solon Ohio) agar plates and selected colonies were grown up in LB broth (Gibco Life Technologies, Baltimore, Md.). Plasmid DNA was extracted using the Wizard® miniprep kit (Promega Corp., Madison, Wis.). EcoRi (New England Biolabs, Beverly, Mass.) restriction digests of the minipreps were electrophoresed on a 2% agarose gel to determine the insert size.

In order to screen for herpesvirus sequences, miniprep DNA from the clones was hybridized to an EBV probe in a slot-blot array. Miniprep DNA (1 μl of each sample tested) was denatured by adding NaOH followed by a 10 minute incubation at 96° C. The samples were then added to GeneScreen® membrane (NEN Life Sciences, Pittsburgh, Pa.) inserted in a Minifold II® slot-blot apparatus (Schleicher & Schuell, Keene, N.H.). The blot was removed and crosslinked using a UV Stratalinker 1800® (Stratagene). EBV PCR product was generated from an EBV-transformed human B cell line (721.221, ATCC CRL 1855) using similar reagents and conditions as the previous PCR and with EBV-F4 and EBV-R5 primers. The PCR product was denatured and added to the Ready-to-go Beads® random priming kit (Amersham Pharmacia Biotech, Newark, N.J.) with $^{32}$P dCTP (NEN Life Sciences). Approximately $1 \times 10^6$ CPM of probe in 10 ml of ExpressHyb® hybridization solution (Clontech Laboratories, Inc., Palo Alto, Calif.) was added to a tube containing the slot-blot membrane and incubated at 60° C. for 90 minutes. The probe was then removed and the membrane was washed twice for 10 minutes with 6×SSC at 60° C. 8×10" Fuji RX film (Fisher Scientific, Pittsburgh, Pa.) was exposed to the blot overnight and developed. Several clones from the PCRs using EBV-F4/FREYN-R4 primers and QLIV-F4/FREYN-R4 hybridized to the EBV probe. Clones from other primer pairs as well as a QLIV-F4/FREYN-R4 clone with a uniquely small insert did not hybridize to the probe. Three EBV-F4/FREYN-R4 EBV-positive clones and three QLIV-F4/FREYN-R4 EBV-positive clones were selected for DNA sequencing. The DNA sequencing analysis was performed by Lark Technologies, Inc (Houston, Tex.). The DNA sequence obtained is shown in FIG. 2. The hypothetical protein sequence for the fragment of pGHV-gpB is presented in FIG. 3. The sequences were analyzed using the National Center for Biotechnology Information's BLAST database search program accessible via the internet at www.ncbi.nim.nih-.gov.BLAST (Altschul et al., 1997). pGHV-gpB was most closely aligned to Alcelaphine (wildebeest) herpesvirus 1 L-DNA (Genbank Accession Number AF005370). Comparison of pGHV-gpB sequence to SHV1 and SHV2 sequences indicated only low sequence similarity at either the nucleic acid of protein levels (FIGS. 4–7). FIGS. 8 and 9 show a comparison of the nucleic acids sequences of SEQ ID NO:1 and a portion of the porcine gamma herpesvirus polymerase (AF118399 and AF118401). FIG. 10 shows a Blast 2 sequence comparison of the nucleic acid sequence of pGHV-gpB and Acelaphine herpesvirus (AF005370). FIG. 11 shows a comparison of the protein sequences of pGHV-gpB and Acelaphine herpesvirus (AF005370).

What is claimed is:

1. An isolated polypeptide comprising an amino acid sequence with at least 80% identity to the sequence of SEQ ID NO: 24 wherein said polypeptide binds to antibodies induced by porcine gamma herpes virus.

2. The isolated polypeptide of claim 1 wherein said amino acid sequence is at least 90% identical to the sequence of SEQ ID NO: 24.

3. The isolated polypeptide of claim 1 wherein said amino acid sequence is at least 95% identical to the sequence of SEQ ID NO: 24.

4. An isolated polypeptide having the amino acid sequence of SEQ ID NO: 24.

5. A composition comprising a polypeptide selected from the group consisting of the polypeptides of claims 1, 2, 3, and 4 in a pharmacologically acceptable carrier.

* * * * *

SEQUENCE LISTING

```
<160> NUMBER OF SEQ ID NOS: 55

<210> SEQ ID NO 1
<211> LENGTH: 585
<212> TYPE: DNA
<213> ORGANISM: Artificial Sequence
<220> FEATURE:
<223> OTHER INFORMATION: Fragment from Swine Gamma Herpesvirus DNA
      coding for glycoprotein B envelope protein

<400> SEQUENCE: 1
aatcttcgta tcagaataaa taacattttg gaagatttgt caaaggcatg gtgtcgtgag      60
cagcatagag ctgctctggt gtggaatgag ctcagcaaga ttaatcccac aagcgtcatg     120
agcatgattt acaatagacc cgtatcagcc aaaagaatag gagatgtcat ttcagtctct     180
aactgtattg tggtagacca aaccagtgtc tcattacata aaagtctcag gcttctcagt     240
gcatcggatg aaaagtgctt ctctagacct ccagtgacat ttaagtttat gaatgacagt     300
actatttaca aagggcaact aggagtcaat aatgagattc tcttaaccac aacataccct     360
gaaacatgtc aggaaaacac tgagtattac tttcaggcaa agacagacat gtacatttac     420
aaaaactatg agcatttgaa gactgtgcct ttatcttcga tcaccacact agatacattt     480 atagcccttta attttacact attggagaat gttgacttta aagtcattga actttatacc     540
agggacgaga agaggcttag taatgtcttt gacattgaaa caatg                    585

<210> SEQ ID NO 2
<211> LENGTH: 195
<212> TYPE: PRT
<213> ORGANISM: Artificial Sequence
<220> FEATURE:
<223> OTHER INFORMATION: Deduced amino acid sequence derived from the
      first open reading frame of the DNA of SEQ ID NO:
```

```
<400> SEQUENCE: 2

Asn Leu Arg Ile Arg Ile Asn Asn Ile Leu Glu Asp Leu Ser Lys Ala
1               5                   10                  15

Trp Cys Arg Glu Gln His Arg Ala Ala Leu Val Trp Asn Glu Leu Ser
            20                  25                  30

Lys Ile Asn Pro Thr Ser Val Met Ser Met Ile Tyr Asn Arg Pro Val
            35                  40                  45

Ser Ala Lys Arg Ile Gly Asp Val Ile Ser Val Ser Asn Cys Ile Val
        50                  55                  60

Val Asp Gln Thr Ser Val Ser Leu His Lys Ser Leu Arg Leu Leu Ser
65                  70                  75                  80

Ala Ser Asp Glu Lys Cys Phe Ser Arg Pro Pro Val Thr Phe Lys Phe
                85                  90                  95

Met Asn Asp Ser Thr Ile Tyr Lys Gly Gln Leu Gly Val Asn Asn Glu
            100                 105                 110

Ile Leu Leu Thr Thr Thr Tyr Leu Glu Thr Cys Gln Glu Asn Thr Glu
            115                 120                 125

Tyr Tyr Phe Gln Ala Lys Thr Asp Met Tyr Ile Tyr Lys Asn Tyr Glu
    130                 135                 140

His Leu Lys Thr Val Pro Leu Ser Ser Ile Thr Thr Leu Asp Thr Phe
145                 150                 155                 160

Ile Ala Leu Asn Phe Thr Leu Leu Glu Asn Val Asp Phe Lys Val Ile
                165                 170                 175

Glu Leu Tyr Thr Arg Asp Glu Lys Arg Leu Ser Asn Val Phe Asp Ile
            180                 185                 190

Glu Thr Met
        195

<210> SEQ ID NO 3
<211> LENGTH: 19
<212> TYPE: DNA
<213> ORGANISM: Artificial Sequence
<220> FEATURE:
<223> OTHER INFORMATION: PCR amplification primer for pGHV-gpB gene
      sequences

<400> SEQUENCE: 3
mgaacaacgt yaaytgyga                                                19

<210> SEQ ID NO 4
<211> LENGTH: 19
<212> TYPE: DNA
<213> ORGANISM: Artificial Sequence
<220> FEATURE:
<223> OTHER INFORMATION: PCR amplification primer for pGHV-gpB gene
      sequences

<400> SEQUENCE: 4
mgaacaacgt yaaytgyct                                                19

<210> SEQ ID NO 5
<211> LENGTH: 17
<212> TYPE: DNA
<213> ORGANISM: Artificial Sequence
<220> FEATURE:
<223> OTHER INFORMATION: PCR amplification primer for pGHV-gpB gene
      sequences

<400> SEQUENCE: 5
```

```
mgaacaacgt yaaytgy                                                17
```

<210> SEQ ID NO 6
<211> LENGTH: 19
<212> TYPE: DNA
<213> ORGANISM: Artificial Sequence
<220> FEATURE:
<223> OTHER INFORMATION: PCR amplification primer for pGHV-gpB gene
      sequences

<400> SEQUENCE: 6

```
cartcartwt gcmtaygac                                              19
```

<210> SEQ ID NO 7
<211> LENGTH: 19
<212> TYPE: DNA
<213> ORGANISM: Artificial Sequence
<220> FEATURE:
<223> OTHER INFORMATION: PCR amplification primer for pGHV-gpB gene
      sequences
<221> NAME/KEY: misc_feature
<223> OTHER INFORMATION: n=i

<400> SEQUENCE: 7

```
carntncart wtgcmtayg                                              19
```

<210> SEQ ID NO 8
<211> LENGTH: 20
<212> TYPE: DNA
<213> ORGANISM: Artificial Sequence
<220> FEATURE:
<223> OTHER INFORMATION: PCR amplification primer for pGHV-gpB gene
      sequences

<400> SEQUENCE: 8

```
gtbatgwsha gvathtaygg                                             20
```

<210> SEQ ID NO 9
<211> LENGTH: 20
<212> TYPE: DNA
<213> ORGANISM: Artificial Sequence
<220> FEATURE:
<223> OTHER INFORMATION: PCR amplification primer for pGHV-gpB gene
      sequences

<400> SEQUENCE: 9

```
gtbatgwshg cvathtaygg                                             20
```

<210> SEQ ID NO 10
<211> LENGTH: 20
<212> TYPE: DNA
<213> ORGANISM: Artificial Sequence
<220> FEATURE:
<223> OTHER INFORMATION: PCR amplification primer for pGHV-gpB gene
      sequences
<221> NAME/KEY: misc_feature
<223> OTHER INFORMATION: n=i

<400> SEQUENCE: 10

```
swcatnacrs tngtnggrtt                                             20
```

<210> SEQ ID NO 11
<211> LENGTH: 26
<212> TYPE: DNA
<213> ORGANISM: Artificial Sequence
<220> FEATURE:
<223> OTHER INFORMATION: PCR amplification primer for pGHV-gpB gene
      sequences

```
<221> NAME/KEY: misc_feature
<223> OTHER INFORMATION: n=i

<400> SEQUENCE: 11
trngygtart arttrtaytc yctraa                                              26

<210> SEQ ID NO 12
<211> LENGTH: 21
<212> TYPE: DNA
<213> ORGANISM: Artificial Sequence
<220> FEATURE:
<223> OTHER INFORMATION: PCR amplification primer for pGHV-gpB gene
      sequences

<400> SEQUENCE: 12
gtartarttr taytcyctra a                                                   21

<210> SEQ ID NO 13
<211> LENGTH: 21
<212> TYPE: DNA
<213> ORGANISM: Artificial Sequence
<220> FEATURE:
<223> OTHER INFORMATION: PCR amplification primer for pGHV-gpB gene
      sequences

<400> SEQUENCE: 13
ctgraarttr taytcycgra a                                                   21

<210> SEQ ID NO 14
<211> LENGTH: 26
<212> TYPE: DNA
<213> ORGANISM: Artificial Sequence
<220> FEATURE:
<223> OTHER INFORMATION: PCR amplification primer for pGHV-gpB gene
      sequences
<221> NAME/KEY: misc_feature
<223> OTHER INFORMATION: n=i

<400> SEQUENCE: 14
tgngyctgra arttrtaytc ycgraa                                              26

<210> SEQ ID NO 15
<211> LENGTH: 20
<212> TYPE: DNA
<213> ORGANISM: Artificial Sequence
<220> FEATURE:
<223> OTHER INFORMATION: PCR amplification primer for Epstein-Barr Virus
      genome

<400> SEQUENCE: 15
agaactaccg tcaactgcct                                                     20

<210> SEQ ID NO 16
<211> LENGTH: 18
<212> TYPE: DNA
<213> ORGANISM: Artificial Sequence
<220> FEATURE:
<223> OTHER INFORMATION: PCR amplification primer for Epstein-Barr Virus
      genome

<400> SEQUENCE: 16
agaactaccg tcaactgc                                                       18

<210> SEQ ID NO 17
<211> LENGTH: 21
<212> TYPE: DNA
<213> ORGANISM: Artificial Sequence
```

```
<220> FEATURE:
<223> OTHER INFORMATION: PCR amplification primer for Epstein-Barr Virus
      genome

<400> SEQUENCE: 17
cagatccaat tgcctacga c                                              21

<210> SEQ ID NO 18
<211> LENGTH: 19
<212> TYPE: DNA
<213> ORGANISM: Artificial Sequence
<220> FEATURE:
<223> OTHER INFORMATION: PCR amplification primer for Epstein-Barr Virus
      genome

<400> SEQUENCE: 18
cagatccaat tgcctacg                                                 19

<210> SEQ ID NO 19
<211> LENGTH: 20
<212> TYPE: DNA
<213> ORGANISM: Artificial Sequence
<220> FEATURE:
<223> OTHER INFORMATION: PCR amplification primer for Epstein-Barr Virus
      genome

<400> SEQUENCE: 19
gtcatgtcca gcatctacgg                                               20

<210> SEQ ID NO 20
<211> LENGTH: 20
<212> TYPE: DNA
<213> ORGANISM: Artificial Sequence
<220> FEATURE:
<223> OTHER INFORMATION: PCR amplification primer for Epstein-Barr Virus
      genome

<400> SEQUENCE: 20
gacatgacgg tggttggatt                                               20

<210> SEQ ID NO 21
<211> LENGTH: 26
<212> TYPE: DNA
<213> ORGANISM: Artificial Sequence
<220> FEATURE:
<223> OTHER INFORMATION: PCR amplification primer for Epstein-Barr Virus
      genome

<400> SEQUENCE: 21
tgcgcctgga agttgtactc ccggaa                                        26

<210> SEQ ID NO 22
<211> LENGTH: 21
<212> TYPE: DNA
<213> ORGANISM: Artificial Sequence
<220> FEATURE:
<223> OTHER INFORMATION: PCR amplification primer for Epstein-Barr Virus
      genome

<400> SEQUENCE: 22
ctggaagttg tactcccgga a                                             21

<210> SEQ ID NO 23
<211> LENGTH: 2598
<212> TYPE: DNA
<213> ORGANISM: Artificial Sequence
<220> FEATURE:
```

-continued

<223> OTHER INFORMATION: cDNA for porcine gamma herpesvirus gpB gene

<400> SEQUENCE: 23

```
atggcaggta gcttaaaact taggggatct gttctagcac tgtggtacct gtatcaggtg     60
gctctttatt cacttagtat agcagagacc ggtgtaacct cacctccaaa tacagcgacc    120
tggtctactg aatcgccgct aacaggtcac tatggaacac acgattcaag ccatggtgaa    180
agaggaaaca acgaaaacag agattcagaa gagcaaaata aaaacattta tggatcgcct    240
tctacgtttc cttacagagt atgcagtgcc tccggagttg gagatgtctt tagatttcag    300
accgaccatg tgtgtcccga tgccagtgat atggtacaca gtgaggggat tctactaatt    360
tacaaacaga acattattcc atttatgttt agagttagga aatatagaaa agttgttaca    420
acaagtactg tctacaatgg tatttattct gactctatta ccaaccaaca tactttctat    480
aaatcaatcg aaccttggga gacagaaaag atggacacaa tatatcagtg ttttaattct    540
ttaagactaa acacaggtgg aaatctgctt acttatgtag atagagatga tataaatatg    600
acagtgtttc tgcaacctgt tgacggtgtg acgcccgatg tgaagaggta tggcagtcaa    660
ccagagctgt accttgaacc tggctggttt tggggtagtt atagaagacg aactacagtg    720
aactgtgaac taatggacat gtttgcaaga tcaaatcctc catttgattt ctttgttaca    780
gctacaggtg atacggtgga aatgtctcca ttttggagtg gtgaagatga tcatgaaaat    840
aagatgcacg agaagccatg gtttgttagt gtgataaata actacaaggt ggtggactat    900
caaaacagag ggactgtacc ccttggaaaa acaaggatat ttctagatag ggaagagtat    960
acattatctt gggaaaagca tctaaaaaat atgtcatatt gtccactaac attatggaaa   1020
gcattttaca atggaatcca gacggagcat tcaggctcat atcattttgt agccaatgac   1080
atcacagcgt cattcacaac tagtaaagaa gacatgaaag agttcaatac gacatatcat   1140
tgtctcaacg aggaaataaa ggcagaaata gagaagaaat atgcaaaagt aaactcaact   1200
cactctaaat atggagatct gaaatacttt aaaacagatg ggggtctcta tttagtctgg   1260
caacctctta ttcaaaacag gcttcttgat gctaagaaca aactgaacaa tgagacttat   1320
tccaggagat cacgacgtca ggcagaatct actactgacc caatgatgga gatgactgga   1380
aatggagcag gtggagaata tagcagtgaa aattcaatca cggtggcgca ggtgcagtat   1440
gcctatgaca atcttcgtat cagaataaat aacattttgg aagatttgtc aaaggcatgg   1500
tgtcgtgagc agcatagagc tgctctggtg tggaatgagc tcagcaagat taatcccaca   1560
agcgtcatga gcatgattta caatagaccc gtatcagcca aaagaatagg agatgtcatt   1620
tcagtctcta actgtattgt ggtagaccaa accagtgtct cattacataa aagtctcagg   1680
cttctcagtg catcggatga aaagtgcttc tctagacctc cagtgacatt taagtttatg   1740
aatgacagta ctatttacaa agggcaacta ggagtcaata atgagattct cttaaccaca   1800
acatacettg aaacatgtca ggaaaacact gagtattact ttcaggcaaa gacagacatg   1860
tacatttaca aaaactatga gcatttgaag actgtgcctt tatcttcgat caccacacta   1920
gatacattta tagcccttaa ttttacacta ttggagaatg ttgactttaa agtcattgaa   1980
ctttatacca gggacgagaa gaggcttagt aatgtctttg acattgaaac aatgtttagg   2040
gaatataact actatgctca gagggtcagt ggcctcagaa aggatttgct ggatctaagc   2100
accaatagaa atcaatttgt ggatgcattt ggtagtctta tggatgattt gggtgctgtt   2160
gggcagacag ttgtaaatgc tgtaagtggt gtggctacgc tgtttagctc aattgtaaca   2220
ggatttatta atttcattaa aaacccattt ggtggaatgt taatgattat tgttgttatt   2280
```

```
ggtgtgctat ttgccatcta ctttctgacc aaaaagacga agatatatga gacggcaccg    2340
attaagatga tttatcctga aattgacaag ctgaaagaac gtgagggaaa atcagaaata    2400
gcaccaatca gtgaagaaga gctggagaga attgtacttg ctatgcacat ccatcaacaa    2460
aattcacata tggaaacaaa aacaaggaag gatcccaaag acagcatatt aacaagggca    2520
caaaatatgc tacgcaaaag atcaggatat tctaatttaa aaaatgctga atctgtggag    2580
atgttaaaca ctttataa                                                  2598
```

<210> SEQ ID NO 24
<211> LENGTH: 865
<212> TYPE: PRT
<213> ORGANISM: Artificial Sequence
<220> FEATURE:
<223> OTHER INFORMATION: Deduced amino acid sequence of porcine gamma
      herpesvirus gpB gene

<400> SEQUENCE: 24

```
Met Ala Gly Ser Leu Lys Leu Arg Gly Ser Val Leu Ala Leu Trp Tyr
1               5                   10                  15

Leu Tyr Gln Val Ala Leu Tyr Ser Leu Ser Ile Ala Glu Thr Gly Val
                20                  25                  30

Thr Ser Pro Pro Asn Thr Ala Thr Trp Ser Thr Glu Ser Pro Leu Thr
            35                  40                  45

Gly His Tyr Gly Thr His Asp Ser Ser His Gly Glu Arg Gly Asn Asn
        50                  55                  60

Glu Asn Arg Asp Ser Glu Glu Gln Asn Lys Asn Ile Tyr Gly Ser Pro
65                  70                  75                  80

Ser Thr Phe Pro Tyr Arg Val Cys Ser Ala Ser Gly Val Gly Asp Val
                85                  90                  95

Phe Arg Phe Gln Thr Asp His Val Cys Pro Asp Ala Ser Asp Met Val
                100                 105                 110

His Ser Glu Gly Ile Leu Leu Ile Tyr Lys Gln Asn Ile Ile Pro Phe
            115                 120                 125

Met Phe Arg Val Arg Lys Tyr Arg Lys Val Val Thr Thr Ser Thr Val
        130                 135                 140

Tyr Asn Gly Ile Tyr Ser Asp Ser Ile Thr Asn Gln His Thr Phe Tyr
145                 150                 155                 160

Lys Ser Ile Glu Pro Trp Glu Thr Glu Lys Met Asp Thr Ile Tyr Gln
                165                 170                 175

Cys Phe Asn Ser Leu Arg Leu Asn Thr Gly Gly Asn Leu Leu Thr Tyr
                180                 185                 190

Val Asp Arg Asp Asp Ile Asn Met Thr Val Phe Leu Gln Pro Val Asp
            195                 200                 205

Gly Val Thr Pro Asp Val Lys Arg Tyr Gly Ser Gln Pro Glu Leu Tyr
        210                 215                 220

Leu Glu Pro Gly Trp Phe Trp Gly Ser Tyr Arg Arg Arg Thr Thr Val
225                 230                 235                 240

Asn Cys Glu Leu Met Asp Met Phe Ala Arg Ser Asn Pro Pro Phe Asp
                245                 250                 255

Phe Phe Val Thr Ala Thr Gly Asp Thr Val Glu Met Ser Pro Phe Trp
                260                 265                 270

Ser Gly Glu Asp Asp His Glu Asn Lys Met His Glu Lys Pro Trp Phe
            275                 280                 285

Val Ser Val Ile Asn Asn Tyr Lys Val Val Asp Tyr Gln Asn Arg Gly
```

-continued

```
                290                 295                 300
Thr Val Pro Leu Gly Lys Thr Arg Ile Phe Leu Asp Arg Glu Glu Tyr
305                 310                 315                 320

Thr Leu Ser Trp Glu Lys His Leu Lys Asn Met Ser Tyr Cys Pro Leu
                325                 330                 335

Thr Leu Trp Lys Ala Phe Tyr Asn Gly Ile Gln Thr Glu His Ser Gly
                340                 345                 350

Ser Tyr His Phe Val Ala Asn Asp Ile Thr Ala Ser Phe Thr Thr Ser
                355                 360                 365

Lys Glu Asp Met Lys Glu Phe Asn Thr Thr Tyr His Cys Leu Asn Glu
370                 375                 380

Glu Ile Lys Ala Glu Ile Glu Lys Lys Tyr Ala Lys Val Asn Ser Thr
385                 390                 395                 400

His Ser Lys Tyr Gly Asp Leu Lys Tyr Phe Lys Thr Asp Gly Gly Leu
                405                 410                 415

Tyr Leu Val Trp Gln Pro Leu Ile Gln Asn Arg Leu Leu Asp Ala Lys
                420                 425                 430

Asn Lys Leu Asn Asn Glu Thr Tyr Ser Arg Arg Ser Arg Arg Gln Ala
                435                 440                 445

Glu Ser Thr Thr Asp Pro Met Met Glu Met Thr Gly Asn Gly Ala Gly
                450                 455                 460

Gly Glu Tyr Ser Ser Glu Asn Ser Ile Thr Val Ala Gln Val Gln Tyr
465                 470                 475                 480

Ala Tyr Asp Asn Leu Arg Ile Arg Ile Asn Asn Ile Leu Glu Asp Leu
                485                 490                 495

Ser Lys Ala Trp Cys Arg Glu Gln His Arg Ala Ala Leu Val Trp Asn
                500                 505                 510

Glu Leu Ser Lys Ile Asn Pro Thr Ser Val Met Ser Met Ile Tyr Asn
                515                 520                 525

Arg Pro Val Ser Ala Lys Arg Ile Gly Asp Val Ile Ser Val Ser Asn
                530                 535                 540

Cys Ile Val Val Asp Gln Thr Ser Val Ser Leu His Lys Ser Leu Arg
545                 550                 555                 560

Leu Leu Ser Ala Ser Asp Glu Lys Cys Phe Ser Arg Pro Pro Val Thr
                565                 570                 575

Phe Lys Phe Met Asn Asp Ser Thr Ile Tyr Lys Gly Gln Leu Gly Val
                580                 585                 590

Asn Asn Glu Ile Leu Leu Thr Thr Thr Tyr Leu Glu Thr Cys Gln Glu
                595                 600                 605

Asn Thr Glu Tyr Tyr Phe Gln Ala Lys Thr Asp Met Tyr Ile Tyr Lys
610                 615                 620

Asn Tyr Glu His Leu Lys Thr Val Pro Leu Ser Ser Ile Thr Thr Leu
625                 630                 635                 640

Asp Thr Phe Ile Ala Leu Asn Phe Thr Leu Leu Glu Asn Val Asp Phe
                645                 650                 655

Lys Val Ile Glu Leu Tyr Thr Arg Asp Glu Lys Arg Leu Ser Asn Val
                660                 665                 670

Phe Asp Ile Glu Thr Met Phe Arg Glu Tyr Asn Tyr Tyr Ala Gln Arg
                675                 680                 685

Val Ser Gly Leu Arg Lys Asp Leu Leu Asp Leu Ser Thr Asn Arg Asn
                690                 695                 700

Gln Phe Val Asp Ala Phe Gly Ser Leu Met Asp Asp Leu Gly Ala Val
705                 710                 715                 720
```

```
Gly Gln Thr Val Val Asn Ala Val Ser Gly Val Ala Thr Leu Phe Ser
                725                 730                 735

Ser Ile Val Thr Gly Phe Ile Asn Phe Ile Lys Asn Pro Phe Gly Gly
            740                 745                 750

Met Leu Met Ile Ile Val Val Ile Gly Val Leu Phe Ala Ile Tyr Phe
        755                 760                 765

Leu Thr Lys Thr Lys Ile Tyr Glu Thr Ala Pro Ile Lys Met Ile
    770                 775                 780

Tyr Pro Glu Ile Asp Lys Leu Lys Glu Arg Glu Gly Lys Ser Glu Ile
785                 790                 795                 800

Ala Pro Ile Ser Glu Glu Leu Glu Arg Ile Val Leu Ala Met His
                805                 810                 815

Ile His Gln Gln Asn Ser His Met Glu Thr Lys Thr Arg Lys Asp Pro
                820                 825                 830

Lys Asp Ser Ile Leu Thr Arg Ala Gln Asn Met Leu Arg Lys Arg Ser
                835                 840                 845

Gly Tyr Ser Asn Leu Lys Asn Ala Glu Ser Val Glu Met Leu Asn Thr
    850                 855                 860

Leu
865

<210> SEQ ID NO 25
<211> LENGTH: 24
<212> TYPE: DNA
<213> ORGANISM: Artificial Sequence
<220> FEATURE:
<223> OTHER INFORMATION: Sequencing primer for TOPO-pCRII: bases 434-458

<400> SEQUENCE: 25
cgccagggtt ttcccagtca cgac                                              24

<210> SEQ ID NO 26
<211> LENGTH: 17
<212> TYPE: DNA
<213> ORGANISM: Artificial Sequence
<220> FEATURE:
<223> OTHER INFORMATION: M13 reverse sequencing primer for TOPO-pCRII:
      bases 205-222

<400> SEQUENCE: 26
caggaaacag ctatgac                                                      17

<210> SEQ ID NO 27
<211> LENGTH: 20
<212> TYPE: DNA
<213> ORGANISM: Artificial Sequence
<220> FEATURE:
<223> OTHER INFORMATION: Sequencing primer for porcine gamma herpesvirus
      gpB gene: bases 1989-2008

<400> SEQUENCE: 27
cagggacgag aagaggctta                                                   20

<210> SEQ ID NO 28
<211> LENGTH: 19
<212> TYPE: DNA
<213> ORGANISM: Artificial Sequence
<220> FEATURE:
<223> OTHER INFORMATION: Sequencing primer for porcine gamma herpesvirus
      gpB gene: bases 1513-1531

<400> SEQUENCE: 28
```
acaccagagc agctctatg                                                19

<210> SEQ ID NO 29
<211> LENGTH: 24
<212> TYPE: DNA
<213> ORGANISM: Artificial Sequence
<220> FEATURE:
<223> OTHER INFORMATION: Sequencing primer for porcine gamma herpesvirus
      gpB gene: bases 2399-2422

<400> SEQUENCE: 29
tagcaccaat cagtgaagaa gagc                                          24

<210> SEQ ID NO 30
<211> LENGTH: 22
<212> TYPE: DNA
<213> ORGANISM: Artificial Sequence
<220> FEATURE:
<223> OTHER INFORMATION: Sequencing primer for porcine gamma herpesvirus
      gpB gene: bases 322-343

<400> SEQUENCE: 30
gccagtgata tggtacacag tg                                            22

<210> SEQ ID NO 31
<211> LENGTH: 24
<212> TYPE: DNA
<213> ORGANISM: Artificial Sequence
<220> FEATURE:
<223> OTHER INFORMATION: Sequencing primer for porcine gamma herpesvirus
      gpB gene: bases 140-163

<400> SEQUENCE: 31
taacaggtca ctatggaaca cacg                                          24

<210> SEQ ID NO 32
<211> LENGTH: 24
<212> TYPE: DNA
<213> ORGANISM: Artificial Sequence
<220> FEATURE:
<223> OTHER INFORMATION: Sequencing primer for porcine gamma herpesvirus
      gpB gene: bases 537-560

<400> SEQUENCE: 32
ttctttaaga ctaaacacag gtgg                                          24

<210> SEQ ID NO 33
<211> LENGTH: 21
<212> TYPE: DNA
<213> ORGANISM: Artificial Sequence
<220> FEATURE:
<223> OTHER INFORMATION: Sequencing primer for porcine gamma herpesvirus
      gpB gene: bases 815-835

<400> SEQUENCE: 33
ggagtggtga agatgatcat g                                             21

<210> SEQ ID NO 34
<211> LENGTH: 25
<212> TYPE: DNA
<213> ORGANISM: Artificial Sequence
<220> FEATURE:
<223> OTHER INFORMATION: Sequencing primer for porcine gamma herpesvirus
      gpB gene: bases 993-1017

<400> SEQUENCE: 34

-continued

```
ccataatgtt agtggacaat atgac                                      25
```

<210> SEQ ID NO 35
<211> LENGTH: 21
<212> TYPE: DNA
<213> ORGANISM: Artificial Sequence
<220> FEATURE:
<223> OTHER INFORMATION: Sequencing primer for porcine gamma herpesvirus
      gpB gene: bases 1073-1093

<400> SEQUENCE: 35

```
atgacgctgt gatgtcattg g                                          21
```

<210> SEQ ID NO 36
<211> LENGTH: 22
<212> TYPE: DNA
<213> ORGANISM: Artificial Sequence
<220> FEATURE:
<223> OTHER INFORMATION: Sequencing primer for porcine gamma herpesvirus
      gpB gene: bases 1673-1694

<400> SEQUENCE: 36

```
gatgcactga gaagcctgag ac                                         22
```

<210> SEQ ID NO 37
<211> LENGTH: 823
<212> TYPE: PRT
<213> ORGANISM: Human herpesvirus 8

<400> SEQUENCE: 37

```
Met Thr Pro Arg Ser Arg Leu Ala Thr Leu Gly Thr Val Ile Leu Leu
 1               5                  10                  15

Val Cys Phe Cys Ala Gly Ala Ala His Ser Arg Gly Asp Thr Phe Gln
            20                  25                  30

Thr Ser Ser Ser Pro Thr Pro Pro Gly Ser Ser Ser Lys Ala Pro Thr
        35                  40                  45

Lys Pro Gly Glu Glu Ala Ser Gly Pro Lys Ser Val Asp Phe Tyr Gln
    50                  55                  60

Phe Arg Val Cys Ser Ala Ser Ile Thr Gly Glu Leu Phe Arg Phe Asn
65                  70                  75                  80

Leu Glu Gln Thr Cys Pro Asp Thr Lys Asp Lys Tyr His Gln Glu Gly
                85                  90                  95

Ile Leu Leu Val Tyr Lys Lys Asn Ile Val Pro His Ile Phe Lys Val
            100                 105                 110

Arg Arg Tyr Arg Lys Ile Ala Thr Ser Val Thr Val Tyr Arg Gly Leu
        115                 120                 125

Thr Glu Ser Ala Ile Thr Asn Lys Tyr Glu Leu Pro Arg Pro Val Pro
    130                 135                 140

Leu Tyr Glu Ile Ser His Met Asp Ser Thr Tyr Gln Cys Phe Ser Ser
145                 150                 155                 160

Met Lys Val Asn Val Asn Gly Val Glu Asn Thr Phe Thr Asp Arg Asp
                165                 170                 175

Asp Val Asn Thr Thr Val Phe Leu Gln Pro Val Glu Gly Leu Thr Asp
            180                 185                 190

Asn Ile Gln Arg Tyr Phe Ser Gln Pro Val Ile Tyr Ala Glu Pro Gly
        195                 200                 205

Trp Phe Pro Gly Ile Tyr Arg Val Arg Thr Thr Val Asn Cys Glu Ile
    210                 215                 220

Val Asp Met Ile Ala Arg Ser Ala Glu Pro Tyr Asn Tyr Phe Val Thr
```

-continued

```
            225                 230                 235                 240
Ser Leu Gly Asp Thr Val Glu Val Ser Pro Phe Cys Tyr Asn Glu Ser
                245                 250                 255
Ser Cys Ser Thr Thr Pro Ser Asn Lys Asn Gly Leu Ser Val Gln Val
                260                 265                 270
Val Leu Asn His Thr Val Val Thr Tyr Ser Asp Arg Gly Thr Ser Pro
                275                 280                 285
Thr Pro Gln Asn Arg Ile Phe Val Glu Thr Gly Ala Tyr Thr Leu Ser
                290                 295                 300
Trp Ala Ser Glu Ser Lys Thr Thr Ala Val Cys Pro Leu Ala Leu Trp
305                 310                 315                 320
Lys Thr Phe Pro Arg Ser Ile Gln Thr Thr His Glu Asp Ser Phe His
                325                 330                 335
Phe Val Ala Asn Glu Ile Thr Ala Thr Phe Thr Ala Pro Leu Thr Pro
                340                 345                 350
Val Ala Asn Phe Thr Asp Thr Tyr Ser Cys Leu Thr Ser Asp Ile Asn
                355                 360                 365
Thr Thr Leu Asn Ala Ser Lys Ala Lys Leu Ala Ser Thr His Val Pro
                370                 375                 380
Asn Gly Thr Val Gln Tyr Phe His Thr Gly Gly Leu Tyr Leu Val
385                 390                 395                 400
Trp Gln Pro Met Ser Ala Ile Asn Leu Thr His Ala Gln Gly Asp Ser
                405                 410                 415
Gly Asn Pro Thr Ser Ser Pro Pro Ser Ala Ser Pro Met Thr Thr
                420                 425                 430
Ser Ala Ser Arg Arg Lys Arg Ser Ala Ser Thr Ala Ala Ala Gly
                435                 440                 445
Gly Gly Gly Ser Thr Asp Asn Leu Ser Tyr Thr Gln Leu Gln Phe Ala
                450                 455                 460
Tyr Asp Lys Leu Arg Asp Gly Ile Asn Gln Val Leu Glu Glu Leu Ser
465                 470                 475                 480
Arg Ala Trp Cys Arg Glu Gln Val Arg Asp Asn Leu Met Trp Tyr Glu
                485                 490                 495
Leu Ser Lys Ile Asn Pro Thr Ser Val Met Thr Ala Ile Tyr Gly Arg
                500                 505                 510
Pro Val Ser Ala Lys Phe Val Gly Asp Ala Ile Ser Val Thr Glu Cys
                515                 520                 525
Ile Asn Val Asp Gln Ser Ser Val Asn Ile His Lys Ser Leu Arg Thr
                530                 535                 540
Asn Ser Lys Asp Val Cys Tyr Ala Arg Pro Leu Val Thr Phe Lys Phe
545                 550                 555                 560
Leu Asn Ser Ser Asn Leu Phe Thr Gly Gln Leu Gly Ala Arg Asn Glu
                565                 570                 575
Ile Ile Leu Thr Asn Asn Gln Val Glu Thr Cys Lys Asp Thr Cys Glu
                580                 585                 590
His Tyr Phe Ile Thr Arg Asn Glu Thr Leu Val Tyr Lys Asp Tyr Ala
                595                 600                 605
Tyr Leu Arg Thr Ile Asn Thr Thr Asp Ile Ser Thr Leu Asn Thr Phe
                610                 615                 620
Ile Ala Leu Asn Leu Ser Phe Ile Gln Asn Ile Asp Phe Lys Ala Ile
625                 630                 635                 640
Glu Leu Tyr Ser Ser Ala Glu Lys Arg Leu Ala Ser Ser Val Phe Asp
                645                 650                 655
```

-continued

```
Leu Glu Thr Met Phe Arg Glu Tyr Asn Tyr Tyr Thr His Arg Leu Ala
            660                 665                 670

Gly Leu Arg Glu Asp Leu Asp Asn Thr Ile Asp Met Asn Lys Glu Arg
        675                 680                 685

Phe Val Arg Asp Leu Ser Glu Ile Val Ala Asp Leu Gly Gly Ile Gly
    690                 695                 700

Lys Thr Val Val Asn Val Ala Ser Ser Val Val Thr Leu Cys Gly Ser
705                 710                 715                 720

Leu Val Thr Gly Phe Ile Asn Phe Ile Lys His Pro Leu Gly Gly Met
                725                 730                 735

Leu Met Ile Ile Ile Val Ile Ala Ile Ile Leu Ile Ile Phe Met Leu
            740                 745                 750

Ser Arg Arg Thr Asn Thr Ile Ala Gln Ala Pro Val Lys Met Ile Tyr
        755                 760                 765

Pro Asp Val Asp Arg Arg Ala Pro Pro Ser Gly Gly Ala Pro Thr Arg
    770                 775                 780

Glu Glu Ile Lys Asn Ile Leu Leu Gly Met His Gln Leu Gln Gln Glu
785                 790                 795                 800

Arg Gln Lys Ala Asp Asp Leu Lys Lys Ser Thr Pro Ser Val Phe Gln
                805                 810                 815

Arg Thr Ala Asn Gly Leu Arg
            820

<210> SEQ ID NO 38
<211> LENGTH: 808
<212> TYPE: PRT
<213> ORGANISM: Rhesus monkey rhadinovirus

<400> SEQUENCE: 38

Met Met Ile Thr Asn Arg Thr Arg Arg Leu Leu Arg Ala Trp Val Val
1               5                   10                  15

Ile Ile Ala Ile Gly Thr Ala Val Gly Glu Asn Val Thr Thr Pro Lys
            20                  25                  30

Gly Ala Thr Thr Thr Ala Lys Pro Thr Pro Gly Pro Ser Thr Pro Thr
        35                  40                  45

Pro Pro Glu Asn Pro Pro Arg Ala Glu Ala Phe Lys Phe Arg Val Cys
    50                  55                  60

Ser Ala Ser Ala Thr Gly Glu Leu Phe Arg Phe Asn Leu Glu Lys Thr
65                  70                  75                  80

Cys Pro Gly Thr Glu Asp Lys Thr His Gln Glu Gly Ile Leu Met Val
                85                  90                  95

Phe Lys Lys Asn Ile Val Pro His Ile Phe Lys Val Arg Arg Tyr Arg
            100                 105                 110

Lys Val Ala Thr Ser Val Thr Val Tyr Arg Gly Trp Thr Glu Thr Ala
        115                 120                 125

Val Thr Gly Lys Gln Glu Val Ile Arg Pro Val Pro Gln Tyr Glu Ile
    130                 135                 140

Asn His Met Asp Thr Thr Tyr Gln Cys Phe Ser Ser Met Arg Val Asn
145                 150                 155                 160

Val Asn Gly Ile Val Asn Thr Tyr Thr Asp Arg Asp Phe Thr Asn Gln
                165                 170                 175

Thr Val Phe Leu Gln Pro Val Glu Gly Leu Thr Asp Asn Ile Gln Arg
            180                 185                 190

Tyr Phe Ser Gln Pro Val Leu Tyr Thr Thr Pro Gly Trp Phe Pro Gly
```

-continued

```
            195                 200                 205
Ile Tyr Arg Val Arg Thr Thr Val Asn Cys Glu Ile Val Asp Met Ile
            210                 215                 220
Ala Arg Ser Ala Glu Pro Tyr Ser Tyr Phe Val Thr Ala Leu Gly Asp
225                 230                 235                 240
Thr Val Glu Val Ser Pro Phe Cys His Asn Asp Ser Thr Cys Ser Val
                    245                 250                 255
Ala Glu Lys Thr Glu Asn Gly Leu Gly Ala Arg Val Leu Thr Asn Tyr
                260                 265                 270
Thr Met Val Asp Phe Ala Thr Arg Ala Pro Thr Thr Glu Thr Arg Val
            275                 280                 285
Phe Ala Asp Ser Gly Glu Tyr Thr Val Ser Trp Lys Ala Glu Asp Pro
        290                 295                 300
Lys Ser Ala Val Cys Ala Leu Thr Leu Trp Lys Thr Phe Pro Arg Ala
305                 310                 315                 320
Ile Gln Thr Thr His Glu Ala Ser Tyr His Phe Val Ala Asn Asp Val
                    325                 330                 335
Thr Ala Thr Phe Thr Ser Pro Leu Ser Glu Val Ala Asn Phe Thr Gly
                340                 345                 350
Thr Tyr Ser Cys Leu Asp Glu Val Ile Gln Lys Thr Leu Asn Asp Thr
            355                 360                 365
Ile Lys Lys Leu Ser Asp Thr His Val Thr Asn Gly Ser Ala Gln Tyr
        370                 375                 380
Tyr Lys Thr Glu Gly Gly Leu Phe Leu Leu Trp Gln Pro Leu Thr Pro
385                 390                 395                 400
Leu Ser Leu Val Asp Glu Met Arg Gly Leu Asn Gly Thr Thr Pro Ala
                    405                 410                 415
Pro Pro Ala Thr Thr Ser Thr Val Ser Arg Val Arg Arg Ser Val Asn
                420                 425                 430
Thr Asn Glu Gln Ala Thr Asp Asn Leu Ala Ala Pro Gln Leu Gln Phe
            435                 440                 445
Ala Tyr Asp Lys Leu Arg Ala Ser Ile Asn Lys Val Leu Glu Glu Leu
        450                 455                 460
Ser Arg Ala Trp Cys Arg Glu Gln Val Arg Asp Thr Tyr Met Trp Tyr
465                 470                 475                 480
Glu Leu Ser Lys Ile Asn Pro Thr Ser Val Met Thr Ala Ile Tyr Gly
                    485                 490                 495
Arg Pro Val Ser Ala Lys Phe Val Gly Asp Ala Ile Ser Val Thr Asp
                500                 505                 510
Cys Val Ala Val Asp Gln Ala Ser Val Ser Ile His Lys Ser Leu Arg
            515                 520                 525
Thr Ser Thr Pro Gly Met Cys Tyr Ser Arg Pro Val Thr Phe Arg
        530                 535                 540
Phe Leu Asn Ser Thr Thr Leu Phe Lys Gly Gln Leu Gly Pro Arg Asn
545                 550                 555                 560
Glu Ile Ile Leu Thr Asp Asn Gln Val Glu Ala Cys Lys Glu Thr Cys
                    565                 570                 575
Glu His Tyr Phe Ile Ala Ser Asn Val Thr Tyr Tyr Lys Asp Tyr
                580                 585                 590
Val Phe Val Lys Lys Ile Asn Thr Ser Glu Ile Ser Thr Leu Gly Thr
            595                 600                 605
Phe Ile Ala Leu Asn Leu Ser Phe Ile Glu Asn Ile Asp Phe Arg Val
        610                 615                 620
```

-continued

```
Ile Glu Leu Tyr Ser Arg Ala Glu Lys Lys Leu Ser Gly Ser Val Phe
625                 630                 635                 640

Asp Ile Glu Thr Met Phe Arg Glu Tyr Asn Tyr Thr Gln Arg Leu
                645                 650                 655

Ala Gly Leu Arg Glu Asp Leu Asp Asn Thr Ile Asp Leu Asn Arg Asp
                660                 665                 670

Arg Leu Ala Arg Asp Leu Ser Glu Ile Ala Asp Leu Gly Asp Val
                675                 680                 685

Gly Arg Thr Val Val Asn Val Ala Ser Ser Val Ile Thr Leu Phe Gly
                690                 695                 700

Ser Ile Val Ser Gly Phe Ile Asn Phe Ile Lys Ser Pro Phe Gly Gly
705                 710                 715                 720

Met Leu Met Ile Leu Val Ile Val Ala Val Leu Ile Val Phe Ala
                725                 730                 735

Leu Asn Arg Arg Thr Asn Ala Ile Ala Gln Ala Pro Ile Arg Met Ile
                740                 745                 750

Tyr Pro Asp Ile Asp Lys Met Gln Pro Ser Gly Gly Lys Val Asp Gln
                755                 760                 765

Glu Gln Ile Lys Asn Ile Leu Ala Gly Met His Gln Leu Gln Gln Glu
                770                 775                 780

Glu Arg Arg Arg Leu Asp Glu Gln Gln Arg Ser Ala Pro Ser Leu Phe
785                 790                 795                 800

Arg Arg Ala Ser Asp Gly Leu Lys
                805

<210> SEQ ID NO 39
<211> LENGTH: 831
<212> TYPE: PRT
<213> ORGANISM: Murine herpesvirus 68

<400> SEQUENCE: 39

Met Tyr Pro Thr Val Lys Ser Met Arg Val Ala His Leu Thr Asn Leu
1               5                   10                  15

Leu Thr Leu Leu Cys Leu Leu Cys His Thr His Leu Tyr Val Cys Gln
                20                  25                  30

Pro Thr Thr Leu Arg Gln Pro Ser Asp Met Thr Pro Ala Gln Asp Ala
            35                  40                  45

Pro Thr Glu Thr Pro Pro Leu Ser Thr Asn Thr Asn Arg Gly Phe
        50                  55                  60

Glu Tyr Phe Arg Val Cys Gly Val Ala Ala Thr Gly Glu Thr Phe Arg
65                  70                  75                  80

Phe Asp Leu Asp Lys Thr Cys Pro Ser Thr Gln Asp Lys Lys His Val
                85                  90                  95

Glu Gly Ile Leu Leu Val Tyr Lys Ile Asn Ile Val Pro Tyr Ile Phe
            100                 105                 110

Lys Ile Arg Arg Tyr Arg Lys Ile Ile Thr Gln Leu Thr Ile Trp Arg
        115                 120                 125

Gly Leu Thr Thr Ser Ser Val Thr Gly Lys Phe Glu Met Ala Thr Gln
    130                 135                 140

Ala His Glu Trp Glu Val Gly Asp Phe Asp Ser Ile Tyr Gln Cys Tyr
145                 150                 155                 160

Asn Ser Ala Thr Met Val Val Asn Asn Val Arg Gln Val Tyr Val Asp
                165                 170                 175

Arg Asp Gly Val Asn Lys Thr Val Asn Ile Arg Pro Val Asp Gly Leu
```

-continued

```
              180              185              190
Thr Gly Asn Ile Gln Arg Tyr Phe Ser Gln Pro Thr Leu Tyr Ser Glu
        195                  200              205
Pro Gly Trp Met Pro Gly Phe Tyr Arg Val Arg Thr Thr Val Asn Cys
    210                  215                  220
Glu Ile Val Asp Met Val Ala Arg Ser Met Asp Pro Tyr Asn Tyr Ile
225                  230                  235                  240
Ala Thr Ala Leu Gly Asp Ser Leu Glu Leu Ser Pro Phe Gln Thr Phe
                245                  250                  255
Asp Asn Thr Ser Gln Ser Thr Ala Pro Lys Arg Ala Asp Met Arg Val
            260                  265                  270
Arg Glu Val Lys Asn Tyr Lys Phe Val Asp Tyr Asn Asn Arg Gly Thr
        275                  280                  285
Ala Pro Ala Gly Gln Ser Arg Thr Phe Leu Glu Thr Pro Ser Ala Thr
    290                  295                  300
Tyr Ser Trp Lys Thr Ala Thr Arg Gln Thr Ala Thr Cys Asp Leu Val
305                  310                  315                  320
His Trp Lys Thr Phe Pro Arg Ala Ile Gln Thr Ala His Glu His Ser
                325                  330                  335
Tyr His Phe Val Ala Asn Glu Val Thr Ala Thr Phe Asn Thr Pro Leu
            340                  345                  350
Thr Glu Val Glu Asn Phe Thr Ser Thr Tyr Ser Cys Val Ser Asp Gln
        355                  360                  365
Ile Asn Lys Thr Ile Ser Glu Tyr Ile Gln Lys Leu Asn Asn Ser Tyr
    370                  375                  380
Val Ala Ser Gly Lys Thr Gln Tyr Phe Lys Thr Asp Gly Asn Leu Tyr
385                  390                  395                  400
Leu Ile Trp Gln Pro Leu Glu His Pro Glu Ile Glu Asp Ile Asp Glu
                405                  410                  415
Asp Ser Asp Pro Glu Pro Thr Pro Ala Pro Pro Lys Ser Thr Arg Arg
            420                  425                  430
Lys Arg Glu Ala Ala Asp Asn Gly Asn Ser Thr Ser Glu Val Ser Lys
        435                  440                  445
Gly Ser Glu Asn Pro Leu Ile Thr Ala Gln Ile Gln Phe Ala Tyr Asp
    450                  455                  460
Lys Leu Thr Thr Ser Val Asn Asn Val Leu Glu Glu Leu Ser Arg Ala
465                  470                  475                  480
Trp Cys Arg Glu Gln Val Arg Asp Thr Leu Met Trp Tyr Glu Leu Ser
                485                  490                  495
Lys Val Asn Pro Thr Ser Val Met Ser Ala Ile Tyr Gly Lys Pro Val
            500                  505                  510
Ala Ala Arg Tyr Val Gly Asp Ala Ile Ser Val Thr Asp Cys Ile Tyr
        515                  520                  525
Val Asp Gln Ser Ser Val Asn Ile His Gln Ser Leu Arg Leu Gln His
    530                  535                  540
Asp Lys Thr Thr Cys Tyr Ser Arg Pro Arg Val Thr Phe Lys Phe Ile
545                  550                  555                  560
Asn Ser Thr Asp Pro Leu Thr Gly Gln Leu Gly Pro Arg Lys Glu Ile
                565                  570                  575
Ile Leu Ser Asn Thr Asn Ile Glu Thr Cys Lys Asp Glu Ser Glu His
            580                  585                  590
Tyr Phe Ile Val Gly Glu Tyr Ile Tyr Tyr Lys Asn Tyr Ile Phe
        595                  600                  605
```

-continued

```
Glu Glu Lys Leu Asn Leu Ser Ser Ile Ala Thr Leu Asp Thr Phe Ile
    610                 615                 620

Ala Leu Asn Ile Ser Phe Ile Glu Asn Ile Asp Phe Lys Thr Val Glu
625                 630                 635                 640

Leu Tyr Ser Ser Thr Glu Arg Lys Leu Ala Ser Ser Val Phe Asp Ile
                645                 650                 655

Glu Ser Met Phe Arg Glu Tyr Asn Tyr Thr Tyr Ser Leu Ala Gly
            660                 665                 670

Ile Lys Lys Asp Leu Asp Asn Thr Ile Asp Tyr Asn Arg Asp Arg Leu
            675                 680                 685

Val Gln Asp Leu Ser Asp Met Met Ala Asp Leu Gly Asp Ile Gly Arg
    690                 695                 700

Ser Val Val Asn Val Val Ser Ser Val Val Thr Phe Phe Ser Ser Ile
705                 710                 715                 720

Val Thr Gly Phe Ile Lys Phe Phe Thr Asn Pro Leu Gly Gly Ile Phe
                725                 730                 735

Ile Leu Leu Ile Ile Gly Gly Ile Ile Phe Leu Val Val Val Leu Asn
                740                 745                 750

Arg Arg Asn Ser Gln Phe His Asp Ala Pro Ile Lys Met Leu Tyr Pro
            755                 760                 765

Ser Val Glu Asn Tyr Ala Ala Arg Gln Ala Pro Pro Tyr Ser Ala
    770                 775                 780

Ser Pro Pro Ala Ile Asp Lys Glu Ile Lys Arg Ile Leu Leu Gly
785                 790                 795                 800

Met His Gln Val His Gln Glu Lys Glu Ala Gln Lys Gln Leu Thr
                805                 810                 815

Asn Ser Gly Pro Thr Leu Trp Gln Lys Ala Thr Gly Phe Leu Arg
            820                 825                 830

<210> SEQ ID NO 40
<211> LENGTH: 844
<212> TYPE: PRT
<213> ORGANISM: Bovine herpesvirus 4

<400> SEQUENCE: 40

Tyr Tyr Lys Thr Ile Leu Phe Phe Ala Leu Ile Lys Val Cys Ser Phe
1               5                   10                  15

Asn Gln Thr Thr Thr His Ser Thr Thr Thr Ser Pro Ser Ile Ser Ser
                20                  25                  30

Thr Thr Ser Ser Thr Thr Ser Thr Ser Lys Pro Ser Asn Thr Thr
            35                  40                  45

Ser Thr Asn Ser Ser Leu Ala Ala Ser Pro Gln Asn Thr Ser Thr Ser
    50                  55                  60

Lys Pro Ser Thr Asp Asn Gln Gly Thr Ser Thr Pro Thr Ile Pro Thr
65                  70                  75                  80

Val Thr Asp Asp Thr Ala Ser Lys Asn Phe Tyr Lys Tyr Arg Val Cys
                85                  90                  95

Ser Ala Ser Ser Ser Gly Glu Leu Phe Arg Phe Asp Leu Asp Gln
            100                 105                 110

Thr Cys Pro Asp Thr Lys Asp Lys Lys His Val Glu Gly Ile Leu Leu
            115                 120                 125

Val Leu Lys Lys Asn Ile Val Pro Tyr Ile Phe Lys Val Arg Lys Tyr
    130                 135                 140

Arg Lys Ile Ala Thr Ser Val Thr Val Tyr Arg Gly Trp Ser Gln Ala
```

```
                     145                 150                 155                 160
             Ala Val Thr Asn Arg Asp Asp Ile Ser Arg Ala Ile Pro Tyr Asn Glu
                             165                 170                 175
             Ile Ser Met Ile Asp Arg Thr Tyr His Cys Phe Ser Ala Met Ala Thr
                             180                 185                 190
             Val Ile Asn Gly Ile Leu Asn Thr Tyr Ile Asp Arg Asp Ser Glu Asn
                             195                 200                 205
             Lys Ser Val Pro Leu Gln Pro Val Ala Gly Leu Thr Glu Asn Ile Asn
                             210                 215                 220
             Arg Tyr Phe Ser Gln Pro Leu Ile Tyr Ala Glu Pro Gly Trp Phe Pro
             225                 230                 235                 240
             Gly Ile Tyr Arg Val Arg Thr Thr Val Asn Cys Glu Val Val Asp Met
                             245                 250                 255
             Tyr Ala Arg Ser Val Glu Pro Tyr Thr His Phe Ile Thr Ala Leu Gly
                             260                 265                 270
             Asp Thr Ile Glu Ile Ser Pro Phe Cys His Asn Asn Ser Gln Cys Thr
                             275                 280                 285
             Thr Gly Asn Ser Thr Ser Arg Asp Ala Thr Lys Val Trp Ile Glu Glu
                             290                 295                 300
             Asn His Gln Thr Val Asp Tyr Glu Arg Arg Gly His Pro Thr Lys Asp
             305                 310                 315                 320
             Lys Arg Ile Phe Leu Lys Asp Glu Glu Tyr Thr Ile Ser Trp Lys Ala
                             325                 330                 335
             Glu Asp Arg Glu Arg Ala Ile Cys Asp Phe Val Ile Trp Lys Thr Phe
                             340                 345                 350
             Pro Arg Ala Ile Gln Thr Ile His Asn Glu Ser Phe His Phe Val Ala
                             355                 360                 365
             Asn Glu Val Thr Ala Ser Phe Leu Thr Ser Asn Gln Glu Thr Glu
                             370                 375                 380
             Leu Arg Gly Asn Thr Glu Ile Leu Asn Cys Met Asn Ser Thr Ile Asn
             385                 390                 395                 400
             Glu Thr Leu Glu Glu Thr Val Lys Lys Phe Asn Lys Ser His Ile Arg
                             405                 410                 415
             Asp Gly Glu Val Lys Tyr Tyr Lys Thr Asn Gly Gly Leu Phe Leu Ile
                             420                 425                 430
             Trp Gln Ala Met Lys Pro Leu Asn Leu Ser Glu His Thr Asn Tyr Thr
                             435                 440                 445
             Ile Glu Arg Asn Asn Lys Thr Gly Asn Lys Ser Arg Gln Lys Arg Ser
                             450                 455                 460
             Val Asp Thr Lys Thr Phe Gln Gly Ala Lys Gly Leu Ser Thr Ala Gln
             465                 470                 475                 480
             Val Gln Tyr Ala Tyr Asp His Leu Arg Thr Ser Met Asn His Ile Leu
                             485                 490                 495
             Glu Glu Leu Thr Lys Thr Trp Cys Arg Glu Gln Lys Lys Asp Asn Leu
                             500                 505                 510
             Met Trp Tyr Glu Leu Ser Lys Ile Asn Pro Val Ser Val Met Ala Ala
                             515                 520                 525
             Ile Tyr Gly Lys Pro Val Ala Val Lys Ala Met Gly Asp Ala Phe Met
                             530                 535                 540
             Val Ser Glu Cys Ile Asn Val Asp Gln Ala Ser Val Asn Ile His Lys
             545                 550                 555                 560
             Ser Met Arg Thr Asp Asp Pro Lys Val Cys Tyr Ser Arg Pro Leu Val
                             565                 570                 575
```

```
Thr Phe Lys Phe Val Asn Ser Thr Ala Thr Phe Arg Gly Gln Leu Gly
            580                 585                 590

Thr Arg Asn Glu Ile Leu Leu Thr Asn Thr His Val Glu Thr Cys Arg
        595                 600                 605

Pro Thr Ala Asp His Tyr Phe Val Lys Asn Met Thr His Tyr Phe
    610                 615                 620

Lys Asp Tyr Lys Phe Val Lys Thr Met Asp Thr Asn Asn Ile Ser Thr
625                 630                 635                 640

Leu Asp Thr Phe Leu Thr Leu Asn Leu Thr Phe Ile Asp Asn Ile Asp
                645                 650                 655

Phe Lys Thr Val Glu Leu Tyr Ser Glu Thr Glu Arg Lys Met Ala Ser
                660                 665                 670

Ala Leu Asp Leu Glu Thr Met Phe Arg Glu Tyr Asn Tyr Tyr Thr Gln
                675                 680                 685

Lys Leu Ala Ser Leu Arg Glu Asp Leu Asp Asn Thr Ile Asp Leu Asn
                690                 695                 700

Arg Asp Arg Leu Val Lys Asp Leu Ser Glu Met Met Ala Asp Leu Gly
705                 710                 715                 720

Asp Ile Gly Lys Val Val Asn Thr Phe Ser Gly Ile Val Thr Val
                725                 730                 735

Phe Gly Ser Ile Val Gly Gly Phe Val Ser Phe Phe Thr Asn Pro Ile
                740                 745                 750

Gly Gly Val Thr Ile Ile Leu Leu Ile Val Val Val Phe Val Val
                755                 760                 765

Phe Ile Val Ser Arg Arg Thr Asn Asn Met Asn Glu Ala Pro Ile Lys
770                 775                 780

Met Ile Tyr Pro Asn Ile Asp Lys Ala Ser Glu Gln Glu Asn Ile Gln
785                 790                 795                 800

Pro Leu Pro Gly Glu Glu Ile Lys Arg Ile Leu Leu Gly Met His Gln
                805                 810                 815

Leu Gln Gln Ser Glu His Gly Lys Ser Glu Glu Ala Ser His Lys
                820                 825                 830

Pro Gly Leu Phe Gln Leu Leu Gly Asp Gly Leu Gln
                835                 840

<210> SEQ ID NO 41
<211> LENGTH: 791
<212> TYPE: PRT
<213> ORGANISM: Ateline herpesvirus 3

<400> SEQUENCE: 41

Met Thr Leu Asn Arg Cys Val Leu Leu Ile Val Leu Thr Phe Ser Thr
1               5                   10                  15

Ala Cys Ser Gln Thr Thr Pro Ala Ser Ser Asp Glu Asn Gly Lys Thr
                20                  25                  30

Pro Ala Ile Glu Lys Glu Tyr Phe Lys Tyr Arg Val Cys Ser Ala Ser
            35                  40                  45

Thr Thr Gly Glu Leu Phe Arg Phe Asn Leu Asp Arg Ala Cys Pro Ser
        50                  55                  60

Thr Glu Asp Lys Val His Arg Glu Gly Ile Leu Leu Val Tyr Lys Lys
65                  70                  75                  80

Asn Ile Val Pro His Ile Phe Lys Val Arg Arg Tyr Lys Lys Ile Ala
                85                  90                  95

Thr Ser Val Arg Ile Phe Asn Gly Trp Ser Arg Glu Gly Val Ala Ile
```

-continued

```
              100                 105                 110
Thr Asn Lys Trp Glu Leu Ser Arg Ala Val Pro Lys Tyr Glu Ile Asn
            115                 120                 125

Leu Met Asp Lys Asn Tyr Gln Cys His Asn Cys Met Gln Ile Glu Val
        130                 135                 140

Asn Gly Leu Leu Asn Ser Tyr Cys Asp Arg Asp Gly Asn Asn Lys Thr
145                 150                 155                 160

Val Asp Leu Lys Pro Val Asp Gly Leu Thr Gly Ala Ile Thr Arg Tyr
                165                 170                 175

Val Ser Gln Pro Lys Ile Phe Ala Asp Ala Gly Trp Leu Trp Gly Thr
            180                 185                 190

Tyr Lys Thr Arg Thr Thr Val Asn Cys Glu Ile Val Glu Met Phe Ala
        195                 200                 205

Arg Ser Ala Asp Pro Tyr Thr Tyr Phe Val Thr Ala Leu Gly Asp Thr
    210                 215                 220

Val Glu Val Ser Pro Phe Cys Asp Ala Glu Asn Ser Cys Pro Asn Ala
225                 230                 235                 240

Ser Asp Val Leu Ser Ser Gln Val Asp Phe Asn His Thr Val Val Asp
                245                 250                 255

Tyr Gly Asn Arg Ala Thr Ser Gln Gln His Gly Lys Arg Ile Phe Ala
            260                 265                 270

His Thr Leu Asp Tyr Ser Val Ser Trp Glu Ala Ile Asn Lys Thr Thr
        275                 280                 285

Ser Val Cys Ser Met Val Phe Trp Lys Gly Phe Gln Arg Ala Ile Gln
    290                 295                 300

Thr Glu His Asp Ser Thr Tyr His Phe Ile Ala Asn Glu Ile Thr Ala
305                 310                 315                 320

Gly Phe Ser Thr Ser Lys Glu Thr Leu Ala Ser Phe Ser Ser Glu Tyr
                325                 330                 335

Ser Cys Leu Met Ser Asp Ile Asn Ser Thr Leu Thr Asp Lys Ile Gly
            340                 345                 350

Arg Val Asn Asn Thr His Val Pro Asn Gly Thr Ala Gln Tyr Phe Lys
        355                 360                 365

Thr Glu Gly Gly Met Ile Leu Val Trp Gln Pro Leu Thr Ala Ile Glu
    370                 375                 380

Leu Glu Glu Ala Met Ile Glu Ala Thr Thr Val Ser Pro Thr Pro Leu
385                 390                 395                 400

Ser Thr Ala His Leu Thr Ser Arg Arg Thr Gly Arg Arg Lys Arg Asp
                405                 410                 415

Val Ser Ala Gly Ser Glu Asn Ser Val Leu Leu Ala Gln Ile Gln Tyr
            420                 425                 430

Ala Tyr Asp Lys Leu Arg Gln Ser Ile Asn Asn Val Leu Glu Glu Leu
        435                 440                 445

Ala Ile Thr Trp Cys Arg Glu Gln Val Arg Gln Thr Met Ile Trp Tyr
    450                 455                 460

Glu Ile Ala Lys Ile Asn Pro Thr Ser Val Met Thr Ala Ile Tyr Gly
465                 470                 475                 480

Lys Pro Val Ser Ala Lys Ala Leu Gly Asp Val Ile Ser Val Thr Glu
                485                 490                 495

Cys Ile Asn Val Asp Gln Thr Ser Val Ser Ile His Lys Ser Leu Lys
            500                 505                 510

Thr Thr Asn Asn Asp Val Cys Tyr Ser Arg Pro Pro Val Thr Phe Lys
        515                 520                 525
```

```
Phe Val Asn Ser Ser Gln Leu Phe Lys Gly Gln Leu Gly Ala Arg Asn
        530                 535                 540

Glu Ile Leu Leu Ser Glu Ser Leu Val Glu Asn Cys His Gln Asn Ala
545                 550                 555                 560

Glu His Phe Phe Thr Ala Lys Asn Glu Thr Tyr His Phe Lys Asn Tyr
                565                 570                 575

Leu His Val Glu Thr Leu Pro Leu Thr Asn Ile Ser Thr Leu Asp Thr
            580                 585                 590

Phe Leu Ala Leu Asn Leu Thr Phe Ile Glu Asn Ile Asp Phe Lys Ala
        595                 600                 605

Val Glu Leu Tyr Ser Ser Gly Glu Arg Lys Leu Ala Asn Val Phe Asp
    610                 615                 620

Leu Glu Thr Met Phe Arg Glu Tyr Asn Tyr Ala Gln Ser Ile Ser
625                 630                 635                 640

Gly Leu Arg Lys Asp Phe Asp Asn Ser Gln Arg Asn Asn Arg Asp Arg
                645                 650                 655

Ile Ile Gln Asp Phe Ser Glu Ile Leu Ala Asp Leu Gly Ser Ile Gly
                660                 665                 670

Lys Val Ile Val Asn Ile Ala Ser Ser Ala Phe Ser Leu Phe Gly Gly
                675                 680                 685

Ile Val Thr Gly Ile Leu Asn Phe Ile Lys Asn Pro Leu Gly Gly Met
            690                 695                 700

Leu Thr Phe Leu Leu Val Gly Ala Ile Ile Leu Val Ile Leu Leu
705                 710                 715                 720

Val Arg Arg Thr Asn Asn Met Ser Gln Ala Pro Ile Arg Met Ile Tyr
                725                 730                 735

Pro Asp Ile Glu Lys Ser Arg Ser Val Thr Pro Thr Glu Pro Glu
            740                 745                 750

Val Ile Lys Gln Ile Leu Leu Gly Met His Asn Met Gln Gln Glu Glu
            755                 760                 765

Tyr Lys Lys Arg Glu Glu His Lys Ala Ser Gln Pro Ser Phe Leu Lys
    770                 775                 780

Arg Ala Thr Asp Ala Phe Leu
785                 790

<210> SEQ ID NO 42
<211> LENGTH: 792
<212> TYPE: PRT
<213> ORGANISM: Herpesvirus saimiri

<400> SEQUENCE: 42

Met Val Pro Asn Lys His Leu Leu Ile Ile Leu Ser Phe Ser Thr
1               5                   10                  15

Ala Cys Gly Gln Thr Thr Pro Thr Thr Ala Val Glu Lys Asn Lys Thr
            20                  25                  30

Gln Ala Ile Tyr Gln Glu Tyr Phe Lys Tyr Arg Val Cys Ser Ala Ser
        35                  40                  45

Thr Thr Gly Glu Leu Phe Arg Phe Asp Leu Asp Arg Thr Cys Pro Ser
    50                  55                  60

Thr Glu Asp Lys Val His Lys Glu Gly Ile Leu Leu Val Tyr Lys Lys
65                  70                  75                  80

Asn Ile Val Pro Tyr Ile Phe Lys Val Arg Arg Tyr Lys Lys Ile Thr
                85                  90                  95

Thr Ser Val Arg Ile Phe Asn Gly Trp Thr Arg Glu Gly Val Ala Ile
```

```
                   100                 105                 110
Thr Asn Lys Trp Glu Leu Ser Arg Ala Val Pro Lys Tyr Glu Ile Asp
            115                 120                 125

Ile Met Asp Lys Thr Tyr Gln Cys His Asn Cys Met Gln Ile Glu Val
        130                 135                 140

Asn Gly Met Leu Asn Ser Tyr Tyr Asp Arg Asp Gly Asn Asn Lys Thr
145                 150                 155                 160

Val Asp Leu Lys Pro Val Asp Gly Leu Thr Gly Ala Ile Thr Arg Tyr
                165                 170                 175

Ile Ser Gln Pro Lys Val Phe Ala Asp Pro Gly Trp Leu Trp Gly Thr
            180                 185                 190

Tyr Arg Thr Arg Thr Thr Val Asn Cys Glu Ile Val Asp Met Phe Ala
        195                 200                 205

Arg Ser Ala Asp Pro Tyr Thr Tyr Phe Val Thr Ala Leu Gly Asp Thr
210                 215                 220

Val Glu Val Ser Pro Phe Cys Asp Val Asp Asn Ser Cys Pro Asn Ala
225                 230                 235                 240

Thr Asp Val Leu Ser Val Gln Ile Asp Leu Asn His Thr Val Val Asp
                245                 250                 255

Tyr Gly Asn Arg Ala Thr Ser Gln Gln His Lys Lys Arg Ile Phe Ala
            260                 265                 270

His Thr Leu Asp Tyr Ser Val Ser Trp Glu Ala Val Asn Lys Ser Ala
        275                 280                 285

Ser Val Cys Ser Met Val Phe Trp Lys Ser Phe Gln Arg Ala Ile Gln
        290                 295                 300

Thr Glu His Asp Leu Thr Tyr His Phe Ile Ala Asn Glu Ile Thr Ala
305                 310                 315                 320

Gly Phe Ser Thr Val Lys Glu Pro Leu Ala Asn Phe Thr Ser Asp Tyr
                325                 330                 335

Asn Cys Leu Met Thr His Ile Asn Thr Thr Leu Glu Asp Lys Ile Ala
            340                 345                 350

Arg Val Asn Asn Thr His Thr Pro Asn Gly Thr Ala Glu Tyr Tyr Gln
        355                 360                 365

Thr Glu Gly Gly Met Ile Leu Val Trp Gln Pro Leu Ile Ala Ile Glu
370                 375                 380

Leu Glu Glu Ala Met Leu Glu Ala Thr Thr Ser Pro Val Thr Pro Ser
385                 390                 395                 400

Ala Pro Thr Ser Ser Arg Ser Lys Arg Ala Ile Arg Ser Ile Arg
                405                 410                 415

Asp Val Ser Ala Gly Ser Glu Asn Asn Val Phe Leu Ser Gln Ile Gln
            420                 425                 430

Tyr Ala Tyr Asp Lys Leu Arg Gln Ser Ile Asn Asn Val Leu Glu Glu
        435                 440                 445

Leu Ala Ile Thr Trp Cys Arg Glu Gln Val Arg Gln Thr Met Val Trp
        450                 455                 460

Tyr Glu Ile Ala Lys Ile Asn Pro Thr Ser Val Met Thr Ala Ile Tyr
465                 470                 475                 480

Gly Lys Pro Val Ser Arg Lys Ala Leu Gly Asp Val Ile Ser Val Thr
                485                 490                 495

Glu Cys Ile Asn Val Asp Gln Ser Ser Val Ser Ile His Lys Ser Leu
            500                 505                 510

Lys Thr Glu Asn Asn Asp Ile Cys Tyr Ser Arg Pro Pro Val Thr Phe
        515                 520                 525
```

-continued

```
Lys Phe Val Asn Ser Ser Gln Leu Phe Lys Gly Gln Leu Gly Ala Arg
    530                 535                 540

Asn Glu Ile Leu Leu Ser Glu Ser Leu Val Glu Asn Cys His Gln Asn
545                 550                 555                 560

Ala Glu Thr Phe Phe Thr Ala Lys Asn Glu Thr Tyr His Phe Lys Asn
                565                 570                 575

Tyr Val His Val Glu Thr Leu Pro Val Asn Asn Ile Ser Thr Leu Asp
                580                 585                 590

Thr Phe Leu Ala Leu Asn Leu Thr Phe Ile Glu Asn Ile Asp Phe Lys
            595                 600                 605

Ala Val Glu Leu Tyr Ser Ser Gly Glu Arg Lys Leu Ala Asn Val Phe
        610                 615                 620

Asp Leu Glu Thr Met Phe Arg Glu Tyr Asn Tyr Ala Gln Ser Ile
625                 630                 635                 640

Ser Gly Leu Arg Lys Asp Phe Asp Asn Ser Gln Arg Asn Asn Arg Asp
                645                 650                 655

Arg Ile Ile Gln Asp Phe Ser Glu Ile Leu Ala Asp Leu Gly Ser Ile
            660                 665                 670

Gly Lys Val Ile Val Asn Val Ala Ser Gly Ala Phe Ser Leu Phe Gly
        675                 680                 685

Gly Ile Val Thr Gly Ile Leu Asn Phe Ile Lys Asn Pro Leu Gly Gly
    690                 695                 700

Met Phe Thr Phe Leu Leu Ile Gly Ala Val Ile Ile Leu Val Ile Leu
705                 710                 715                 720

Leu Val Arg Arg Thr Asn Asn Met Ser Gln Ala Pro Ile Arg Met Ile
                725                 730                 735

Tyr Pro Asp Val Glu Lys Ser Lys Ser Thr Val Thr Pro Met Glu Pro
            740                 745                 750

Glu Thr Ile Lys Gln Ile Leu Leu Gly Met His Asn Met Gln Gln Glu
        755                 760                 765

Ala Tyr Lys Lys Lys Glu Glu Gln Arg Ala Ala Arg Pro Ser Ile Phe
    770                 775                 780

Arg Gln Ala Ala Glu Thr Phe Leu
785                 790

<210> SEQ ID NO 43
<211> LENGTH: 824
<212> TYPE: PRT
<213> ORGANISM: Eqyuine herpesvirus 2

<400> SEQUENCE: 43

Met Gly Val Gly Gly Gly Pro Arg Val Val Leu Cys Leu Trp Cys Val
1               5                   10                  15

Ala Ala Leu Leu Cys Gln Gly Val Ala Gln Glu Val Val Ala Glu Thr
            20                  25                  30

Thr Thr Pro Phe Ala Thr His Arg Pro Glu Val Val Ala Glu Glu Asn
        35                  40                  45

Pro Ala Asn Pro Phe Leu Pro Phe Arg Val Cys Gly Ala Ser Pro Thr
    50                  55                  60

Gly Gly Glu Ile Phe Arg Phe Pro Leu Glu Glu Ser Cys Pro Asn Thr
65                  70                  75                  80

Glu Asp Lys Asp His Ile Glu Gly Ile Ala Leu Ile Tyr Lys Thr Asn
                85                  90                  95

Ile Val Pro Tyr Val Phe Asn Val Arg Lys Tyr Arg Lys Ile Met Thr
```

-continued

```
                100                 105                 110
Ser Thr Thr Ile Tyr Lys Gly Trp Ser Glu Asp Ala Ile Thr Asn Gln
            115                 120                 125

His Thr Arg Ser Tyr Ala Val Pro Leu Tyr Glu Val Gln Met Met Asp
        130                 135                 140

His Tyr Gln Cys Phe Ser Ala Val Gln Val Asn Glu Gly Gly His
145                 150                 155                 160

Val Asn Thr Tyr Tyr Asp Arg Asp Gly Trp Asn Glu Thr Ala Phe Leu
                165                 170                 175

Lys Pro Ala Asp Gly Leu Thr Ser Ser Ile Thr Arg Tyr Gln Ser Gln
            180                 185                 190

Pro Glu Val Tyr Ala Thr Pro Arg Asn Leu Leu Trp Ser Tyr Thr Thr
        195                 200                 205

Arg Thr Thr Val Asn Cys Glu Val Thr Glu Met Ser Ala Arg Ser Met
    210                 215                 220

Lys Pro Phe Glu Phe Phe Val Thr Ser Val Gly Asp Thr Ile Glu Met
225                 230                 235                 240

Ser Pro Phe Leu Lys Glu Asn Gly Thr Glu Pro Glu Lys Ile Leu Lys
                245                 250                 255

Arg Pro His Ser Ile Gln Leu Leu Lys Asn Tyr Ala Val Thr Lys Tyr
            260                 265                 270

Gly Val Gly Leu Gly Gln Ala Asp Asn Ala Thr Arg Phe Phe Ala Ile
        275                 280                 285

Phe Gly Asp Tyr Ser Leu Ser Trp Lys Ala Thr Thr Glu Asn Ser Ser
    290                 295                 300

Tyr Cys Asp Leu Ile Leu Trp Lys Gly Phe Ser Asn Ala Ile Gln Thr
305                 310                 315                 320

Gln His Asn Ser Ser Leu His Phe Ile Ala Asn Asp Ile Thr Ala Ser
                325                 330                 335

Phe Ser Thr Pro Leu Glu Glu Glu Ala Asn Phe Asn Glu Thr Phe Lys
            340                 345                 350

Cys Ile Trp Asn Asn Thr Gln Glu Glu Ile Gln Lys Lys Leu Lys Glu
        355                 360                 365

Val Glu Lys Thr His Arg Pro Asn Gly Thr Ala Lys Val Tyr Lys Thr
    370                 375                 380

Thr Gly Asn Leu Tyr Ile Val Trp Gln Pro Leu Ile Gln Ile Asp Leu
385                 390                 395                 400

Leu Asp Thr His Ala Lys Leu Tyr Asn Leu Thr Asn Ala Thr Ala Ser
                405                 410                 415

Pro Thr Ser Thr Pro Thr Thr Ser Pro Arg Arg Arg Arg Asp Thr
            420                 425                 430

Ser Ser Val Ser Gly Gly Asn Asn Gly Asp Asn Ser Thr Lys Glu
        435                 440                 445

Glu Ser Val Ala Ala Ser Gln Val Gln Phe Ala Tyr Asp Asn Leu Arg
    450                 455                 460

Lys Ser Ile Asn Arg Val Leu Gly Glu Leu Ser Arg Ala Trp Cys Arg
465                 470                 475                 480

Glu Gln Tyr Arg Ala Ser Leu Met Trp Tyr Glu Leu Ser Lys Ile Asn
                485                 490                 495

Pro Thr Ser Val Met Ser Ala Ile Tyr Gly Arg Pro Val Ser Ala Lys
            500                 505                 510

Leu Ile Gly Asp Val Val Ser Val Ser Asp Cys Ile Ser Val Asp Gln
        515                 520                 525
```

```
Lys Ser Val Phe Val His Lys Asn Met Lys Val Pro Gly Lys Glu Asp
            530                 535                 540

Leu Cys Tyr Thr Arg Pro Val Gly Phe Lys Phe Ile Asn Gly Ser
545                 550                 555                 560

Glu Leu Phe Ala Gly Gln Leu Gly Pro Arg Asn Glu Ile Val Leu Ser
                565                 570                 575

Thr Ser Gln Val Glu Val Cys Gln His Ser Cys Glu His Tyr Phe Gln
                580                 585                 590

Ala Gly Asn Gln Met Tyr Lys Tyr Lys Asp Tyr Tyr Val Ser Thr
                595                 600                 605

Leu Asn Leu Thr Asp Ile Pro Thr Leu His Thr Met Ile Thr Leu Asn
            610                 615                 620

Leu Ser Leu Val Glu Asn Ile Asp Phe Lys Val Ile Glu Leu Tyr Ser
625                 630                 635                 640

Lys Thr Glu Lys Arg Leu Ser Asn Val Phe Asp Ile Glu Thr Met Phe
                645                 650                 655

Arg Glu Tyr Asn Tyr Tyr Thr Gln Asn Leu Asn Gly Leu Arg Lys Asp
                660                 665                 670

Leu Asp Asp Ser Ile Asp His Gly Arg Asp Ser Phe Ile Gln Thr Leu
            675                 680                 685

Gly Asp Ile Met Gln Asp Leu Gly Thr Ile Gly Lys Val Val Asn
            690                 695                 700

Val Ala Ser Gly Val Phe Ser Leu Phe Gly Ser Ile Val Ser Gly Val
705                 710                 715                 720

Ile Ser Phe Phe Lys Asn Pro Phe Gly Gly Met Leu Leu Ile Val Leu
                725                 730                 735

Ile Ile Ala Gly Val Val Val Tyr Leu Phe Met Thr Arg Ser Arg
                740                 745                 750

Ser Ile Tyr Ser Ala Pro Ile Arg Met Leu Tyr Pro Gly Val Glu Arg
            755                 760                 765

Ala Ala Gln Glu Pro Gly Ala His Pro Val Ser Glu Asp Gln Ile Arg
770                 775                 780

Asn Ile Leu Met Gly Met His Gln Phe Gln Gln Arg Gln Arg Ala Glu
785                 790                 795                 800

Glu Glu Ala Arg Arg Glu Glu Val Lys Gly Lys Arg Thr Leu Phe
                805                 810                 815

Glu Val Ile Arg Asp Ser Ala Thr
            820

<210> SEQ ID NO 44
<211> LENGTH: 818
<212> TYPE: PRT
<213> ORGANISM: Equine herpesvirus 5

<400> SEQUENCE: 44

Met Val Ala Trp Phe Gly Leu Trp Gly Phe Ala Arg Leu Met Ala Thr
1               5                   10                  15

Leu Ala Leu Leu Cys Gly Arg Val Ala Leu Asp Glu Ser Ser Ala Thr
                20                  25                  30

Pro Ser Ile Pro Pro Thr His Lys Pro Ala Val His His Glu Asp Asn
            35                  40                  45

Thr Thr Asn Pro Phe Leu Leu Phe Arg Val Cys Gly Ala Ser Pro Thr
        50                  55                  60

Gly Glu Ile Phe Arg Phe Pro Leu Glu Glu Asn Cys Pro Asn Thr Glu
```

-continued

```
                65                  70                  75                  80
Asp Lys Glu His Val Glu Gly Ile Leu Leu Ile Tyr Lys Thr Asn Ile
                    85                  90                  95
Val Pro Tyr Ile Phe Asn Val Arg Lys Tyr Arg Lys Leu Val Thr Ser
                    100                 105                 110
Thr Thr Ile Tyr Lys Gly Trp Ser Gln Asp Ala Ile Thr Asn Gln Tyr
                    115                 120                 125
Thr Ser Ser Phe Ala Met Pro Leu Trp Glu Ala Arg Leu Val Asp Tyr
            130                 135                 140
Asn Tyr Glu Cys Tyr Asn Gly Ile Gln Val Thr Glu Asn Gly His Leu
145                 150                 155                 160
Thr Thr Tyr Val Asp Arg Asp Gly Tyr Asn Glu Ser Val Arg Leu Val
                    165                 170                 175
Pro Ala Asp Gly Leu Thr Ser Ser Ile Arg Arg Tyr His Ser Gln Pro
                    180                 185                 190
Glu Leu Tyr Val Thr Pro Arg Asn Leu Leu Trp Ser Tyr Thr Thr Arg
                    195                 200                 205
Thr Thr Val Asn Cys Glu Val Ile Asp Met Thr Ala Arg Ser His Lys
            210                 215                 220
Pro Phe Glu Tyr Phe Val Thr Ala Ser Gly Asp Ser Ile Glu Thr Ser
225                 230                 235                 240
Pro Phe Tyr Thr Asn Ala Ser Arg Arg Val Pro Val Gln Val Leu Tyr
                    245                 250                 255
Asn Tyr Ser Val Thr Asp Tyr Gly Val Gly Leu Gly Ser Gly Glu Asn
                    260                 265                 270
Val Thr Arg Phe Phe Ala Thr Leu Asn Asp Phe Ser Ile Ser Trp Lys
                    275                 280                 285
Ala Ala Thr Glu Asn Ser Ser Tyr Cys Pro Leu Val Leu Trp Lys Gly
            290                 295                 300
Phe Pro Ser Ala Ile Gln Thr Lys His Glu Lys Ser Tyr His Phe Ile
305                 310                 315                 320
Ala Asp Ala Val Thr Ala Ser Phe Thr Thr Pro Leu Thr Asp Glu Thr
                    325                 330                 335
Ser Tyr Phe Asn Thr Thr Tyr Gln Cys Ala Trp Gln Asp Ile Glu Gly
                    340                 345                 350
Glu Ile Gln Lys Arg Phe Asp Pro Val Ser Lys Thr His Ala Arg Asn
            355                 360                 365
Gly Ser Val Gln Ile Tyr Lys Thr Ser Gly Asn Leu Tyr Val Val Trp
370                 375                 380
Gln Pro Leu Val Gln Leu Asp Leu Leu Ala Ala His Ala Lys Thr Ile
385                 390                 395                 400
Asn Ser Thr Asp Asn Ser Thr Ser Pro Thr Thr Ala Pro Asn Thr Thr
                    405                 410                 415
Thr Ser Thr Ser Ser Arg Arg Lys Arg Asp Thr Gly Asn Thr Ala
            420                 425                 430
Thr Asn Asn Ser Ser Ser Asn Asn Ser Ser Met Glu Glu Asn Leu Ala
            435                 440                 445
Thr Ser Gln Val Gln Phe Ala Tyr Asp Gln Leu Arg Lys Ser Ile Asn
        450                 455                 460
Arg Val Leu Glu Gln Leu Ser Arg Val Trp Cys Gln Asn Gln Tyr Arg
465                 470                 475                 480
Ala Ser Leu Met Trp Tyr Glu Leu Ser Lys Ile Asn Pro Thr Ser Val
                    485                 490                 495
```

```
Met Ser Ala Ile Tyr Gly Arg Pro Val Ser Ala Lys Leu Val Gly Asp
                500                 505                 510

Val Val Gln Ile Ser Asp Cys Ile Thr Val Asp Gln Glu Ser Val Phe
            515                 520                 525

Val His Arg Asn Leu Arg Val Pro Gly Ser Lys Asp Leu Cys Tyr Thr
        530                 535                 540

Arg Pro Val Val Gly Phe Lys Phe Ile Asn Gly Ser Glu Leu Phe Val
545                 550                 555                 560

Gly Gln Leu Gly Ala Arg Asn Glu Ile Leu Leu Ser Thr Asn Leu Val
                565                 570                 575

Glu Val Cys Gln His Ser Cys Glu His Tyr Phe Gln Gly Gly Asn His
            580                 585                 590

Ile Tyr Lys Tyr Lys Asn Tyr Glu Tyr Val Ser Thr Met Asn Leu Thr
        595                 600                 605

Asp Val Pro Thr Leu His Thr Met Ile Thr Leu Asn Leu Ser Leu Val
        610                 615                 620

Glu Asn Val Asp Phe Gln Val Ile Gln Leu Tyr Ser Gln Lys Glu Lys
625                 630                 635                 640

Lys Leu Ser Asn Val Phe Asp Ile Glu Thr Met Phe Arg Glu Tyr Asn
                645                 650                 655

Tyr Tyr Thr Gln Asn Leu Lys Gly Leu Arg Lys Asp Leu Asp Asp Ser
            660                 665                 670

Ile His Asp Gly Arg Asp Ser Phe Ile Gln Phe Leu Gly Asp Leu Val
        675                 680                 685

Gln Asp Leu Val Pro Val Gly Asp Val Ile Val Asn Val Ala Ser Gly
        690                 695                 700

Val Phe Ser Leu Phe Gly Ser Ile Val Ser Gly Val Ile Ser Phe Leu
705                 710                 715                 720

Lys Asn Pro Leu Gly Ala Ile Leu Thr Ile Ala Leu Ile Val Gly Gly
                725                 730                 735

Ile Ile Val Leu Tyr Leu Phe Ile Thr Arg Ser Arg Thr Val Tyr Gln
            740                 745                 750

Ala Pro Ile Arg Met Leu Tyr Pro Glu Val Asp Arg Ala Pro Gln Gln
        755                 760                 765

Asn Val Gln Pro Ile Pro Glu Asp Gln Val Arg Ser Ile Leu Leu Ala
        770                 775                 780

Met His Gln Phe Gln Gln Gln Gln Gln Gln Gln Gln Gln Gln Gln Gln
785                 790                 795                 800

Glu Glu His Thr Gln Arg Arg Ser Ile Phe Asp Thr Ile Arg Glu Ser
                805                 810                 815

Thr Ser

<210> SEQ ID NO 45
<211> LENGTH: 830
<212> TYPE: PRT
<213> ORGANISM: Alcelaphine herpesvirus

<400> SEQUENCE: 45

Met Ala His Thr Gly Ser Thr Val Cys Ala Phe Leu Ile Phe Ala Val
1               5                   10                  15

Leu Lys Asn Val Phe Cys Gln Thr Pro Thr Ser Ser Glu Val Glu
            20                  25                  30

Asp Val Ile Pro Glu Ala Asn Thr Val Ser Asp Asn Ile Ile Arg Gln
        35                  40                  45
```

-continued

```
Gln Arg Asn Asn Thr Ala Lys Gly Ile His Ser Asp Pro Ser Ala Phe
        50                  55                  60

Pro Phe Arg Val Cys Ser Ala Ser Asn Ile Gly Asp Ile Phe Arg Phe
65                  70                  75                  80

Gln Thr Ser His Ser Cys Pro Asn Thr Lys Asp Lys Glu His Asn Glu
                85                  90                  95

Gly Ile Leu Leu Ile Phe Lys Glu Asn Ile Val Pro Tyr Val Phe Lys
                100                 105                 110

Val Arg Lys Tyr Arg Lys Ile Val Thr Thr Ser Thr Ile Tyr Asn Gly
            115                 120                 125

Ile Tyr Ala Asp Ala Val Thr Asn Gln His Val Phe Ser Lys Ser Val
        130                 135                 140

Pro Ile Tyr Glu Thr Arg Arg Met Asp Thr Ile Tyr Gln Cys Tyr Asn
145                 150                 155                 160

Ser Leu Asp Val Thr Val Gly Gly Asn Leu Leu Val Tyr Thr Asp Asn
                165                 170                 175

Asp Gly Ser Asn Met Thr Val Asp Leu Gln Pro Val Asp Gly Leu Ser
                180                 185                 190

Asn Ser Val Arg Arg Tyr His Ser Gln Pro Glu Ile His Ala Glu Pro
            195                 200                 205

Gly Trp Leu Leu Gly Gly Tyr Arg Arg Thr Thr Val Asn Cys Glu
        210                 215                 220

Val Thr Glu Thr Asp Ala Arg Ala Val Pro Pro Phe Arg Tyr Phe Ile
225                 230                 235                 240

Thr Asn Ile Gly Asp Thr Ile Glu Met Ser Pro Phe Trp Ser Lys Ala
                245                 250                 255

Trp Asn Glu Thr Glu Phe Ser Gly Glu Pro Asp Arg Thr Leu Thr Val
                260                 265                 270

Ala Lys Asp Tyr Arg Val Val Asp Tyr Lys Phe Arg Gly Thr Gln Pro
            275                 280                 285

Gln Gly His Thr Arg Ile Phe Val Asp Lys Glu Glu Tyr Thr Leu Ser
        290                 295                 300

Trp Ala Gln Gln Phe Arg Asn Ile Ser Tyr Cys Arg Trp Ala His Trp
305                 310                 315                 320

Lys Ser Phe Asp Asn Ala Ile Lys Thr Glu His Gly Lys Ser Leu His
                325                 330                 335

Phe Val Ala Asn Asp Ile Thr Ala Ser Phe Tyr Thr Pro Asn Thr Gln
                340                 345                 350

Thr Arg Glu Val Leu Gly Lys His Val Cys Leu Asn Asn Thr Ile Glu
            355                 360                 365

Ser Glu Leu Lys Ser Arg Leu Ala Lys Val Asn Asp Thr His Ser Pro
        370                 375                 380

Asn Gly Thr Ala Gln Tyr Tyr Leu Thr Asn Gly Gly Leu Leu Leu Val
385                 390                 395                 400

Trp Gln Pro Leu Val Gln Gln Lys Leu Leu Asp Ala Lys Gly Leu Leu
                405                 410                 415

Asp Ala Val Lys Lys Gln Gln Asn Thr Thr Thr Thr Thr Thr Thr Thr
                420                 425                 430

Arg Ser Arg Arg Gln Arg Arg Ser Val Ser Ser Gly Ile Asp Asp Val
            435                 440                 445

Tyr Thr Ala Glu Ser Thr Ile Leu Leu Thr Gln Ile Gln Phe Ala Tyr
450                 455                 460
```

-continued

Asp Thr Leu Arg Ala Gln Ile Asn Asn Val Leu Glu Leu Ser Arg
465                 470                 475                 480

Ala Trp Cys Arg Glu Gln His Arg Ala Ser Leu Met Trp Asn Glu Leu
            485                 490                 495

Ser Lys Ile Asn Pro Thr Ser Val Met Ser Ser Ile Tyr Gly Arg Pro
        500                 505                 510

Val Ser Ala Lys Arg Ile Gly Asp Val Ile Ser Val Ser His Cys Val
    515                 520                 525

Val Val Asp Gln Asp Ser Val Ser Leu His Arg Ser Met Arg Val Pro
530                 535                 540

Gly Arg Asp Lys Thr His Glu Cys Tyr Ser Arg Pro Pro Val Thr Phe
545                 550                 555                 560

Lys Phe Ile Asn Asp Ser His Leu Tyr Lys Gly Gln Leu Gly Val Asn
                565                 570                 575

Asn Glu Ile Leu Leu Thr Thr Thr Ala Val Glu Ile Cys His Glu Asn
            580                 585                 590

Thr Glu His Tyr Phe Gln Gly Gly Asn Asn Met Tyr Phe Tyr Lys Asn
        595                 600                 605

Tyr Arg His Val Lys Thr Met Pro Val Gly Asp Val Ala Thr Leu Asp
    610                 615                 620

Thr Phe Met Val Leu Asn Leu Thr Leu Val Glu Asn Ile Asp Phe Gln
625                 630                 635                 640

Val Ile Glu Leu Tyr Ser Arg Glu Glu Lys Arg Met Ser Thr Ala Phe
                645                 650                 655

Asp Ile Glu Thr Met Phe Arg Glu Tyr Asn Tyr Tyr Thr Gln Arg Val
            660                 665                 670

Thr Gly Leu Arg Arg Asp Leu Thr Asp Leu Ala Thr Asn Arg Asn Gln
        675                 680                 685

Phe Val Asp Ala Phe Gly Ser Leu Met Asp Asp Leu Gly Val Val Gly
    690                 695                 700

Lys Thr Val Leu Asn Ala Val Ser Ser Val Ala Thr Leu Phe Ser Ser
705                 710                 715                 720

Ile Val Ser Gly Ile Ile Asn Phe Ile Lys Asn Pro Phe Gly Gly Met
                725                 730                 735

Leu Leu Phe Gly Leu Ile Ala Ala Val Val Ile Thr Val Ile Leu Leu
            740                 745                 750

Asn Arg Lys Ala Lys Arg Phe Ala Gln Asn Pro Val Gln Met Ile Tyr
        755                 760                 765

Pro Asp Ile Lys Thr Ile Thr Ser Gln Arg Glu Glu Leu Gln Val Asp
    770                 775                 780

Pro Ile Ser Lys His Glu Leu Asp Arg Ile Met Leu Ala Met His Asp
785                 790                 795                 800

Tyr His Ala Ser Lys Gln Pro Glu Ser Lys Gln Asp Glu Glu Gln Gly
                805                 810                 815

Ser Thr Thr Ser Gly Pro Ala Asp Trp Leu Asn Lys Ala Lys
            820                 825                 830

<210> SEQ ID NO 46
<211> LENGTH: 829
<212> TYPE: PRT
<213> ORGANISM: Epstein-Barr virus

<400> SEQUENCE: 46

Met Thr Arg Arg Arg Val Leu Ser Val Val Leu Leu Ala Ala Leu
1               5                   10                  15

-continued

```
Ala Cys Arg Leu Gly Ala Gln Thr Pro Glu Gln Pro Ala Pro Ala
         20                  25                  30

Thr Thr Val Gln Pro Thr Ala Thr Arg Gln Gln Thr Ser Phe Pro Phe
         35                  40                  45

Arg Val Cys Glu Leu Ser Ser His Gly Asp Leu Phe Arg Phe Ser Ser
 50                  55                  60

Asp Ile Gln Cys Pro Ser Phe Gly Thr Arg Glu Asn His Thr Glu Gly
 65                  70                  75                  80

Leu Leu Met Val Phe Lys Asp Asn Ile Ile Pro Tyr Ser Phe Lys Val
                 85                  90                  95

Arg Ser Tyr Thr Lys Ile Val Thr Asn Ile Leu Ile Tyr Asn Gly Trp
             100                 105                 110

Tyr Ala Asp Ser Val Thr Asn Arg His Glu Glu Lys Phe Ser Val Asp
             115                 120                 125

Ser Tyr Glu Thr Asp Gln Met Asp Thr Ile Tyr Gln Cys Tyr Asn Ala
         130                 135                 140

Val Lys Met Thr Lys Asp Gly Leu Thr Arg Val Tyr Val Asp Arg Asp
145                 150                 155                 160

Gly Val Asn Ile Thr Val Asn Leu Lys Pro Thr Gly Leu Ala Asn
                 165                 170                 175

Gly Val Arg Arg Tyr Ala Ser Gln Thr Glu Leu Tyr Asp Ala Pro Gly
             180                 185                 190

Trp Leu Ile Trp Thr Tyr Arg Thr Arg Thr Thr Val Asn Cys Leu Ile
             195                 200                 205

Thr Asp Met Met Ala Lys Ser Asn Ser Pro Phe Asp Phe Val Thr
    210                 215                 220

Thr Thr Gly Gln Thr Val Glu Met Ser Pro Phe Tyr Asp Gly Lys Asn
225                 230                 235                 240

Lys Glu Thr Phe His Glu Arg Ala Asp Ser Phe His Val Arg Thr Asn
                 245                 250                 255

Tyr Lys Ile Val Asp Tyr Asp Asn Arg Gly Thr Asn Pro Gln Gly Glu
             260                 265                 270

Arg Arg Ala Phe Leu Asp Lys Gly Thr Tyr Thr Leu Ser Trp Lys Leu
         275                 280                 285

Glu Asn Arg Thr Ala Tyr Cys Pro Leu Gln His Trp Gln Thr Phe Asp
    290                 295                 300

Ser Thr Ile Ala Thr Glu Thr Gly Lys Ser Ile His Phe Val Thr Asp
305                 310                 315                 320

Glu Gly Thr Ser Ser Phe Val Thr Asn Thr Thr Val Gly Ile Glu Leu
                 325                 330                 335

Pro Asp Ala Phe Lys Cys Ile Glu Glu Gln Val Asn Lys Thr Met His
             340                 345                 350

Glu Lys Tyr Glu Ala Val Gln Asp Arg Tyr Thr Lys Gly Gln Glu Ala
         355                 360                 365

Ile Thr Tyr Phe Ile Thr Ser Gly Gly Leu Leu Leu Ala Trp Leu Pro
    370                 375                 380

Leu Thr Pro Arg Ser Leu Ala Thr Val Lys Asn Leu Thr Glu Leu Thr
385                 390                 395                 400

Thr Pro Thr Ser Ser Pro Pro Ser Pro Ser Pro Ala Pro Ser
                 405                 410                 415

Ala Ala Arg Gly Ser Thr Pro Ala Ala Val Leu Arg Arg Arg Arg
             420                 425                 430
```

```
Asp Ala Gly Asn Ala Thr Thr Pro Val Pro Thr Ala Pro Gly Lys
        435                 440                 445
Ser Leu Gly Thr Leu Asn Asn Pro Ala Thr Val Gln Ile Gln Phe Ala
    450                 455                 460
Tyr Asp Ser Leu Arg Arg Gln Ile Asn Arg Met Leu Gly Asp Leu Ala
465                 470                 475                 480
Arg Ala Trp Cys Leu Glu Gln Lys Arg Gln Asn Met Val Leu Arg Glu
                485                 490                 495
Leu Thr Lys Ile Asn Pro Thr Thr Val Met Ser Ser Ile Tyr Gly Lys
                500                 505                 510
Ala Val Ala Ala Lys Arg Leu Gly Asp Val Ile Ser Val Ser Gln Cys
            515                 520                 525
Val Pro Val Asn Gln Ala Thr Val Thr Leu Arg Lys Ser Met Arg Val
        530                 535                 540
Pro Gly Ser Glu Thr Met Cys Tyr Ser Arg Pro Leu Val Ser Phe Ser
545                 550                 555                 560
Phe Ile Asn Asp Thr Lys Thr Tyr Glu Gly Gln Leu Gly Thr Asp Asn
                565                 570                 575
Glu Ile Phe Leu Thr Lys Lys Met Thr Glu Val Cys Gln Ala Thr Ser
                580                 585                 590
Gln Tyr Tyr Phe Gln Ser Gly Asn Glu Ile His Val Tyr Asn Asp Tyr
            595                 600                 605
His His Phe Lys Thr Ile Glu Leu Asp Gly Ile Ala Thr Leu Gln Thr
        610                 615                 620
Phe Ile Ser Leu Asn Thr Ser Leu Ile Glu Asn Ile Asp Phe Ala Ser
625                 630                 635                 640
Leu Glu Leu Tyr Ser Arg Asp Glu Gln Arg Ala Ser Asn Val Phe Asp
                645                 650                 655
Leu Glu Gly Ile Phe Arg Glu Tyr Asn Phe Gln Ala Gln Asn Ile Ala
                660                 665                 670
Gly Leu Arg Lys Asp Leu Asp Asn Ala Val Ser Asn Gly Arg Asn Gln
            675                 680                 685
Phe Val Asp Gly Leu Gly Glu Leu Met Asp Ser Leu Gly Ser Val Gly
        690                 695                 700
Gln Ser Ile Thr Asn Leu Val Ser Thr Val Gly Gly Leu Phe Ser Ser
705                 710                 715                 720
Leu Val Ser Gly Phe Ile Ser Phe Phe Lys Asn Pro Phe Gly Gly Met
                725                 730                 735
Leu Ile Leu Val Leu Val Ala Gly Val Val Ile Leu Val Ile Ser Leu
                740                 745                 750
Thr Arg Arg Thr Arg Gln Met Ser Gln Gln Pro Val Gln Met Leu Tyr
            755                 760                 765
Pro Gly Ile Asp Glu Leu Ala Gln Gln His Ala Ser Gly Glu Gly Pro
        770                 775                 780
Gly Ile Asn Pro Ile Ser Lys Thr Glu Leu Gln Ala Ile Met Leu Ala
785                 790                 795                 800
Leu His Glu Gln Asn Gln Glu Gln Lys Arg Ala Ala Gln Arg Ala Ala
                805                 810                 815
Gly Pro Ser Val Ala Ser Arg Ala Leu Gln Ala Ala Arg
            820                 825

<210> SEQ ID NO 47
<211> LENGTH: 660
<212> TYPE: DNA
```

-continued

<213> ORGANISM: Artificial Sequence
<220> FEATURE:
<223> OTHER INFORMATION: Suid herpesvirus 1 - bases 641-1300

<400> SEQUENCE: 47
cgccgccgtc cggctccacg gtggtgcggc tggagcccga gcaggcctgc cccgagtact 60
cgcaggggcg caacttcacg gaggggatcg ccgtgctctt caaggagaac atcgccccgc 120
acaagttcaa ggcccacatc tactacaaga acgtcatcgt cacgaccgtg tggtccggga 180
gcacgtacgc ggccatcacg aaccgcttca cagaccgcgt gcccgtcccc gtgcaggaga 240
tcacggacgt gatcgaccgc cgcggcaagt gcgtctccaa ggccgagtac gtgcgcaaca 300
accacaaggt gaccgccttc gaccgcgacg agaaccccgt cgaggtggac ctgcgcccct 360
cgcgcctgaa cgcgctcggc acccgcggct ggcacaccac caacgacacc tacaccaaga 420
tcggcgccgc gggcttctac cacacgggca cctccgtcaa ctgcatcgtc gaggaggtgg 480
aggcgcgctc cgtgtacccc tacgactcct tcgccctgtc cacgggggac attgtgtaca 540
tgtccccctt ctacggcctg cgcgaggggg cccacgggga gcacatcggc tacgcgcccg 600
ggcgcttcca gcaggtggag cactactacc ccatcgacct ggactcgcgc ctccgcgcct 660

<210> SEQ ID NO 48
<211> LENGTH: 359
<212> TYPE: PRT
<213> ORGANISM: Artificial Sequence
<220> FEATURE:
<223> OTHER INFORMATION: Suid herpesvirus 1 - bases 491-850

<400> SEQUENCE: 48

```
Ala Ala Pro Ala Ala Ala Arg Arg Ala Arg Arg Ser Pro Gly Pro Ala
1               5                   10                  15

Gly Thr Pro Glu Pro Pro Ala Val Asn Gly Thr Gly His Leu Arg Ile
            20                  25                  30

Thr Thr Gly Ser Ala Glu Phe Ala Arg Leu Gln Phe Thr Tyr Asp His
        35                  40                  45

Ile Gln Ala His Val Asn Asp Met Leu Gly Arg Ile Ala Ala Ala Trp
    50                  55                  60

Cys Glu Leu Gln Asn Lys Asp Arg Thr Leu Trp Ser Glu Met Ser Arg
65                  70                  75                  80

Leu Asn Pro Ser Ala Val Ala Thr Ala Ala Leu Gly Gln Arg Val Ser
                85                  90                  95

Ala Arg Met Leu Gly Asp Val Met Ala Ile Ser Arg Cys Val Glu Val
            100                 105                 110

Arg Gly Gly Val Tyr Val Gln Asn Ser Met Arg Val Pro Gly Glu Arg
        115                 120                 125

Gly Thr Cys Tyr Ser Arg Pro Leu Val Thr Phe Glu His Asn Gly Thr
    130                 135                 140

Gly Val Ile Glu Gly Gln Leu Gly Asp Asp Asn Glu Leu Leu Ile Ser
145                 150                 155                 160

Arg Asp Leu Ile Glu Pro Cys Thr Gly Asn His Arg Arg Tyr Phe Lys
                165                 170                 175

Leu Gly Ser Gly Tyr Val Tyr Tyr Glu Asp Tyr Asn Tyr Val Arg Met
            180                 185                 190

Val Glu Val Pro Glu Thr Ile Ser Thr Arg Val Thr Leu Asn Leu Thr
        195                 200                 205

Leu Leu Glu Asp Arg Glu Phe Leu Pro Leu Glu Val Tyr Thr Arg Glu
    210                 215                 220
```

-continued

```
Glu Leu Ala Asp Thr Gly Leu Leu Asp Tyr Ser Glu Ile Gln Arg Arg
225                 230                 235                 240

Asn Gln Leu His Ala Leu Lys Phe Tyr Asp Ile Asp Arg Val Val Lys
                245                 250                 255

Val Asp His Asn Val Val Leu Leu Arg Gly Ile Ala Asn Phe Phe Gln
            260                 265                 270

Gly Leu Gly Asp Val Gly Ala Ala Val Gly Lys Val Val Leu Gly Ala
        275                 280                 285

Thr Gly Ala Val Ile Ser Ala Val Gly Gly Met Val Ser Phe Leu Ser
    290                 295                 300

Asn Pro Phe Gly Ala Leu Ala Ile Gly Leu Leu Val Leu Ala Gly Leu
305                 310                 315                 320

Val Ala Ala Phe Leu Ala Tyr Arg His Ile Ser Arg Leu Arg Arg Asn
                325                 330                 335

Pro Met Lys Ala Leu Tyr Pro Val Thr Thr Lys Thr Leu Lys Glu Asp
            340                 345                 350

Gly Val Asp Glu Gly Asp Val
        355

<210> SEQ ID NO 49
<211> LENGTH: 420
<212> TYPE: DNA
<213> ORGANISM: Suid herpesvirus 2

<400> SEQUENCE: 49
ccagcataat gatagccaat aatctgtgtt actctaccct gatcttaaat gacgaggacg      60
tgacggggat cgacgagaaa gatattctga cggtgcatgt aaacaagaat accgtgtaca     120
ggttcgttag gagcagcgtc agggagtcta tactcggcac gctgctgtct agatggctca     180
ggaagagaaa ggaagtgaag gcgcgcatga aacgctgtga ggaccctatg ttggcactga     240
tacttgacaa gcagcagctt gccctcaagg tgacgtgcaa tgcgttttac ggcttcacgg     300
gagccgtgca cggtctgctg ccgtgtctcc ctctagcggc gtccatcacc agcatagggc     360
gggacatgct taggcagacg agtgacttta tcaacaatgt cctttcgtct agagaatacg     420

<210> SEQ ID NO 50
<211> LENGTH: 159
<212> TYPE: PRT
<213> ORGANISM: Suid herpesvirus 2

<400> SEQUENCE: 50

Ser Ile Met Ile Ala Asn Asn Leu Cys Tyr Ser Thr Leu Ile Leu Asn
1               5                   10                  15

Asp Glu Asp Val Thr Gly Ile Asp Glu Lys Asp Ile Leu Thr Val His
            20                  25                  30

Val Asn Lys Asn Thr Val Tyr Arg Phe Val Arg Ser Ser Val Arg Glu
        35                  40                  45

Ser Ile Leu Gly Thr Leu Leu Ser Arg Trp Leu Arg Lys Arg Lys Glu
    50                  55                  60

Val Lys Ala Arg Met Lys Arg Cys Glu Asp Pro Met Leu Ala Leu Ile
65                  70                  75                  80

Leu Asp Lys Gln Gln Leu Ala Leu Lys Val Thr Cys Asn Ala Phe Tyr
                85                  90                  95

Gly Phe Thr Gly Ala Val His Gly Leu Leu Pro Cys Leu Pro Leu Ala
            100                 105                 110
```

Ala Ser Ile Thr Ser Ile Gly Arg Asp Met Leu Arg Gln Thr Ser Asp
        115                 120                 125

Phe Ile Asn Asn Val Leu Ser Ser Arg Glu Tyr Val Ser Glu Lys Phe
    130                 135                 140

Ser Leu Ser Asp Gly Asp Phe Gln Gly Asp Phe Ser Pro Glu Cys
145                 150                 155

<210> SEQ ID NO 51
<211> LENGTH: 466
<212> TYPE: DNA
<213> ORGANISM: Artificial Sequence
<220> FEATURE:
<223> OTHER INFORMATION: Portion of porcine gamma herpesvirus polymerase
      - AF118399

<400> SEQUENCE: 51

```
taatctatgt cactctaccc taatccatca tgaagacctg cataaatatc ctcaattaaa      60
ggaggaggat tatgaaacat ttttgattag ttctggtcct gttcactttg taaaaaaaca    120
catatcagaa tctcttctgt ctaacctgct tacaacatgg ctggctaaga gaaaaatgat    180
cagaaaggaa ttagcagcat gtgctgaccc aaagctcagg acaattttag ataaacagca    240
gcttgcaatt aaggtgacat gcaatgctgt gtatgggttc actggtgttg catctggtat    300
gctgccctgt ctcaagattg cagagaccat aactatgcaa ggaagggcca tgttggaaaa    360
gacaaaagta tttgtagaga atttaagtca tgaggatctc cattccatct gtaaggttgg    420
ctttatgcct cagtcaccaa acagcattga taaacccttc aaggtg                   466
```

<210> SEQ ID NO 52
<211> LENGTH: 423
<212> TYPE: DNA
<213> ORGANISM: Artificial Sequence
<220> FEATURE:
<223> OTHER INFORMATION: Portion of porcine gamma herpesvirus polymerase
      - AF118401

<400> SEQUENCE: 52

```
gaggacctgc ataagtatcc tcaattaaag gaggatgatt atgaaacatt tttgattagt      60
tctggccctg ttcactttgt aaaaaaacac atatcagaat ctcttctgtc gaacttgctc    120
acaacatggc tggccaagag aaaaatgatc agaaggaat tgacagcatg tgctgatcca    180
aagctcagga caattttaga taaacagcag cttgcaatta aggtgacatg caatgctgtg    240
tatggattca ctggtgttgc atctggtatg ctgccatgtc tcaagattgc agagaccatc    300
actatgcaag gaagggccat gttggaaaag acaaaagtat ttgtagagaa tctgagtcat    360
gaagatctcc gttccatatg taaggttggc tctataccte agtcatcaaa cgtgtttgat    420
aaa                                                                 423
```

<210> SEQ ID NO 53
<211> LENGTH: 292
<212> TYPE: DNA
<213> ORGANISM: Artificial Sequence
<220> FEATURE:
<223> OTHER INFORMATION: Portion of Acelaphine herpesvirus.

<400> SEQUENCE: 53

```
aagtaataga actatactct agagaagaga agaggatgag cactgcattt gatatagaga      60
ccatgtttag agaatacaac tactacacac agagggtcac tggcctgcgg agggacttga    120
cagacctagc tacaaacaga aatcaatttg tagatgcctt tggcagcctc atggacgact    180
```

-continued

```
tgggggtcgt ggggaaaacg gtgttgaatg ctgtgagcag tgtggccaca ctcttcagct    240
ctatagtctc agggatcatc aatttcatta aaaacccctt tgggggaatg tt            292

<210> SEQ ID NO 54
<211> LENGTH: 152
<212> TYPE: DNA
<213> ORGANISM: Artificial Sequence
<220> FEATURE:
<223> OTHER INFORMATION: Portion of Acelaphine herpesvirus.

<400> SEQUENCE: 54
tggtgccgtg agcagcaccg agcctctctc atgtggaacg agctaagcaa aatcaaccct     60
accagtgtga tgagctctat atacgggcgg ccagtatctg ccaaaagaat tggagatgtg    120
atatctgtct ctcactgtgt ggtggtggac ca                                  152

<210> SEQ ID NO 55
<211> LENGTH: 793
<212> TYPE: PRT
<213> ORGANISM: Artificial Sequence
<220> FEATURE:
<223> OTHER INFORMATION: Portion of Acelaphine herpesvirus.

<400> SEQUENCE: 55

Lys Gly Ile His Ser Asp Pro Ser Ala Phe Pro Phe Arg Val Cys Ser
1               5                   10                  15

Ala Ser Asn Ile Gly Asp Ile Phe Arg Phe Gln Thr Ser His Ser Cys
            20                  25                  30

Pro Asn Thr Lys Asp Lys Glu His Asn Glu Gly Ile Leu Leu Ile Phe
        35                  40                  45

Lys Glu Asn Ile Val Pro Tyr Val Phe Lys Val Arg Lys Tyr Arg Lys
    50                  55                  60

Ile Val Thr Thr Ser Thr Ile Tyr Asn Gly Ile Tyr Ala Asp Ala Val
65                  70                  75                  80

Thr Asn Gln His Val Phe Ser Lys Ser Val Pro Ile Tyr Glu Thr Arg
                85                  90                  95

Arg Met Asp Thr Ile Tyr Gln Cys Tyr Asn Ser Leu Asp Val Thr Val
            100                 105                 110

Gly Gly Asn Leu Leu Val Tyr Thr Asp Asn Asp Gly Ser Asn Met Thr
        115                 120                 125

Val Asp Leu Gln Pro Val Asp Gly Leu Ser Asn Ser Val Arg Arg Tyr
    130                 135                 140

His Ser Gln Pro Glu Ile His Ala Glu Pro Gly Trp Leu Leu Gly Gly
145                 150                 155                 160

Tyr Arg Arg Arg Thr Thr Val Asn Cys Glu Val Thr Glu Thr Asp Ala
                165                 170                 175

Arg Ala Val Pro Pro Phe Arg Tyr Phe Ile Thr Asn Ile Gly Asp Thr
            180                 185                 190

Ile Glu Met Ser Pro Phe Trp Ser Lys Ala Trp Asn Glu Thr Glu Phe
        195                 200                 205

Ser Gly Glu Pro Asp Arg Thr Leu Thr Val Ala Lys Asp Tyr Arg Val
    210                 215                 220

Val Asp Tyr Lys Phe Arg Gly Thr Gln Pro Gln Gly His Thr Arg Ile
225                 230                 235                 240

Phe Val Asp Lys Glu Glu Tyr Thr Leu Ser Trp Ala Gln Gln Phe Arg
                245                 250                 255

Asn Ile Ser Tyr Cys Arg Trp Ala His Trp Lys Ser Phe Asp Asn Ala
```

-continued

```
                  260                 265                 270
Ile Lys Thr Glu His Gly Lys Ser Leu His Phe Val Ala Asn Asp Ile
        275                 280                 285
Thr Ala Ser Phe Tyr Thr Pro Asn Thr Gln Thr Arg Glu Val Leu Gly
    290                 295                 300
Lys His Val Cys Leu Asn Asn Thr Ile Glu Ser Glu Leu Lys Ser Arg
305                 310                 315                 320
Leu Ala Lys Val Asn Asp Thr His Ser Pro Asn Gly Thr Ala Gln Tyr
                325                 330                 335
Tyr Leu Thr Asn Gly Gly Leu Leu Val Trp Gln Pro Leu Val Gln
        340                 345                 350
Gln Lys Leu Leu Asp Ala Lys Gly Leu Leu Asp Ala Val Lys Lys Gln
            355                 360                 365
Gln Asn Thr Thr Thr Thr Thr Thr Thr Arg Ser Arg Arg Gln Arg
        370                 375                 380
Arg Ser Val Ser Ser Gly Ile Asp Asp Val Tyr Thr Ala Glu Ser Thr
385                 390                 395                 400
Ile Leu Leu Thr Gln Ile Gln Phe Ala Tyr Asp Thr Leu Arg Ala Gln
                405                 410                 415
Ile Asn Asn Val Leu Glu Glu Leu Ser Arg Ala Trp Cys Arg Glu Gln
                420                 425                 430
His Arg Ala Ser Leu Met Trp Asn Glu Leu Ser Lys Ile Asn Pro Thr
        435                 440                 445
Ser Val Met Ser Ser Ile Tyr Gly Arg Pro Val Ser Ala Lys Arg Ile
    450                 455                 460
Gly Asp Val Ile Ser Val Ser His Cys Val Val Val Asp Gln Asp Ser
465                 470                 475                 480
Val Ser Leu His Arg Ser Met Arg Val Pro Gly Arg Asp Lys Thr His
                485                 490                 495
Glu Cys Tyr Ser Arg Pro Pro Val Thr Phe Lys Phe Ile Asn Asp Ser
                500                 505                 510
His Leu Tyr Lys Gly Gln Leu Gly Val Asn Asn Glu Ile Leu Leu Thr
            515                 520                 525
Thr Thr Ala Val Glu Ile Cys His Glu Asn Thr Glu His Tyr Phe Gln
        530                 535                 540
Gly Gly Asn Asn Met Tyr Phe Tyr Lys Asn Tyr Arg His Val Lys Thr
545                 550                 555                 560
Met Pro Val Gly Asp Val Ala Thr Leu Asp Thr Phe Met Val Leu Asn
                565                 570                 575
Leu Thr Leu Val Glu Asn Ile Asp Phe Gln Val Ile Glu Leu Tyr Ser
            580                 585                 590
Arg Glu Glu Lys Arg Met Ser Thr Ala Phe Asp Ile Glu Thr Met Phe
        595                 600                 605
Arg Glu Tyr Asn Tyr Tyr Thr Gln Arg Val Thr Gly Leu Arg Arg Asp
    610                 615                 620
Leu Thr Asp Leu Ala Thr Asn Arg Asn Gln Phe Val Asp Ala Phe Gly
625                 630                 635                 640
Ser Leu Met Asp Asp Leu Gly Val Val Gly Lys Thr Val Leu Asn Ala
                645                 650                 655
Val Ser Ser Val Ala Thr Leu Phe Ser Ser Ile Val Ser Gly Ile Ile
                660                 665                 670
Asn Phe Ile Lys Asn Pro Phe Gly Gly Met Leu Leu Phe Gly Leu Ile
        675                 680                 685
```

-continued

```
Ala Ala Val Val Ile Thr Val Ile Leu Leu Asn Arg Lys Ala Lys Arg
    690                 695                 700

Phe Ala Gln Asn Pro Val Gln Met Ile Pro Asp Ile Lys Thr Ile Thr
705                 710                 715                 720

Ser Gln Arg Glu Glu Leu Gln Val Asp Pro Ile Ser Lys His Glu Leu
                725                 730                 735

Asp Arg Ile Met Leu Ala Met His Asp Tyr His Ala Ser Lys Gln Pro
            740                 745                 750

Glu Ser Lys Gln Asp Glu Glu Gln Gly Ser Thr Thr Ser Gly Pro Ala
        755                 760                 765

Asp Leu Asn Lys Ala Lys Asn Val Leu Arg Arg Arg Ala Gly Tyr Lys
    770                 775                 780

Pro Leu Lys Arg Thr Asp Ser Phe Glu
785                 790
```